(12) United States Patent
Halbwirth et al.

(10) Patent No.: US 8,318,918 B2
(45) Date of Patent: Nov. 27, 2012

(54) CHALCONE 3-HYDROXYLASE

(75) Inventors: Heidrun Halbwirth, Vienna (AT);
Karin Schlangen, Vienna (AT); Karl Stich, Gerasdorf (AT)

(73) Assignee: Technische Universitat Wien, Vienna (AT)

( * ) Notice: Subject to any disclaimer, the term of this patent is extended or adjusted under 35 U.S.C. 154(b) by 189 days.

(21) Appl. No.: 12/651,250

(22) Filed: Dec. 31, 2009

(65) Prior Publication Data
US 2011/0055980 A1    Mar. 3, 2011

(30) Foreign Application Priority Data

Aug. 26, 2009  (AT) .................... 1342/2009

(51) Int. Cl.
*C12N 15/29*   (2006.01)
*C12N 15/82*   (2006.01)
*C12N 5/10*    (2006.01)
*C12N 15/52*   (2006.01)
*A01H 5/00*    (2006.01)
*A01H 5/02*    (2006.01)
*A01H 5/10*    (2006.01)

(52) U.S. Cl. .................... 536/23.6; 435/320.1; 435/419; 800/323.1; 800/282; 536/23.2

(58) Field of Classification Search .................... 800/278
See application file for complete search history.

(56) References Cited

U.S. PATENT DOCUMENTS
6,774,285 B1 *   8/2004   Brugliera et al. ............. 800/298

OTHER PUBLICATIONS

Schlangen et al., Chalcone 3-hydroxylation is not a general property of flavonoid 3'-hydroxylase, 2009, Plant Science 177:97-102.*
Shimokoriyama, Masami, et al., "Anthochlor Pigments of Cosmos sulphureus, Coreopsis lanceolata and C. saxicola," *Journal of the American Chemical Society*, vol. 75, 1953: pp. 1900-1904.
Office Action issued by Japanese Patent Office in corresponding Application No. JP2009-298019 on Jul. 17, 2012 (English translation).

* cited by examiner

*Primary Examiner* — David T Fox
*Assistant Examiner* — Steven Bernacki
(74) *Attorney, Agent, or Firm* — Fulbright & Jaworski L.L.P.

(57) ABSTRACT

The present invention relates to an isolated nucleic acid molecule, comprising a nucleotide sequence, which encodes a polypeptide with chalcone 3-hydroxylase activity, wherein the nucleotide sequence comprises SEQ ID NO. 1 or has at least a 60% identity with SEQ ID NO. 1 or is able to hybridize with a molecule comprising the sequence of SEQ ID NO. 1, wherein the nucleotide sequence encodes a polypeptide, which comprises the motif FASRPLSX$_1$X$_2$G(X$_3$)$_m$(GSAGGD)$_n$ (SEQ ID NO. 3), wherein X$_1$ is threonine or serine, X$_2$ is alanine or glycine, X$_3$ is any amino acid, m is an integer between 50 and 200, and n is 0 or 1.

10 Claims, 5 Drawing Sheets

```
>CH3H       MTILPLLLYPSLTALLLYVLLNLRPRHPNRLPPGPSPWPIVGNLPHLGASPHQSLATLAAKYGPLMYLRL
>F3'H       MTILPLLLYPSLTALLLYVLLNLRPRHPNRLPPGPSPWPIVGNLPHLGTTPHHSLAALAAKYGPLMHLRL
Consensus   MTILPLLLYPSLTALLLYVLLNLRPRHPNRLPPGPSPWPIVGNLPHLGs*PHpSLAsLAAKYGPLMaLRL >CH3H       GFVDVVVAASASVAAQFLKVHDLNFASRFLSSGGKYIAYNYQDMVFAPYGPRWRMLRKICSVHMFSAKAM
>F3'H       GFVDVVVAASASVASQFLKTHDANFASRPPNSGAEHMAYNYQDLVFAPYGPRWRMLRKICSVHLFSGKAL
Consensus   GFVDVVVAASASVAtQFLKsHDhNFASRP.sSGtcabAYNYQDbVFAPYGPRWRMLRKICSVHbFStKAb >CH3H       DGFRHVRQEEVAILTRTLVSAGKSPVKLGQILNVCTTNALARVVLGRRVFADGSAGGDPKADEFKDMVVE
>F3'H       DDFRHVRQEEVAVLTRALAGAGKSPVKLGQLLSVCTTNALARVMLGRRVFGER————DAKADEFKDMVVE
Consensus   DsFRHVRQEEVAlLTRsLstAGKSPVKLGQlLsVCTTNALARVhLGRRVFt-.....DsKADEFKDMVVE
                                                                SAGG (+N)

>CH3H       LMVLAGEFHIGDFIPALDWLDLQGIKNKMKKLHARFDSFLHGILEEHKSGKFGAPSHGDLLSTLISLKDD
>F3'H       MMVLAGEFNIGDFIPALDWLDLQGITKKMKKLHAQFDSFLNTILEEHKTGKGGSSSHRDLSSTLIALKDD
Consensus   bMVLAGEFpIGDFIPALDWLDLQGIppKMKKLHApFDSFLpsILEEHK*GKhGtsSH.DL.STLItLKDD >CH3H       ADGEGGKLSDVEIKALLLNLFVAGTDTSSSTVEWAIAELIRHFKLLKQAQKEMDNVVGRDRLVTELDLNE
>F3'H       ADGEGGKLSDIEIKALLLNLFIAGTDTSSSTVEWAIAELIRCFQILRQAHEEMDNVVGRERLVTESDLGK
Consensus   ADGEGGKLSDlEIKALLLNLFlAGTDTSSSTVEWAIAELIRpPplL+QApcEMDNVVGR-RLVTE.DLsc >CH3H       LNFLQAIVKETFRLHPSTPLSLPRIASESCEVDGYYIPKGSTLLVNVWAIARDPNVWADPLEFREMRFLP
>F3'H       LTFLQAIVKETFRLHPSTPLSLPRIASESCEIDGYFIPKGSTLLVNVWAIARDPKMWTDPLEFRFTRFLP
Consensus,  LsFLQAIVKETFRLHPSTPLSLPRIASESCEIDGYaIPKGSTLLVNVWAIARDPphWsDPLEFRPhRFLP >CH3H       GGEKPNVDVQGNNFEVIPFGAGRRICVGISLGLRMVQLLVATLVQTFDWELANGLNPEKLNMDEAFGLTI
>F3'H       GGEKPNVDVKGNDFEVIPFGAGRRICVGISLGLRMVQLLVATLVQTFDWELANGVLPEKLNMNEAFGLTL
Consensus   GGEKPNVDVpGNsFEVIPFGAGRRICVGISLGLRMVQLLVATLVQTFDWELANGl.PEKLNMsEAFGLTL >CH3H       QKAEPLMVHPMPRLAPHVYGSH
>F3'H       QRAEPLIVPKPRLAPHVYESG
Consensus   Q+AEPLbVaPbPRLAPHVY.Sh
```

Fig. 1

| | SPS1 | SEQ ID | put. Loop region | SEQ ID | P450 Sample | SEQ ID |
|---|---|---|---|---|---|---|
| >C. sulphureus CH3H | SRPLSSGGKYIAYNYQDMVFAPY | 37 | RRVFADGSAGGDPKAD | 38 | DVQGNNFEVIPFGAGRRICVG | 39 |
| >Cosmos_sulphureus F3'H | SRPPNSGAEHMAYNYQDLVFAPY | 40 | RRVFGER----DAKAD | 41 | DVKGNNFEVIPFGAGRRICVG | 42 |
| >Dahlia_variabilis | SRPPNSGAKHIAYNYQDLVFAPY | 43 | RRVFGDT---GDLKAD | 44 | DVKGNDFEVIPFGAGRRICVG | 45 |
| >Targetes_erecta | SRPPNSGAKHIAYNYQDLVFAPY | 46 | RRVFGDT---GDLKAD | 47 | DVKGNDFEVIPFGAGRRICVG | 48 |
| >Rudbeckia_hirta | SRPPNSGAKHIAYNYQDLVFAPY | 49 | RRVFSDT----SDLKAD | 50 | DVKGNDFEVIPFGAGRRICVG | 51 |
| >Echinops_bannaticus | SRPPNSGAKHMAYNYQDMVFAPY | 52 | RRVFGDGSGGDSKSD | 53 | DVKGNDFELIPFGAGRRICAG | 54 |
| >Centaurea_cyanus | SRPPNSGAKHLAYDYQDLVFAPY | 55 | RRVFGDGSGGGDPKAD | 56 | NVKGNDFEIIPFGAGRRICAG | 57 |
| >Gerbera_hybrida | DRPPNSGAKHIAYNYQDLVFAPY | 58 | RRVEDS----GDAQAD | 59 | DIKGNDFEVIPFGAGRRICVG | 60 |
| >Osteospermum_hybrida | SRPPNSGAKHMAYNYQDLVFAPY | 61 | RRVFDS----GDAQAD | 62 | DIKGNDFEVIPFGAGRRICVG | 63 |
| >Cichorium_intybus | SRPPNSGAKHMAYNYQDLVFAPY | 64 | RRVFGDGSGGGDPKAD | 65 | DVKGNDFEVIPFGAGRRICAG | 66 |
| >Antirrhinum_majus | SRPPNSGAKHVAYNYQDLVFAPY | 67 | RRVVGH----ADSKAE | 68 | DVPGNDFELIPFGAGRRICAG | 69 |
| >Arabidopsis_thaliana | SRPPNSGAKHMAYNYQDLVFAPY | 70 | RRLFGAD---ADHKAD | 71 | DVKGSDFELIPFGAGRRICAG | 72 |
| Consensus/80% | SRPPNSGAKHbAYNYQDLVFAPY | | RRVFts....tD.KAD | | DVKGNDFElIPFGAGRRICsG | |

Fig. 2

| cDNA clone | Template | Manipulation | Forward Primer | SEQ ID NO | Reverse primer | SEQ ID NO |
|---|---|---|---|---|---|---|
| Chimeric genes | | ORF Region | | | | |
| C1 | 5'-Fragment F3'H | 1-196 | ATGACTATTCTACCCCTACTACTC | 9 | CTTCGCATTCACGCTCACCG | 11 |
| C2 | 3'-Fragment CH3H | 197-508 | P-GCGGATGAGTTCAAGGATATGG | 12 | CCTTAATGACTTCCATACAC GTG | 10 |
| | 5'-Fragment CH3H | 1-210 | ATGACTATTCTACCCCTACTACTC | 9 | CTTCGGATCACCACCTGCA | 13 |
| | 3'-Fragment F3'H | 211-512 | P-GCGGATGAGTTCAAG GAT ATG G | 12 | AGGATGTCTCAACTTACAACAATAAACC | 14 |
| | 5'-Fragment CH3H | 1-119 | ATGACTATTCTACCCCTACTACTC | 9 | GTACGGTGCAAAACACCATATC | 15 |
| | 3'-Fragment F3'H | 120-508 | P-GGTCCTCGGTGGCGGAT | 16 | AGGATGTCTCAACTTACAACAATAAACC | 14 |
| | 5'-Fragment F3'H | 1-193 | ATGACTATTCTACCCCTACTACTC | 9 | P-TTCGCATCTCGTGGC | 17 |
| | 3'-Fragment CH3H | 194-508 | GGCGGATGAGTTCAAGGATATG | 18 | AGGATGTCTCAACTTACAACAATAAACC | 14 |
| | 5'-Fragment CH3H | 1-119 | ATGACTATTCTACCCCTACTACTC | 9 | GTACGGTGCAAACACCATATC | 15 |
| | 3'-Fragment | 120-512 | P-GGTCCTCGGTGGCGGAT | 16 | AGGATGTCTCAACTTACAACAATAAACC | 14 |
| Mutated Genes | | Mutation | | | | |
| M1 | 5'-Fragment CH3H | Deletion of S(194)AAG(197) | ATGACTATTCTACCCCTACTACTC | 9 | TCCGTCGGCGAATACTCTC | 19 |
| | 3'-Fragment CH3H | | P-GATCCGAAGGCGGATGAGTT | 20 | CCTTAATGACTTCCATACAC GTG | 10 |
| M2 | 5'-Fragment F3'H | Insertion of S(194)AAG(197), Substitution of R(193) in G and A(199) in P | ATGACTATTCTACCCCTACTACTC | 9 | CACCTGCACTTCCGTCACGAATACTCTCCT GCC (SAGG from CH3H) | 21 |
| | 3'-Fragment | | P-GTGATGCGAAGGCGGATGAG | 22 | AGGATGTCTCAACTTACAACAATAAACC | 14 |
| M3 | CH3H | CCG -> GCG P(199) -> A | | | ATCCGCCTTCGCATCACCA | 23 |

Fig. 5

SEQUENCE LISTING

```
<160> NUMBER OF SEQ ID NOS: 84

<210> SEQ ID NO 1
<211> LENGTH: 1539
<212> TYPE: DNA
<213> ORGANISM: Cosmos sulphureus

<400> SEQUENCE: 1
atgactattc taccoctact actctaccct tccctaactg ccttactact gtacgtactt      60
cttaacctgc gcccccgtca ccctaaccgt ctcccgccgg gaccaagccc atggccgatc     120
gtcggaaacc taccgcacct cggcgcgagt ccgcatcagt cgctggcgac gttggccgca     180
aagtacggcc cgttgatgta cctccgactc gggtttgttg acgtggtggt ggcggcgtct     240
gcttcagtcg ctgcacagtt tttaaaagtt catgatctta acttcgcaag ccggccgctg     300
agctctggcg ggaagtatat cgcgtataat tatcaggata tggtgtttgc accgtacggt     360
ccgagatggc ggatgcttag gaagatttgc tccgtgcata tgttttctgc taaagcaatg     420
gacggatttc gtcatgttcg gcaggaggaa gtagctatac tcacgcgcac tttagtaagc     480
gctggaaaat cgccggtgaa gttaggtcaa atacttaacg tgtgcaccac gaacgcatta     540
gcacgagtgg tgttaggtcg gagagtattc gccgacggaa gtgcaggtgg tgatccgaag     600
gcggatgagt tcaaggatat ggtggtggag ctgatggtgt tggccggaga atttcacatc     660
ggtgacttta tcccggcgct tgactggctg gacctgcaag gcattaaaaa caagatgaag     720
aaacttcacg ctcgattcga ttcgttcctt cacgggatcc ttgaagagca taagtccggc     780
aagtttggcg cgccgagtca tggtgatttg ttgagcacat tgatctcgtt gaaggatgat     840
gccgatggtg aaggcgggaa gctttcagat gttgaaatca aagctttgct tctgaactta     900
```

-continued

```
tttgtcgccg aacagacac atcatcaagt acagtggaat gggcaatagc cgagctaatt    960
cgacatccaa agctactaaa acaagcccaa aagaaatgg acaatgtagt tggtcgagac   1020
cggcttgtaa ctgaattaga cttaaacgag ttaaattttc tacaagccat tgtaaaagag   1080
acctttaggc ttcacccttc aacaccactc tcgttaccaa gaattgcatc agagagttgt   1140
gaagttgacg atattacat tcccaaggga tccacgctcc ttgttaatgt gtgggccatt   1200
gctcgtgacc cgaatgtgtg ggctgaccca cttgaattcc ggcccatgcg gttcttgcct   1260
ggaggcgaaa agcctaatgt tgatgttcaa ggaaacaact ttgaagttat accgtttggg   1320
gctgggcgaa ggatttgtgt gggtattagt ctagggttga aatggtcca gctacttgtt   1380 gcaacattgg ttcaaacctt tgattgggaa ttggctaatg ggttaaaccc ggagaagcta   1440
aacatggatg aagcctttgg gttaaccctt cagaaggctg agcccttgat ggtgcaccca   1500
atgccgagac tagctccaca cgtgtatgga agtcattaa                          1539
```

<210> SEQ ID NO 2
<211> LENGTH: 512
<212> TYPE: PRT
<213> ORGANISM: Cosmos sulphureus

<400> SEQUENCE: 2

```
Met Thr Ile Leu Pro Leu Leu Tyr Pro Ser Leu Thr Ala Leu Leu
1               5                   10                  15

Leu Tyr Val Leu Leu Asn Leu Arg Pro Arg His Pro Asn Arg Leu Pro
            20                  25                  30

Pro Gly Pro Ser Pro Trp Pro Ile Val Gly Asn Leu Pro His Leu Gly
        35                  40                  45

Ala Ser Pro His Gln Ser Leu Ala Thr Leu Ala Ala Lys Tyr Gly Pro
    50                  55                  60

Leu Met Tyr Leu Arg Leu Gly Phe Val Asp Val Val Ala Ala Ser
65                  70                  75                  80

Ala Ser Val Ala Ala Gln Phe Leu Lys Val His Asp Leu Asn Phe Ala
                85                  90                  95

Ser Arg Pro Leu Ser Ser Gly Gly Lys Tyr Ile Ala Tyr Asn Tyr Gln
            100                 105                 110

Asp Met Val Phe Ala Pro Tyr Gly Pro Arg Trp Arg Met Leu Arg Lys
        115                 120                 125

Ile Cys Ser Val His Met Phe Ser Ala Lys Ala Met Asp Gly Phe Arg
    130                 135                 140

His Val Arg Gln Glu Glu Val Ala Ile Leu Thr Arg Thr Leu Val Ser
145                 150                 155                 160

Ala Gly Lys Ser Pro Val Lys Leu Gly Gln Ile Leu Asn Val Cys Thr
                165                 170                 175

Thr Asn Ala Leu Ala Arg Val Val Leu Gly Arg Arg Val Phe Ala Asp
            180                 185                 190

Gly Ser Ala Gly Gly Asp Pro Lys Ala Asp Glu Phe Lys Asp Met Val
        195                 200                 205

Val Glu Leu Met Val Leu Ala Gly Glu Phe His Ile Gly Asp Phe Ile
    210                 215                 220

Pro Ala Leu Asp Trp Leu Asp Leu Gln Gly Ile Lys Asn Lys Met Lys
225                 230                 235                 240

Lys Leu His Ala Arg Phe Asp Ser Phe Leu Gly Ile Leu Glu Glu
                245                 250                 255

His Lys Ser Gly Lys Phe Gly Ala Pro Ser His Gly Asp Leu Leu Ser
            260                 265                 270
```

-continued

```
Thr Leu Ile Ser Leu Lys Asp Asp Ala Asp Gly Glu Gly Gly Lys Leu
        275                 280                 285
Ser Asp Val Glu Ile Lys Ala Leu Leu Leu Asn Leu Phe Val Ala Gly
        290                 295                 300
Thr Asp Thr Ser Ser Ser Thr Val Glu Trp Ala Ile Ala Glu Leu Ile
305                 310                 315                 320
Arg His Pro Lys Leu Leu Lys Gln Ala Gln Lys Glu Met Asp Asn Val
                325                 330                 335
Val Gly Arg Asp Arg Leu Val Thr Glu Leu Asp Leu Asn Glu Leu Asn
                340                 345                 350
Phe Leu Gln Ala Ile Val Lys Glu Thr Phe Arg Leu His Pro Ser Thr
        355                 360                 365
Pro Leu Ser Leu Pro Arg Ile Ala Ser Glu Ser Cys Glu Val Asp Gly
        370                 375                 380
Tyr Tyr Ile Pro Lys Gly Ser Thr Leu Leu Val Asn Val Trp Ala Ile
385                 390                 395                 400
Ala Arg Asp Pro Asn Val Trp Ala Asp Pro Leu Glu Phe Arg Pro Met
                405                 410                 415
Arg Phe Leu Pro Gly Gly Glu Lys Pro Asn Val Asp Val Gln Gly Asn
                420                 425                 430
Asn Phe Glu Val Ile Pro Phe Gly Ala Gly Arg Arg Ile Cys Val Gly
        435                 440                 445
Ile Ser Leu Gly Leu Arg Met Val Gln Leu Leu Val Ala Thr Leu Val
        450                 455                 460
Gln Thr Phe Asp Trp Glu Leu Ala Asn Gly Leu Asn Pro Glu Lys Leu
465                 470                 475                 480
Asn Met Asp Glu Ala Phe Gly Leu Thr Leu Gln Lys Ala Glu Pro Leu
                485                 490                 495
Met Val His Pro Met Pro Arg Leu Ala Pro His Val Tyr Gly Ser His
                500                 505                 510

<210> SEQ ID NO 3
<211> LENGTH: 216
<212> TYPE: PRT
<213> ORGANISM: Artificial Sequence
<220> FEATURE:
<223> OTHER INFORMATION: Synthetic motif
<220> FEATURE:
<221> NAME/KEY: MISC_FEATURE
<222> LOCATION: (8)..(8)
<223> OTHER INFORMATION: Xaa = T or S
<220> FEATURE:
<221> NAME/KEY: MISC_FEATURE
<222> LOCATION: (9)..(9)
<223> OTHER INFORMATION: Xaa = A or G
<220> FEATURE:
<221> NAME/KEY: MISC_FEATURE
<222> LOCATION: (11)..(210)
<223> OTHER INFORMATION: Xaa = (Xaa)m wherein Xaa is any amino acid
      residue and m an integer between 50 and 200
<220> FEATURE:
<221> NAME/KEY: MISC_FEATURE
<222> LOCATION: (211)..(216)
<223> OTHER INFORMATION: Xaa = (GSAGGD)n wherein n is 0 or 1: the amino
      acids are either present or can be missing
<220> FEATURE:
<221> NAME/KEY: MISC_FEATURE
<222> LOCATION: (211)..(216)
<223> OTHER INFORMATION: (GSAGGD)n wherein n is 0 or 1: the amino acids
      are either present or can be missing

<400> SEQUENCE: 3

Phe Ala Ser Arg Pro Leu Ser Xaa Xaa Gly Xaa Xaa Xaa Xaa Xaa Xaa
```

```
                  1               5                  10                 15
Xaa Xaa Xaa Xaa Xaa Xaa Xaa Xaa Xaa Xaa Xaa Xaa Xaa Xaa Xaa
                 20                 25                 30

Xaa Xaa Xaa Xaa Xaa Xaa Xaa Xaa Xaa Xaa Xaa Xaa Xaa Xaa Xaa
                 35                 40                 45

Xaa Xaa Xaa Xaa Xaa Xaa Xaa Xaa Xaa Xaa Xaa Xaa Xaa Xaa Xaa
 50                 55                 60

Xaa Xaa Xaa Xaa Xaa Xaa Xaa Xaa Xaa Xaa Xaa Xaa Xaa Xaa Xaa
 65                 70                 75                 80

Xaa Xaa Xaa Xaa Xaa Xaa Xaa Xaa Xaa Xaa Xaa Xaa Xaa Xaa Xaa
                 85                 90                 95

Xaa Xaa Xaa Xaa Xaa Xaa Xaa Xaa Xaa Xaa Xaa Xaa Xaa Xaa Xaa
                100                105                110

Xaa Xaa Xaa Xaa Xaa Xaa Xaa Xaa Xaa Xaa Xaa Xaa Xaa Xaa Xaa
                115                120                125

Xaa Xaa Xaa Xaa Xaa Xaa Xaa Xaa Xaa Xaa Xaa Xaa Xaa Xaa Xaa
                130                135                140

Xaa Xaa Xaa Xaa Xaa Xaa Xaa Xaa Xaa Xaa Xaa Xaa Xaa Xaa Xaa
145                150                155                160

Xaa Xaa Xaa Xaa Xaa Xaa Xaa Xaa Xaa Xaa Xaa Xaa Xaa Xaa Xaa
                165                170                175

Xaa Xaa Xaa Xaa Xaa Xaa Xaa Xaa Xaa Xaa Xaa Xaa Xaa Xaa Xaa
                180                185                190

Xaa Xaa Xaa Xaa Xaa Xaa Xaa Xaa Xaa Xaa Xaa Xaa Xaa Xaa Xaa
                195                200                205

Xaa Xaa Gly Ser Ala Gly Gly Asp
    210                 215

<210> SEQ ID NO 4
<211> LENGTH: 216
<212> TYPE: PRT
<213> ORGANISM: Artificial Sequence
<220> FEATURE:
<223> OTHER INFORMATION: Synthetic motif
<220> FEATURE:
<221> NAME/KEY: MISC_FEATURE
<222> LOCATION: (11)..(210)
<223> OTHER INFORMATION: Xaa = (Xaa)m wherein Xaa is any amino acid
      residue and m an integer between 50 and 200
<220> FEATURE:
<221> NAME/KEY: MISC_FEATURE
<222> LOCATION: (211)..(216)
<223> OTHER INFORMATION: Xaa = (GSAGGD)n wherein n is 0 or 1: the amino
      acids are either present or can be missing
<220> FEATURE:
<221> NAME/KEY: MISC_FEATURE
<222> LOCATION: (211)..(216)
<223> OTHER INFORMATION: (GSAGGD)n wherein n is 0 or 1: the amino acids
      are either present or can be missing

<400> SEQUENCE: 4

Phe Ala Ser Arg Pro Leu Ser Thr Ala Gly Xaa Xaa Xaa Xaa Xaa
  1               5                  10                 15

Xaa Xaa Xaa Xaa Xaa Xaa Xaa Xaa Xaa Xaa Xaa Xaa Xaa Xaa Xaa
                 20                 25                 30

Xaa Xaa Xaa Xaa Xaa Xaa Xaa Xaa Xaa Xaa Xaa Xaa Xaa Xaa Xaa
                 35                 40                 45

Xaa Xaa Xaa Xaa Xaa Xaa Xaa Xaa Xaa Xaa Xaa Xaa Xaa Xaa Xaa
 50                 55                 60

Xaa Xaa Xaa Xaa Xaa Xaa Xaa Xaa Xaa Xaa Xaa Xaa Xaa Xaa Xaa
 65                 70                 75                 80
```

Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa
        195                 200                 205

Xaa Xaa Gly Ser Ala Gly Gly Asp
    210                 215

<210> SEQ ID NO 5
<211> LENGTH: 216
<212> TYPE: PRT
<213> ORGANISM: Artificial Sequence
<220> FEATURE:
<223> OTHER INFORMATION: Synthetic motif
<220> FEATURE:
<221> NAME/KEY: MISC_FEATURE
<222> LOCATION: (11)..(210)
<223> OTHER INFORMATION: Xaa = (Xaa)m wherein Xaa is any amino acid
      residue and m an integer between 50 and 200
<220> FEATURE:
<221> NAME/KEY: MISC_FEATURE
<222> LOCATION: (211)..(216)
<223> OTHER INFORMATION: Xaa = (GSAGGD)n wherein n is 0 or 1: the amino
      acids are either present or can be missing
<220> FEATURE:
<221> NAME/KEY: MISC_FEATURE
<222> LOCATION: (211)..(216)
<223> OTHER INFORMATION: (GSAGGD)n wherein n is 0 or 1: the amino acids
      are either present or can be missing

<400> SEQUENCE: 5

Phe Ala Ser Arg Pro Leu Ser Ser Gly Gly Xaa Xaa Xaa Xaa Xaa
1               5                   10                  15

Xaa Xaa Xaa Xaa Xaa Xaa Xaa Xaa Xaa Xaa Xaa Xaa Xaa Xaa
         20                  25                  30

Xaa Xaa Xaa Xaa Xaa Xaa Xaa Xaa Xaa Xaa Xaa Xaa Xaa Xaa
     35                  40                  45

Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa Xaa Xaa
         100                 105                 110

Xaa Xaa Xaa Xaa Xaa Xaa Xaa Xaa Xaa Xaa Xaa Xaa Xaa Xaa
     115                 120                 125

Xaa Xaa Xaa Xaa Xaa Xaa Xaa Xaa Xaa Xaa Xaa Xaa Xaa Xaa
 130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa Xaa
    195                 200                 205

Xaa Xaa Gly Ser Ala Gly Gly Asp
    210                 215

```
<210> SEQ ID NO 6
<211> LENGTH: 38
<212> TYPE: DNA
<213> ORGANISM: Artificial Sequence
<220> FEATURE:
<223> OTHER INFORMATION: Primer

<400> SEQUENCE: 6
gaccacgcgt atcgatgtcg actttttttt tttttttt                              38

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
tggmgdatgc tkmggaaarat ytg                                             23

<210> SEQ ID NO 8
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (12)..(12)
<223> OTHER INFORMATION: n is a, c, g, or t

<400> SEQUENCE: 8
gcccattcma yngtrctaga tga                                              23

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
atgactattc taccctact actc                                              24

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
ccttaatgac ttccatacac gtg                                              23
```

```
<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
cttcgcatca cgctcaccg                                                    19

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
gcggatgagt tcaaggatat gg                                                22

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
cttcggatca ccacctgca                                                    19

<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14
aggatgtctc aacttacaac aataaacc                                          28

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gtacggtgca aacaccatat c                                                 21

<210> SEQ ID NO 16
<211> LENGTH: 17
<212> TYPE: DNA
<213> ORGANISM: Artificial Sequence
<220> FEATURE:
<223> OTHER INFORMATION: Primer

<400> SEQUENCE: 16
ggtcctcggt ggcggat                                                      17

<210> SEQ ID NO 17
<211> LENGTH: 17
<212> TYPE: DNA
<213> ORGANISM: Artificial Sequence
<220> FEATURE:
<223> OTHER INFORMATION: Primer#

<400> SEQUENCE: 17
```
ttcgcatctc cgtcggc                                                    17

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
ggcggatgag ttcaaggata tg                                              22

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
tccgtcggcg aatactctc                                                  19

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gatccgaagg cggatgagtt                                                 20

<210> SEQ ID NO 21
<211> LENGTH: 33
<212> TYPE: DNA
<213> ORGANISM: Artificial Sequence
<220> FEATURE:
<223> OTHER INFORMATION: Primer

<400> SEQUENCE: 21
cacctgcact tccgtcacga atactctcct gcc                                  33

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
gtgatgcgaa ggcggatgag                                                 20

<210> SEQ ID NO 23
<211> LENGTH: 19
<212> TYPE: DNA
<213> ORGANISM: Artificial Sequence
<220> FEATURE:
<223> OTHER INFORMATION: Primer

<400> SEQUENCE: 23
atccgccttc gcatcacca                                                  19

<210> SEQ ID NO 24
<211> LENGTH: 1602
<212> TYPE: PRT
<213> ORGANISM: Cosmos sulphureus

<400> SEQUENCE: 24

```
Ala Thr Gly Ala Cys Thr Ala Thr Thr Cys Thr Ala Cys Cys Cys Cys
1               5                   10                  15

Thr Ala Cys Thr Ala Cys Thr Cys Thr Ala Cys Cys Cys Thr Thr Cys
            20                  25                  30

Cys Cys Thr Ala Ala Cys Thr Gly Cys Cys Thr Thr Ala Cys Thr Ala
        35                  40                  45

Cys Thr Gly Thr Ala Cys Gly Thr Ala Cys Thr Thr Cys Thr Thr Ala
    50                  55                  60

Ala Cys Cys Thr Gly Cys Gly Cys Cys Cys Cys Cys Gly Thr Cys Ala
65                  70                  75                  80

Cys Cys Cys Thr Ala Ala Cys Cys Gly Thr Cys Thr Cys Cys Cys Gly
                85                  90                  95

Cys Cys Gly Gly Gly Ala Cys Cys Ala Ala Gly Cys Cys Cys Ala Thr
            100                 105                 110

Gly Gly Cys Cys Gly Ala Thr Cys Gly Thr Cys Gly Gly Ala Ala Ala
        115                 120                 125

Cys Cys Thr Ala Cys Cys Gly Cys Ala Cys Cys Thr Cys Gly Gly Cys
    130                 135                 140

Ala Cys Ala Ala Cys Thr Cys Cys Gly Cys Ala Thr Cys Ala Cys Thr
145                 150                 155                 160

Cys Gly Cys Thr Thr Gly Cys Gly Gly Cys Ala Thr Thr Gly Gly Cys
                165                 170                 175

Gly Gly Cys Ala Ala Ala Gly Thr Ala Cys Gly Gly Cys Cys Cys Gly
            180                 185                 190

Thr Thr Gly Ala Thr Gly Cys Ala Cys Cys Thr Cys Cys Gly Ala Cys
        195                 200                 205

Thr Cys Gly Gly Cys Thr Thr Thr Gly Thr Thr Gly Ala Cys Gly Thr
    210                 215                 220

Gly Gly Thr Gly Gly Thr Gly Gly Cys Cys Gly Cys Cys Thr Cys Thr
225                 230                 235                 240

Gly Cys Gly Thr Cys Ala Gly Thr Cys Gly Cys Thr Thr Cys Ala Cys
                245                 250                 255

Ala Gly Thr Thr Thr Thr Thr Gly Ala Ala Ala Ala Cys Thr Cys Ala
            260                 265                 270

Thr Gly Ala Cys Gly Cys Gly Ala Ala Thr Thr Thr Cys Gly Cys Cys
        275                 280                 285

Ala Gly Cys Cys Gly Gly Cys Cys Gly Cys Cys Gly Ala Ala Cys Thr
    290                 295                 300

Cys Cys Gly Gly Cys Gly Cys Gly Gly Ala Gly Cys Ala Thr Ala Thr
305                 310                 315                 320

Gly Gly Cys Gly Thr Ala Thr Ala Ala Thr Thr Ala Thr Cys Ala Gly
                325                 330                 335

Gly Ala Thr Cys Thr Gly Gly Thr Gly Thr Thr Thr Gly Cys Gly Cys
            340                 345                 350

Cys Gly Thr Ala Cys Gly Gly Thr Cys Cys Thr Cys Gly Gly Thr Gly
        355                 360                 365

Gly Cys Gly Gly Ala Thr Gly Cys Thr Thr Cys Gly Gly Ala Ala Gly
    370                 375                 380

Ala Thr Ala Thr Gly Cys Thr Cys Cys Gly Thr Gly Cys Ala Cys Cys
385                 390                 395                 400

Thr Ala Thr Thr Thr Thr Cys Cys Gly Gly Cys Ala Ala Ala Gly Cys
                405                 410                 415
```

```
Ala Cys Thr Cys Gly Ala Thr Gly Ala Cys Thr Thr Cys Cys Gly Thr
            420                 425                 430
Cys Ala Thr Gly Thr Thr Cys Gly Gly Cys Ala Gly Gly Ala Gly Gly
            435                 440                 445
Ala Ala Gly Thr Ala Gly Cys Gly Gly Thr Ala Cys Thr Gly Ala Cys
            450                 455                 460
Gly Cys Gly Cys Gly Cys Thr Thr Thr Ala Gly Cys Cys Gly Gly Thr
465                 470                 475                 480
Gly Cys Gly Gly Gly Gly Ala Ala Thr Cys Ala Cys Cys Gly Gly
            485                 490                 495
Thr Gly Ala Ala Ala Thr Thr Ala Gly Gly Thr Cys Ala Ala Cys Thr
            500                 505                 510
Gly Cys Thr Thr Ala Gly Cys Gly Thr Gly Thr Gly Cys Ala Cys Cys
            515                 520                 525
Ala Cys Cys Ala Ala Cys Gly Cys Ala Thr Ala Gly Cys Ala Cys
            530                 535                 540
Gly Ala Gly Thr Gly Ala Thr Gly Thr Thr Ala Gly Gly Cys Ala Gly
545                 550                 555                 560
Gly Ala Gly Ala Gly Thr Ala Thr Thr Cys Gly Gly Thr Gly Ala Gly
            565                 570                 575
Cys Gly Thr Gly Ala Thr Gly Cys Gly Ala Ala Gly Gly Cys Gly Gly
            580                 585                 590
Ala Thr Gly Ala Gly Thr Thr Cys Ala Ala Gly Gly Ala Thr Ala Thr
            595                 600                 605
Gly Gly Thr Gly Gly Thr Gly Gly Ala Gly Ala Thr Gly Ala Thr Gly
            610                 615                 620
Gly Thr Gly Thr Thr Gly Gly Cys Gly Gly Ala Gly Ala Ala Thr
625                 630                 635                 640
Thr Cys Ala Ala Thr Ala Thr Cys Gly Gly Thr Gly Ala Cys Thr Thr
            645                 650                 655
Thr Ala Thr Cys Cys Cys Gly Gly Cys Gly Gly Cys Thr Thr Gly Ala Cys
            660                 665                 670
Thr Gly Gly Cys Thr Gly Gly Ala Cys Cys Thr Gly Cys Ala Ala Gly
            675                 680                 685
Gly Cys Ala Thr Cys Ala Cys Gly Ala Ala Ala Ala Ala Ala Thr
            690                 695                 700
Gly Ala Ala Gly Ala Ala Gly Cys Thr Gly Cys Ala Cys Gly Cys Thr
705                 710                 715                 720
Cys Ala Ala Thr Thr Cys Gly Ala Thr Thr Cys Gly Thr Thr Thr Cys
            725                 730                 735
Thr Thr Ala Ala Cys Ala Cys Gly Ala Thr Thr Cys Thr Thr Gly Ala
            740                 745                 750
Ala Gly Ala Gly Cys Ala Thr Ala Ala Ala Cys Cys Gly Gly Cys
            755                 760                 765
Ala Ala Gly Gly Gly Cys Gly Gly Cys Thr Cys Thr Thr Cys Gly Ala
            770                 775                 780
Gly Thr Cys Ala Cys Ala Gly Gly Gly Ala Thr Thr Gly Thr Cys
785                 790                 795                 800
Gly Ala Gly Cys Ala Cys Gly Cys Thr Gly Ala Thr Gly Cys Ala
            805                 810                 815
Cys Thr Cys Ala Ala Gly Gly Ala Thr Gly Ala Thr Gly Cys Cys Gly
            820                 825                 830
Ala Thr Gly Gly Ala Gly Ala Gly Gly Gly Ala Gly Gly Gly Ala Ala
```

-continued

```
               835                 840                 845
Ala Cys Thr Thr Thr Cys Ala Gly Ala Thr Ala Thr Thr Gly Ala Ala
    850                 855                 860
Ala Thr Cys Ala Ala Ala Gly Cys Thr Thr Gly Cys Thr Thr Cys
865                 870                 875                 880
Thr Gly Ala Ala Cys Thr Thr Ala Thr Thr Cys Ala Thr Gly Cys
                    885                 890                 895
Gly Gly Gly Ala Ala Cys Ala Gly Ala Thr Ala Cys Ala Thr Cys Ala
            900                 905                 910
Thr Cys Thr Ala Gly Cys Ala Cys Gly Thr Gly Gly Ala Ala Thr
            915                 920                 925
Gly Gly Gly Cys Ala Ala Thr Ala Gly Cys Thr Gly Ala Ala Cys Thr
            930                 935                 940
Ala Ala Thr Thr Cys Gly Cys Thr Gly Thr Cys Ala Cys Ala Ala
945                 950                 955                 960
Ala Thr Ala Cys Thr Ala Cys Gly Gly Cys Ala Ala Gly Cys Ala Cys
                    965                 970                 975
Ala Cys Gly Ala Ala Gly Ala Ala Thr Gly Gly Ala Cys Ala Ala
            980                 985                 990
Thr Gly Thr Thr Gly Thr Thr Gly Gly Thr Gly Cys Gly Ala Gly Ala Gly
            995                 1000                1005
Cys Gly Gly Cys Thr Thr Gly Thr Ala Ala Cys Cys Gly Ala Ala
    1010                1015                1020
Thr Cys Ala Gly Ala Cys Cys Thr Thr Gly Gly Thr Ala Ala Ala
    1025                1030                1035
Cys Thr Ala Ala Cys Ala Thr Cys Cys Thr Cys Cys Ala Ala
    1040                1045                1050
Gly Cys Cys Ala Thr Thr Gly Thr Ala Ala Ala Gly Gly Ala Gly
    1055                1060                1065
Ala Cys Cys Thr Thr Thr Ala Gly Ala Cys Thr Cys Cys Ala Cys
    1070                1075                1080
Cys Cys Gly Thr Cys Thr Ala Cys Ala Cys Cys Ala Cys Thr Cys
    1085                1090                1095
Thr Cys Ala Thr Thr Gly Cys Cys Ala Ala Gly Ala Ala Thr Thr
    1100                1105                1110
Gly Cys Gly Thr Cys Cys Gly Ala Gly Ala Gly Thr Thr Gly Thr
    1115                1120                1125
Gly Ala Ala Ala Thr Thr Gly Ala Thr Gly Gly Cys Thr Ala Thr
    1130                1135                1140
Thr Thr Cys Ala Thr Thr Cys Cys Thr Ala Ala Gly Gly Gly Gly
    1145                1150                1155
Thr Cys Cys Ala Cys Ala Cys Thr Thr Cys Thr Thr Gly Thr Thr
    1160                1165                1170
Ala Ala Thr Gly Thr Gly Thr Gly Gly Cys Cys Ala Thr Thr
    1175                1180                1185
Gly Cys Cys Cys Gly Thr Gly Ala Cys Cys Cys Ala Ala Ala
    1190                1195                1200
Ala Thr Gly Thr Gly Gly Ala Cys Gly Gly Ala Thr Cys Cys Ala
    1205                1210                1215
Cys Thr Thr Gly Ala Ala Thr Thr Thr Ala Gly Gly Cys Cys Cys
    1220                1225                1230
Ala Cys Ala Cys Gly Gly Thr Thr Cys Thr Thr Gly Cys Cys Cys
    1235                1240                1245
```

Gly Gly Ala Gly Gly Thr Gly Ala Ala Ala Ala Cys Cys Cys
            1250                1255                1260

Ala Ala Thr Gly Thr Thr Gly Ala Thr Gly Thr Ala Ala Ala
    1265                1270                1275

Gly Gly Ala Ala Ala Thr Gly Ala Cys Thr Thr Cys Gly Ala Gly
    1280                1285                1290

Gly Thr Thr Ala Thr Ala Cys Cys Ala Thr Thr Gly Gly Gly
    1295                1300                1305

Gly Cys Cys Gly Gly Ala Cys Gly Ala Ala Gly Ala Thr Thr
    1310                1315                1320

Thr Gly Thr Gly Thr Gly Gly Gly Thr Ala Thr Ala Gly Cys
    1325                1330                1335

Cys Thr Ala Gly Gly Gly Thr Thr Gly Ala Gly Ala Ala Thr Gly
    1340                1345                1350

Gly Thr Cys Cys Ala Gly Thr Thr Gly Cys Thr Thr Gly Thr Cys
    1355                1360                1365

Gly Cys Thr Ala Cys Gly Cys Thr Ala Gly Thr Cys Cys Ala Ala
    1370                1375                1380

Ala Cys Cys Thr Thr Thr Gly Ala Cys Thr Gly Gly Gly Ala Ala
    1385                1390                1395

Thr Thr Gly Gly Cys Thr Ala Ala Cys Gly Gly Gly Thr Ala
    1400                1405                1410

Cys Thr Ala Cys Cys Cys Gly Ala Gly Ala Ala Gly Cys Thr Cys
    1415                1420                1425

Ala Ala Cys Ala Thr Gly Ala Ala Thr Gly Ala Ala Gly Cys Gly
    1430                1435                1440

Thr Thr Thr Gly Gly Gly Cys Thr Ala Ala Cys Cys Cys Thr Thr
    1445                1450                1455

Cys Ala Ala Ala Gly Ala Gly Cys Cys Gly Ala Gly Cys Cys Cys
    1460                1465                1470

Thr Thr Gly Ala Thr Ala Gly Thr Gly Thr Ala Cys Cys Cys Gly
    1475                1480                1485

Ala Ala Gly Cys Cys Gly Ala Gly Gly Cys Thr Ala Gly Cys Thr
    1490                1495                1500

Cys Cys Thr Cys Ala Cys Gly Thr Ala Thr Ala Thr Gly Ala Ala
    1505                1510                1515

Ala Gly Thr Gly Gly Thr Thr Ala Ala Gly Gly Ala Cys Thr Ala
    1520                1525                1530

Ala Ala Thr Thr Thr Cys Cys Gly Thr Thr Thr Gly Ala Ala Ala
    1535                1540                1545

Ala Thr Thr Ala Ala Ala Thr Ala Ala Ala Thr Thr Gly Thr
    1550                1555                1560

Ala Thr Thr Thr Cys Thr Gly Thr Thr Thr Thr Gly Gly Thr Thr
    1565                1570                1575

Thr Ala Thr Thr Gly Thr Thr Gly Thr Ala Ala Gly Thr Thr Gly
    1580                1585                1590

Ala Gly Ala Cys Ala Thr Cys Cys Thr
    1595                1600

<210> SEQ ID NO 25
<211> LENGTH: 1645
<212> TYPE: PRT
<213> ORGANISM: Dahlia variabilis

<400> SEQUENCE: 25

-continued

```
Ala Thr Gly Gly Cys Cys Ala Thr Thr Cys Thr Ala Ala Cys Cys Cys
1               5                   10                  15

Thr Ala Cys Thr Ala Cys Thr Thr Ala Cys Ala Cys Cys Thr Cys
            20                  25                  30

Cys Ala Thr Cys Ala Cys Thr Thr Cys Cys Cys Cys Gly Thr Gly
            35                  40                  45

Cys Thr Gly Thr Ala Cys Cys Thr Cys Cys Thr Gly Cys Thr Thr Ala
    50                  55                  60

Ala Cys Cys Thr Gly Cys Gly Cys Ala Cys Cys Cys Gly Thr Cys Ala
65                  70                  75                  80

Cys Cys Cys Thr Ala Ala Cys Cys Gly Thr Cys Thr Cys Cys Thr
            85                  90                  95

Cys Cys Cys Gly Gly Cys Cys Ala Ala Cys Cys Cys Ala Thr
            100                 105                 110

Gly Gly Cys Cys Gly Ala Thr Cys Gly Thr Cys Gly Gly Ala Ala Ala
            115                 120                 125

Cys Cys Thr Cys Cys Gly Cys Ala Cys Cys Thr Cys Gly Gly Cys
            130                 135                 140

Ala Cys Ala Ala Thr Thr Cys Cys G

```
Cys Ala Thr Ala Thr Cys Gly Ala Cys Ala Gly Gly Ala Gly Gly
            435                 440                 445

Ala Gly Gly Thr Gly Cys Gly Ala Thr Ala Cys Thr Cys Ala Cys
450                 455                 460

Ala Cys Gly Thr Gly Cys Thr Thr Thr Gly Ala Thr Cys Gly Cys
465                 470                 475                 480

Gly Cys Cys Gly Gly Ala Gly Ala Ala Thr Cys Ala Ala Cys Gly Gly
                485                 490                 495

Thr Gly Ala Ala Ala Cys Thr Ala Gly Gly Thr Cys Ala Ala Cys Thr
                500                 505                 510

Ala Cys Thr Cys Ala Ala Cys Gly Thr Gly Thr Cys Ala Cys Cys
            515                 520                 525

Ala Cys Ala Ala Ala Cys Gly Cys Ala Thr Thr Ala Gly Cys Gly Cys
            530                 535                 540

Gly Thr Gly Thr Gly Ala Thr Gly Thr Ala Gly Gly Thr Ala Gly
545                 550                 555                 560

Gly Ala Gly Ala Gly Thr Gly Thr Thr Cys Gly Gly Cys Gly Ala Cys
                565                 570                 575

Ala Cys Cys Gly Gly Thr Gly Ala Thr Cys Thr Ala Ala Gly Gly
            580                 585                 590

Cys Gly Gly Ala Thr Gly Ala Gly Thr Thr Ala Ala Ala Gly Ala
                595                 600                 605

Thr Ala Thr Gly Gly Thr Gly Gly Thr Thr Cys Ala Gly Cys Thr Gly
610                 615                 620

Ala Thr Gly Gly Thr Gly Thr Thr Gly Gly Cys Cys Gly Gly Ala Gly
625                 630                 635                 640

Ala Ala Thr Thr Thr Ala Ala Cys Ala Thr Gly Gly Thr G

-continued

```
    850                 855                 860

Gly Ala Ala Ala Thr Cys Ala Ala Ala Gly Cys Thr Thr Thr Gly Thr
865                 870                 875                 880

Thr Ala Cys Thr Gly Ala Ala Cys Thr Thr Ala Thr Thr Cys Gly Thr
                885                 890                 895

Thr Gly Cys Ala Gly Gly Ala Ala Cys Ala Gly Ala Cys Ala Cys Gly
            900                 905                 910

Thr Cys Ala Thr Cys Thr Ala Gly Cys Ala Cys Ala Gly Thr Gly Gly
        915                 920                 925

Ala Ala Thr Gly Gly Gly Cys Ala Ala Thr Ala Gly Cys Cys Gly Ala
    930                 935                 940

Ala Cys Thr Cys Ala Thr Thr Cys Gly Cys Cys Ala Thr Cys Cys Ala
945                 950                 955                 960

Cys Gly Ala Ala Thr Gly Cys Thr Ala Ala Ala Cys Ala Ala Gly
                965                 970                 975

Cys Cys Cys Ala Ala Gly Ala Ala Gly Ala Ala Ala Thr Gly Gly Ala
            980                 985                 990

Cys Ala Ala Cys Gly Thr Ala Gly  Thr Thr Gly Gly Cys  Cys Gly Ala
        995                 1000                1005

Gly Ala  Cys Cys Gly Gly Cys  Thr Thr Gly Thr Ala  Thr Cys Cys
    1010                1015                1020

Gly Ala  Ala Thr Cys Thr Gly  Ala Thr Cys Thr Cys  Ala Gly Cys
    1025                1030                1035

Cys Ala  Ala Cys Thr Ala Cys  Cys Ala Thr Thr Cys  Cys Thr Cys
    1040                1045                1050

Cys Ala  Ala Gly Cys Cys Ala  Thr Thr Gly Thr Ala  Ala Ala Gly
    1055                1060                1065

Gly Ala  Gly Ala Cys Cys Thr  Thr Thr Ala Gly Ala  Cys Thr Cys
    1070                1075                1080

Cys Ala  Cys Cys Cys Cys Thr  Cys Ala Ala Cys Ala  Cys Cys Cys
    1085                1090                1095

Cys Thr  Cys Thr Cys Cys Thr  Thr Gly Cys Cys Ala  Ala Gly Ala
    1100                1105                1110

Ala Thr  Cys Thr Cys Ala Thr  Cys Cys Gly Ala Gly  Ala Ala Thr
    1115                1120                1125

Thr Gly  Cys Gly Ala Ala Gly  Thr Thr Gly Ala Cys  Gly Gly Gly
    1130                1135                1140

Thr Ala  Thr Cys Ala Cys Ala  Thr Thr Cys Cys Ala  Ala Ala Ala
    1145                1150                1155

Gly Gly  Ala Thr Cys Cys Ala  Cys Ala Cys Thr Cys  Cys Thr Cys
    1160                1165                1170

Gly Thr  Cys Ala Ala Thr Gly  Thr Gly Thr Gly Gly  Gly Cys Cys
    1175                1180                1185

Ala Thr  Thr Gly Cys Thr Cys  Gly Thr Gly Ala Cys  Cys Cys Ala
    1190                1195                1200

Ala Ala  Gly Ala Thr Gly Thr  Gly Gly Gly Cys Gly  Gly Ala Cys
    1205                1210                1215

Cys Cys  Ala Cys Thr Thr Gly  Ala Gly Thr Thr Cys  Cys Gly Cys
    1220                1225                1230

Cys Cys  Cys Gly Cys Ala Cys  Gly Gly Thr Thr Cys  Thr Thr Gly
    1235                1240                1245

Cys Cys  Thr Gly Gly Ala Gly  Gly Cys Gly Ala Ala  Ala Ala Gly
    1250                1255                1260
```

```
Cys Cys Cys Ala Ala Thr Gly Thr Thr Gly Ala Thr Gly Thr Gly
        1265                1270                1275

Ala Ala Ala Gly Gly Gly Ala Ala Thr Gly Ala Thr Thr Thr Thr
        1280                1285                1290

Gly Ala Ala Gly Thr Thr Ala Thr Ala Cys Cys Gly Thr Thr Cys
        1295                1300                1305

Gly Gly Gly Gly Cys Thr Gly Ala Cys Gly Ala Ala Gly Gly
        1310                1315                1320

Ala Thr Thr Thr Gly Thr Gly Thr Gly Gly Gly Thr Ala Thr Thr
        1325                1330                1335

Ala Gly Cys Cys Thr Cys Gly Gly Gly Thr Thr Gly Ala Gly Gly
        1340                1345                1350

Ala Thr Gly Gly Thr Cys Cys Ala Gly Thr Thr Gly Cys Thr Thr
        1355                1360                1365

Gly Thr Thr Gly Cys Ala Ala Cys Gly Thr Cys Gly Gly Thr Cys
        1370                1375                1380

Cys Ala Gly Ala Cys Cys Thr Thr Cys Gly Ala Thr Thr Gly Gly
        1385                1390                1395

Gly Ala Ala Thr Thr Ala Gly Cys Thr Ala Ala Cys Gly Gly Gly
        1400                1405                1410

Thr Thr Ala Ala Ala Gly Cys Cys Gly Gly Ala Gly Ala Ala Gly
        1415                1420                1425

Cys Thr Cys Ala Ala Cys Ala Thr Gly Ala Ala Thr Gly Ala Ala
        1430                1435                1440

Gly Cys Thr Thr Ala Thr Gly Gly Gly Cys Thr Ala Ala Cys Cys
        1445                1450                1455

Cys Thr Thr Cys Ala Ala Gly Ala Gly Ala Ala Gly Ala Gly
        1460                1465                1470

Cys Cys Cys Thr Thr Gly Gly Thr Gly Gly Thr Gly Cys Ala Cys
        1475                1480                1485

Cys Cys Ala Ala Ala Gly Cys Cys Gly Ala Gly Gly Thr Thr Ala
        1490                1495                1500

Gly Cys Thr Cys Cys Thr Cys Ala Thr Gly Thr Ala Thr Ala Thr
        1505                1510                1515

Gly Ala Ala Ala Gly Thr Gly Gly Thr Thr Ala Ala Ala Gly Ala
        1520                1525                1530

Thr Thr Gly Ala Cys Thr Ala Gly Thr Gly Thr Cys Gly Thr
        1535                1540                1545

Thr Thr Gly Gly Ala Ala Ala Ala Thr Thr Gly Ala Thr Ala Gly
        1550                1555                1560

Cys Thr Thr Cys Ala Ala Thr Thr Ala Ala Ala Cys Ala Gly
        1565                1570                1575

Gly Thr Thr Ala Thr Gly Thr Thr Thr Gly Thr Thr Gly Thr Ala
        1580                1585                1590

Thr Cys Thr Ala Cys Gly Thr Thr Gly Thr Ala Cys Gly Thr Thr
        1595                1600                1605

Ala Ala Thr Thr Gly Thr Thr Thr Thr Ala Ala Gly Thr Thr Gly
        1610                1615                1620

Ala Gly Ala Ala Cys Ala Cys Cys Cys Ala Ala Thr Thr Thr Gly
        1625                1630                1635

Thr Ala Ala Thr Gly Gly Gly
        1640                1645

<210> SEQ ID NO 26
```

```
<211> LENGTH: 1700
<212> TYPE: PRT
<213> ORGANISM: Tagetes erecta

<400> SEQUENCE: 26

Ala Thr Gly Thr Cys Cys Ala Thr Thr Cys Thr Ala Ala Cys Cys Cys
1               5                   10                  15

Thr Ala Cys Thr Ala Cys Thr Thr Thr Ala Cys Ala Cys Cys Thr Cys
            20                  25                  30

Cys Ala Thr Cys Ala Cys Thr Thr Cys Cys Cys Cys Gly Thr Gly
        35                  40                  45

Cys Thr Gly Thr Ala Cys Cys Thr Cys Cys Thr Gly Cys Thr Thr Ala
50                  55                  60

Ala Cys Cys Thr Gly Cys Gly Cys Ala Cys Cys Gly Thr Cys Ala
65                  70                  75                  80

Cys Cys Cys Thr Ala Ala Cys Cys Gly Thr Cys Thr Cys Cys Cys Thr
            85                  90                  95

Cys Cys Cys Gly Gly Cys Cys Cys Ala Ala Cys Cys Cys Ala Thr
            100                 105                 110

Gly Gly Cys Cys Gly Ala Thr Cys Gly Thr Cys Gly Ala Ala Ala
            115                 120                 125

Cys Cys Thr Cys Cys Cys Gly Cys Ala Cys Cys Thr Cys Gly Gly Cys
            130                 135                 140

Ala Cys Ala Ala Thr Thr Cys Cys Gly Cys Ala Cys Cys Ala Cys Thr
145                 150                 155                 160

Cys Gly Cys Thr Ala Gly Cys Gly Cys Gly Gly Cys Thr Gly Gly Cys
            165                 170                 175

Gly Gly Thr Ala Ala Ala Gly Thr Ala Cys Gly Gly Cys Cys Cys Gly
            180                 185                 190

Thr Thr Gly Ala Thr Gly Cys Ala Cys Cys Thr Cys Cys Gly Cys Cys
            195                 200                 205

Thr Cys Gly Gly Cys Thr Thr Cys Gly Thr Thr Gly Ala Cys Gly Thr
            210                 215                 220

Gly Gly Thr Gly Gly Thr Cys Gly Cys Cys Gly Cys Cys Thr Cys Gly
225                 230                 235                 240

Gly Cys Gly Thr Cys Cys Gly Thr Cys Gly Cys Thr Gly Cys Thr Cys
            245                 250                 255

Ala Gly Thr Thr Thr Thr Thr Ala Ala Ala Ala Cys Thr Ala Ala
            260                 265                 270

Thr Gly Ala Cys Gly Cys Gly Ala Thr Thr Thr Cys Gly Cys Cys
            275                 280                 285

Ala Gly Cys Cys Gly Gly Cys Cys Gly Cys Gly Ala Ala Cys Thr
            290                 295                 300

Cys Cys Gly Gly Cys Gly Cys Gly Ala Ala Gly Cys Ala Thr Ala Thr
305                 310                 315                 320

Cys Gly Cys Gly Thr Ala Thr Ala Ala Cys Thr Ala Cys Cys Ala Gly
            325                 330                 335

Gly Ala Thr Cys Thr Gly Thr Gly Thr Thr Gly Cys Ala Cys
            340                 345                 350

Cys Gly Thr Ala Cys Gly Gly Thr Cys Cys Gly Cys Gly Gly Thr Gly
            355                 360                 365

Gly Cys Gly Gly Ala Thr Gly Cys Thr Gly Cys Gly Gly Ala Ala Gly
            370                 375                 380

Ala Thr Cys Thr Gly Cys Thr Cys Gly Gly Thr Gly Cys Ala Cys Cys
385                 390                 395                 400
```

Thr Thr Thr Thr Cys Thr Cys Cys Gly Cys Cys Ala Ala Ala Gly Cys
405 410 415

Cys Cys Thr Cys Gly Ala Thr Gly Ala Thr Thr Thr Cys Cys Gly Thr
420 425 430

Cys Ala Thr Ala Thr Thr Cys Gly Ala Cys Ala Gly Gly Ala Gly Gly
435 440 445

Ala Gly Gly Thr Gly Gly Cys Gly Ala Thr Ala Cys Thr Cys Ala Cys
450 455 460

Ala Cys Gly Thr Gly Cys Thr Thr Thr Gly Ala Thr Cys Gly Gly Cys
465 470 475 480

Gly Cys Cys Gly Gly Ala Gly Ala Ala Thr Cys Ala Ala Cys Gly Gly
485 490 495

Thr Gly Ala Ala Ala Cys Thr Ala Gly Gly Thr Cys Ala Ala Cys Thr
500 505 510

Ala Cys Thr Cys Ala Ala Cys Gly Thr Gly Thr Gly Cys Ala Cys Cys
515 520 525

Ala Cys Ala Ala Ala Cys Gly Cys Ala Thr Thr Ala Gly Cys Gly Cys
530 535 540

Gly Thr Gly Thr Gly Ala Thr Gly Thr Thr Ala Gly Gly Thr Ala Gly
545 550 555 560

Gly Ala Gly Ala Gly Thr Gly Thr Thr Cys Gly Gly Cys Gly Ala Cys
565 570 575

Ala Cys Cys Gly Gly Thr Gly Ala Thr Cys Thr Ala Ala Ala Gly Gly
580 585 590

Cys Gly Gly Ala Thr Gly Ala Gly Thr Thr Thr Ala Ala Ala Gly Ala
595 600 605

Thr Ala Thr Gly Gly Thr Gly Gly Thr Thr Cys Ala Gly Cys Thr Gly
610 615 620

Ala Thr Gly Gly Thr Gly Thr Thr Gly Gly Cys Cys Gly Gly Ala Gly
625 630 635 640

Ala Ala Thr Thr Thr Ala Ala Cys Ala Thr Thr Gly Gly Thr Gly Ala
645 650 655

Cys Thr Thr Thr Ala Thr Cys Cys Cys Gly Gly Cys Gly Cys Thr Thr
660 665 670

Gly Ala Cys Thr Gly Gly Cys Thr Gly Gly Ala Cys Ala Thr Gly Cys
675 680 685

Ala Ala Gly Gly Cys Ala Thr Thr Ala Cys Gly Ala Ala Gly Ala Ala
690 695 700

Gly Ala Thr Gly Ala Ala Gly Ala Ala Ala Cys Thr Cys Cys Ala Thr
705 710 715 720

Gly Cys Thr Cys Ala Ala Thr Thr Thr Gly Ala Thr Thr Cys Gly Thr
725 730 735

Thr Cys Cys Thr Thr Ala Ala Cys Gly Cys Gly Ala Thr Thr Cys Thr
740 745 750

Thr Gly Ala Ala Gly Ala Ala Cys Ala Thr Ala Ala Ala Thr Cys Cys
755 760 765

Cys Gly Gly Cys Ala Thr Gly Gly Cys Cys Gly Cys Ala Cys Gly Thr
770 775 780

Cys Gly Gly Gly Thr Cys Ala Cys Gly Gly Thr Gly Ala Cys Thr Thr
785 790 795 800

Gly Cys Thr Gly Ala Gly Cys Ala Cys Gly Cys Thr Gly Ala Thr Cys
805 810 815

Gly Cys Ala Cys Thr Cys Ala Ala Gly Gly Ala Thr Gly Ala Thr Gly

```
                820            825            830
Cys Thr Gly Ala Cys Gly Gly Thr Gly Ala Gly Gly Thr Gly Gly
        835            840            845
Gly Ala Ala Ala Cys Thr Thr Thr Cys Ala Gly Ala Thr Ala Thr
850            855            860
Gly Ala Ala Thr Cys Ala Ala Gly Cys Thr Thr Gly Thr
865            870            875            880
Thr Ala Cys Thr Gly Ala Ala Cys Thr Thr Ala Thr Cys Gly Thr
        885            890            895
Thr Gly Cys Ala Gly Gly Ala Cys Ala Gly Ala Cys Ala Cys Gly
        900            905            910
Thr Cys Ala Thr Cys Thr Ala Gly Cys Ala Cys Ala Gly Thr Gly
        915            920            925
Ala Ala Thr Gly Gly Gly Cys Ala Ala Thr Ala Gly Cys Cys Gly Ala
        930            935            940
Ala Cys Thr Cys Ala Thr Thr Cys Gly Cys Ala Thr Cys Cys Ala
945            950            955            960
Cys Gly Ala Ala Thr Gly Cys Thr Ala Ala Ala Cys Ala Ala Gly
        965            970            975
Cys Cys Cys Ala Ala Gly Ala Ala Gly Ala Ala Thr Gly Gly Ala
        980            985            990
Cys Ala Ala Cys Gly Thr Ala Gly  Thr Thr Gly Gly Cys  Cys Gly Ala
        995            1000           1005
Gly Ala  Cys Cys Gly Gly Cys  Thr Thr Gly Thr Ala  Thr Cys Cys
        1010           1015           1020
Gly Ala  Ala Thr Cys Thr Gly  Ala Thr Cys Thr Cys  Ala Gly Cys
        1025           1030           1035
Cys Ala  Ala Cys Thr Ala Cys  Cys Ala Thr Thr Cys  Cys Thr Cys
        1040           1045           1050
Cys Ala  Ala Gly Cys Cys Ala  Thr Thr Gly Thr Ala  Ala Ala Gly
        1055           1060           1065
Gly Ala  Gly Ala Cys Cys Thr  Thr Thr Ala Gly Ala  Cys Thr Cys
        1070           1075           1080
Cys Ala  Cys Cys Cys Thr  Cys Ala Ala Cys Ala  Cys Cys Cys
        1085           1090           1095
Cys Thr  Cys Thr Cys Cys Thr  Thr Gly Cys Cys Ala  Ala Gly Ala
        1100           1105           1110
Ala Thr  Cys Thr Cys Ala Thr  Cys Cys Gly Ala Gly  Ala Ala Thr
        1115           1120           1125
Thr Gly  Cys Gly Ala Ala Gly  Thr Thr Gly Ala Cys  Gly Gly Gly
        1130           1135           1140
Thr Ala  Thr Cys Ala Cys Ala  Thr Thr Cys Cys Ala  Ala Ala Ala
        1145           1150           1155
Gly Gly  Ala Thr Cys Cys Ala  Cys Ala Cys Thr Cys  Cys Thr Cys
        1160           1165           1170
Gly Thr  Cys Ala Ala Thr Gly  Thr Gly Thr Gly Gly  Gly Cys Cys
        1175           1180           1185
Ala Thr  Thr Gly Cys Thr Cys  Gly Thr Gly Ala Cys  Cys Cys Ala
        1190           1195           1200
Ala Ala  Gly Ala Thr Gly Thr  Gly Gly Gly Cys Gly  Gly Ala Cys
        1205           1210           1215
Cys Cys  Ala Cys Thr Thr Gly  Ala Gly Thr Cys  Cys Gly Cys
        1220           1225           1230
```

```
Cys Cys Cys Ala Cys Ala Cys Gly Gly Thr Thr Cys Thr Thr Gly
1235                1240                1245

Cys Cys Thr Gly Gly Ala Gly Gly Cys Gly Ala Ala Ala Ala Gly
1250                1255                1260

Cys Cys Cys Ala Ala Thr Gly Thr Thr Gly Ala Thr Gly Thr Gly
1265                1270                1275

Ala Ala Ala Gly Gly Gly Ala Ala Thr Gly Ala Thr Thr Thr Thr
1280                1285                1290

Gly Ala Ala Gly Thr Thr Ala Thr Ala Cys Cys Gly Thr Thr Cys
1295                1300                1305

Gly Gly Gly Gly Cys Thr Gly Gly Gly Cys Gly Ala Ala Gly Gly
1310                1315                1320

Ala Thr Thr Thr Gly Thr Gly Thr Gly Gly Gly Thr Ala Thr Thr
1325                1330                1335

Ala Gly Cys Cys Thr Cys Gly Gly Thr Thr Gly Ala Gly Gly
1340                1345                1350

Ala Thr Gly Gly Thr Cys Cys Ala Gly Thr Thr Gly Cys Thr Thr
1355                1360                1365

Gly Thr Thr Gly Cys Ala Ala Cys Gly Thr Thr Gly Gly Thr Cys
1370                1375                1380

Cys Ala Gly Ala Cys Cys Thr Thr Cys Gly Ala Thr Thr Gly Gly
1385                1390                1395

Gly Ala Ala Thr Thr Ala Gly Cys Thr Ala Ala Cys Gly Gly Gly
1400                1405                1410

Thr Thr Ala Ala Ala Gly Cys Cys Gly Gly Ala Gly Ala Ala Gly
1415                1420                1425

Cys Thr Cys Ala Ala Cys Ala Thr Gly Ala Ala Thr Gly Ala Ala
1430                1435                1440

Gly Cys Thr Thr Ala Thr Gly Gly Gly Cys Thr Ala Ala Cys Cys
1445                1450                1455

Cys Thr Thr Cys Ala Ala Ala Gly Ala Gly Ala Ala Gly Ala Gly
1460                1465                1470

Cys Cys Cys Thr Thr Gly Gly Thr Gly Gly Thr Gly Cys Ala Cys
1475                1480                1485

Cys Cys Ala Ala Ala Gly Cys Gly Ala Gly Gly Thr Thr Ala
1490                1495                1500

Gly Cys Thr Cys Cys Thr Cys Ala Thr Gly Thr Ala Thr Ala Thr
1505                1510                1515

Gly Ala Ala Ala Gly Thr Gly Gly Thr Thr Ala Ala Ala Gly Ala
1520                1525                1530

Thr Thr Gly Ala Cys Thr Ala Gly Thr Thr Gly Thr Cys Gly Thr
1535                1540                1545

Thr Thr Gly Gly Ala Ala Ala Ala Thr Thr Gly Ala Thr Ala Ala
1550                1555                1560

Cys Thr Thr Thr Cys Ala Ala Thr Thr Ala Ala Ala Cys Ala Gly
1565                1570                1575

Gly Thr Thr Ala Thr Gly Thr Thr Thr Gly Thr Thr Gly Thr Ala
1580                1585                1590

Thr Cys Thr Ala Cys Gly Thr Gly Thr Ala Cys Gly Thr Thr
1595                1600                1605

Ala Ala Thr Thr Gly Thr Thr Thr Thr Ala Ala Gly Thr Thr Gly
1610                1615                1620

Ala Gly Ala Ala Cys Ala Cys Cys Cys Ala Ala Thr Thr Thr Gly
1625                1630                1635
```

Gly Gly Ala Thr Gly Gly Thr Thr Ala Thr Ala Thr
       1640            1645            1650

Thr Cys Gly Thr Thr Ala Ala Gly Thr Thr Ala Ala Thr Ala Ala
       1655            1660            1665

Thr Ala Ala Ala Ala Thr Ala Ala Ala Thr Ala Thr Thr Gly Cys
       1670            1675            1680

Ala Thr Ala Ala Ala Ala Ala Ala Ala Ala Ala Ala Ala Ala Ala
       1685            1690            1695

Ala Ala
       1700

<210> SEQ ID NO 27
<211> LENGTH: 1625
<212> TYPE: PRT
<213> ORGANISM: Rudbeckia hirta

<400> SEQUENCE: 27

Ala Thr Gly Gly Cys Cys Ala Thr Thr Cys Thr Ala Ala Cys Cys
 1               5                  10                 15

Thr Ala Cys Thr Ala Cys Thr Thr Thr Ala Cys Ala Cys Thr Cys
            20                  25                 30

Cys Ala Thr Cys Ala Cys Thr Thr Cys Cys Cys Thr Cys Gly Thr Gly
            35                  40                 45

Cys Thr Gly Thr Ala Cys Cys Thr Cys Thr Gly Cys Thr Thr Ala
        50                  55                 60

Ala Cys Cys Thr Gly Cys Gly Cys Ala Cys Cys Cys Gly Thr Cys Ala
65                  70                  75                 80

Cys Cys Cys Thr Ala Ala Cys Cys Gly Thr Cys Thr Cys Cys Cys Ala
            85                  90                 95

Cys Cys Cys Gly Gly Cys Cys Ala Ala Cys Cys Cys Ala Thr
            100                 105                110

Gly Gly Cys Cys Gly Ala Thr Cys Gly Thr Cys Gly Gly Ala Ala Ala
            115                 120                125

Cys Cys Thr Cys Cys Gly Cys Ala Cys Cys Thr Cys Gly Gly Thr
            130                 135                140

Ala Cys Ala Ala Thr Thr Cys Cys Ala Cys Cys Ala Cys Thr
145                 150                 155                160

Cys Gly Cys Thr Ala Gly Cys Gly Cys Gly Gly Thr Thr Gly Gly Cys
            165                 170                175

Cys Gly Cys Ala Ala Ala Gly Thr Ala Cys Gly Gly Cys Cys Gly
            180                 185                190

Thr Thr Gly Ala Thr Gly Cys Ala Cys Cys Thr Cys Cys Gly Cys Cys
            195                 200                205

Thr Cys Gly Gly Cys Thr Thr Cys Gly Thr Thr Gly Ala Cys Gly Thr
            210                 215                220

Gly Gly Thr Gly Gly Thr Cys Gly Cys Cys Thr Cys Gly
225                 230                 235                240

Gly Cys Gly Thr Cys Cys Gly Thr Cys Gly Thr Gly Cys Thr Cys
            245                 250                255

Ala Gly Thr Thr Thr Thr Thr Gly Ala Ala Ala Ala Cys Thr Ala Ala
            260                 265                270

Thr Gly Ala Cys Gly Cys Gly Ala Thr Thr Thr Thr Cys Gly Cys Cys
        275                 280                285

Ala Gly Cys Cys Gly Gly Cys Cys Gly Cys Gly Ala Ala Cys Thr
            290                 295                300

```
Cys Cys Gly Gly Cys Gly Gly Ala Ala Gly Cys Ala Thr Ala Thr
305                 310                 315                 320

Cys Gly Cys Gly Thr Ala Thr Ala Ala Cys Thr Ala Cys Cys Ala Gly
            325                 330                 335

Gly Ala Thr Cys Thr Gly Gly Thr Gly Thr Thr Thr Gly Cys Ala Cys
                340                 345                 350

Cys Ala Thr Ala Cys Gly Gly Thr Cys Cys Gly Cys Gly Gly Thr Gly
            355                 360                 365

Gly Cys Gly Gly Ala Thr Gly Cys Thr Gly Cys Gly Gly Ala Ala Gly
    370                 375                 380

Ala Thr Cys Thr Gly Cys Thr Cys Gly Gly Thr Gly Cys Ala Cys Cys
385                 390                 395                 400

Thr Thr Thr Thr Cys Thr Cys Cys Gly Cys Cys Ala Ala Gly Cys
                405                 410                 415

Ala Cys Thr Cys Gly Ala Thr Gly Ala Thr Thr Thr Cys Cys Gly Thr
    420                 425                 430

Cys Ala Thr Ala Thr Thr Cys Gly Ala Cys Ala Gly Gly Ala Gly Gly
        435                 440                 445

Ala Gly Gly Thr Gly Gly Cys Gly Ala Thr Ala Thr Cys Ala Cys
450                 455                 460

Ala Cys Gly Thr Gly Cys Thr Thr Thr Gly Ala Thr Cys Gly Gly Cys
465                 470                 475                 480

Gly Cys Cys Gly Gly Ala Gly Ala Ala Thr Cys Ala Ala Cys Gly Gly
            485                 490                 495

Thr Gly Ala Ala Ala Cys Thr Ala Gly Gly Thr Cys Ala Ala Cys Thr
    500                 505                 510

Ala Cys Thr Cys Ala Ala Cys Gly Thr Gly Thr Cys Ala Cys Cys
    515                 520                 525

Ala Cys Ala Ala Ala Cys Gly Cys Ala Thr Thr Ala Gly Cys Gly Cys
    530                 535                 540

Gly Thr Gly Thr Gly Ala Thr Gly Thr Thr Ala Gly Gly Cys Ala Gly
545                 550                 555                 560

Gly Ala Gly Ala Gly Thr Gly Thr Thr Cys Ala Gly Cys Gly Ala Cys
            565                 570                 575

Ala Cys Cys Gly Gly Thr Gly Ala Thr Cys Thr Ala Ala Ala Gly Gly
    580                 585                 590

Cys Gly Gly Ala Thr Gly Ala Gly Thr Thr Ala Ala Ala Gly Ala
        595                 600                 605

Thr Ala Thr Gly Gly Thr Gly Gly Thr Thr Cys Ala Gly Cys Thr Gly
610                 615                 620

Ala Thr Gly Gly Thr Gly Thr Thr Gly Gly Cys Cys Gly Gly Ala Gly
625                 630                 635                 640

Ala Ala Thr Thr Thr Ala Ala Cys Ala Thr Gly Gly Thr Gly Ala
        645                 650                 655

Cys Th

-continued

```
                725                 730                 735
Thr Cys Cys Thr Thr Ala Ala Cys Gly Cys Gly Ala Cys Cys Thr
            740                 745                 750
Thr Gly Ala Ala Gly Ala Ala Cys Ala Thr Ala Ala Thr Cys Cys
            755                 760                 765
Gly Gly Cys Ala Ala Thr Gly Gly Cys Cys Gly Cys Ala Cys Gly Thr
            770                 775                 780
Cys Gly Gly Gly Thr Cys Ala Cys Gly Gly Thr Gly Ala Cys Thr Thr
785                 790                 795                 800
Gly Cys Thr Gly Ala Gly Cys Ala Cys Gly Cys Thr Gly Ala Thr Cys
                805                 810                 815
Gly Cys Ala Cys Thr Cys Ala Ala Gly Gly Ala Thr Gly Ala Thr Gly
                820                 825                 830
Cys Thr Gly Ala Cys Gly Gly Thr Gly Ala Gly Gly Thr Gly Gly
            835                 840                 845
Gly Ala Ala Ala Cys Thr Thr Thr Cys Ala Gly Ala Thr Ala Thr Thr
850                 855                 860
Gly Ala Ala Thr Cys Ala Ala Gly Cys Thr Thr Thr Gly Cys
865                 870                 875                 880
Thr Ala Cys Thr Gly Ala Ala Cys Thr Thr Ala Thr Thr Cys Gly Thr
            885                 890                 895
Thr Gly Cys Ala Gly Gly Ala Ala Cys Ala Gly Ala Cys Ala Cys

-continued

Thr Ala Thr Cys Ala Cys Ala Thr Thr Cys Cys Ala Ala Ala
1145                1150                1155

Gly Gly Ala Thr Cys Cys Ala Cys Ala Cys Thr Cys Thr Thr
1160                1165                1170

Gly Thr Cys Ala Ala Cys Gly Thr Gly Thr Gly Gly Cys Cys
1175                1180                1185

Ala Thr Thr Gly Cys Thr Cys Gly Thr Gly Ala Cys Cys Cys Ala
1190                1195                1200

Ala Ala Gly Ala Thr Gly Thr Gly Gly Cys Gly Gly Ala Cys
1205                1210                1215

Cys Cys Ala Cys Thr Thr Gly Ala Gly Thr Cys Cys Gly Cys
1220                1225                1230

Cys Cys Cys Ala Cys Ala Cys Gly Gly Thr Thr Cys Thr Thr Gly
1235                1240                1245

Cys Cys Thr Gly Gly Ala Gly Gly Cys Gly Ala Ala Ala Gly
1250                1255                1260

Cys Cys Cys Ala Ala Thr Gly Thr Thr Gly Ala Thr Gly Thr Gly
1265                1270                1275

Ala Ala Ala Gly Gly Gly Ala Ala Thr Gly Ala Thr Thr Thr
1280                1285                1290

Gly Ala Ala Gly Thr Thr Ala Thr Ala Cys Cys Gly Thr Thr Cys
1295                1300                1305

Gly Gly Gly Gly Cys Thr Gly Gly Ala Cys Gly Ala Ala Gly Gly
1310                1315                1320

Ala Thr Thr Thr Gly Thr Gly Thr Gly Gly Gly Thr Ala Thr Thr
1325                1330                1335

Ala Gly Cys Cys Thr Cys Gly Gly Thr Thr Gly Ala Gly Gly
1340                1345                1350

Ala Thr Gly Gly Thr Cys Cys Ala Ala Thr Thr Gly Cys Thr Thr
1355                1360                1365

Gly Thr Thr Gly Cys Ala Ala Cys Gly Thr Thr Gly Gly Thr Cys
1370                1375                1380

Cys Ala Gly Ala Cys Cys Thr Thr Cys Gly Ala Thr Thr Gly Gly
1385                1390                1395

Gly Ala Ala Thr Thr Gly Gly Cys Thr Ala Ala Cys Gly Gly Gly
1400                1405                1410

Thr Thr Ala Gly Ala Gly Cys Cys Gly Gly Ala Gly Ala Ala Gly
1415                1420                1425

Cys Thr Cys Ala Ala Cys Ala Thr Gly Ala Ala Thr Gly Ala Ala
1430                1435                1440

Gly Cys Thr Thr Ala Thr Gly Gly Gly Cys Thr Ala Ala Cys Cys
1445                1450                1455

Cys Thr Thr Cys Ala Ala Gly Ala Gly Ala Ala Gly Ala Gly
1460                1465                1470

Cys Cys Cys Thr Thr Gly Ala Thr Gly Gly Thr Gly Cys Ala Cys
1475                1480                1485

Cys Cys Ala Ala Ala Gly Cys Cys Gly Ala Gly Gly Thr Thr Ala
1490                1495                1500

Gly Cys Thr Cys Cys Thr Cys Ala Thr Gly Thr Ala Thr Ala Thr
1505                1510                1515

Gly Ala Ala Ala Gly Thr Gly Gly Thr Thr Ala Ala Gly Gly Ala
1520                1525                1530

Cys Thr Gly Ala Cys Thr Ala Gly Thr Thr Gly Thr Cys Ala Cys
1535                1540                1545

```
Thr Thr Thr Cys Ala Ala Thr  Ala Ala Ala Cys  Ala Gly Gly
    1550             1555             1560

Thr Thr Gly Thr Thr Thr Gly  Cys Thr Gly Thr  Ala Thr Cys Thr
    1565             1570             1575

Ala Cys Gly Thr Thr Gly Thr  Ala Cys Gly Thr  Thr Ala Ala Thr
    1580             1585             1590

Thr Thr Gly Thr Ala Ala Gly  Thr Thr Gly Ala Gly  Ala Ala Cys
    1595             1600             1605

Ala Cys Cys Cys Ala Ala Thr  Thr Thr Gly Thr Ala  Ala Thr Gly
    1610             1615             1620

Gly Gly
    1625

<210> SEQ ID NO 28
<211> LENGTH: 1740
<212> TYPE: PRT
<213> ORGANISM: Echinops bannaticus

<400> SEQUENCE: 28

Cys Cys Thr Cys Cys Ala Ala Ala Cys Thr Cys Cys Ala Thr Ala Thr
1               5                   10                  15

Gly Thr Ala Ala Ala Thr Gly Ala Cys Cys Ala Thr Thr Cys Thr
            20                  25                  30

Ala Ala Cys Cys Thr Thr Cys Cys Thr Cys Thr Gly Thr Ala Cys
        35                  40                  45

Ala Cys Cys Thr Gly Cys Ala Thr Thr Ala Cys Thr Gly Gly Gly Thr
    50                  55                  60

Thr Ala Gly Thr Cys Thr Thr Cys Thr Ala Thr Gly Cys Ala Thr Thr
65                  70                  75                  80

Gly Cys Ala Cys Thr Thr Gly Thr Thr Thr Ala Ala Cys Cys Thr Gly
                85                  90                  95

Cys Gly Cys Ala Cys Ala Cys Cys Thr Cys Ala Cys Cys Gly Thr Ala
            100                 105                 110

Ala Cys Cys Gly Cys Cys Thr Cys Cys Cys Cys Cys Cys Gly Gly
        115                 120                 125

Cys Cys Cys Ala Ala Cys Ala Cys Cys Ala Thr Gly Gly Cys Cys Ala
    130                 135                 140

Ala Thr Cys Gly Thr Cys Gly Gly Cys Ala Ala Cys Thr Thr Ala Cys
145                 150                 155                 160

Cys Ala Cys Ala Thr Cys Thr Cys Gly Gly Cys Ala Gly Ala Gly Thr
                165                 170                 175

Thr Cys Cys Gly Cys Ala Cys Cys Ala Thr Cys Gly Cys Thr Gly
            180                 185                 190

Gly Cys Gly Gly Ala Cys Thr Thr Gly Gly Cys Gly Ala Cys Ala Ala
        195                 200                 205

Ala Gly Thr Ala Cys Gly Gly Cys Cys Gly Thr Thr Gly Cys Thr
    210                 215                 220

Gly Cys Ala Thr Cys Thr Cys Cys Gly Cys Thr Cys Gly Gly Ala
225                 230                 235                 240

Thr Thr Thr Gly Thr Thr Gly Ala Cys Gly Thr Gly Gly Thr Gly Gly
                245                 250                 255

Thr Gly Gly Cys Cys Gly Gly Ala Thr Cys Gly Gly Cys Thr Thr Cys
            260                 265                 270

Thr Gly Thr Cys Gly Cys Cys Gly Cys Ala Cys Ala Gly Thr Thr Thr
        275                 280                 285
```

-continued

```
Thr Thr Gly Ala Ala Gly Gly Thr Thr Cys Ala Thr Gly Ala Thr Gly
    290                 295                 300
Cys Gly Ala Ala Thr Thr Cys Gly Cys Thr Ala Gly Cys Ala Gly
305                 310                 315                 320
Gly Cys Cys Gly Cys Gly Ala Ala Cys Thr Cys Cys Gly Gly Ala
                325                 330                 335
Gly Cys Gly Ala Ala Gly Cys Ala Thr Ala Gly Gly Cys Gly Thr
                340                 345                 350
Ala Thr Ala Ala Thr Ala Thr Cys Ala Gly Gly Ala Thr Ala Thr
        355                 360                 365
Gly Gly Thr Gly Thr Thr Cys Gly Cys Ala Cys Cys Gly Thr Ala Cys
    370                 375                 380
Gly Gly Thr Cys Cys Gly Ala Ala Thr Gly Gly Cys Gly Gly Ala
385                 390                 395                 400
Thr Gly Cys Thr Thr Cys Gly Gly Ala Ala Gly Ala Thr Thr Gly
                405                 410                 415
Cys Thr Cys Gly Gly Thr Gly Cys Ala Cys Cys Thr Thr Thr Cys
                420                 425                 430
Thr Cys Thr Ala Cys Cys Ala Ala Gly Cys Ala Cys Thr Cys Gly
        435                 440                 445
Ala Thr Gly Ala Thr Thr Cys Cys Gly Thr Cys Ala Cys Gly Thr
    450                 455                 460
Thr Cys Gly Thr Cys Ala Gly Gly Ala Gly Gly Ala Gly Thr Ala
465                 470                 475                 480
Gly Cys Gly Ala Thr Ala Cys Thr Thr Gly Cys Thr Cys Gly Cys Gly
                485                 490                 495
Cys Thr Thr Thr Gly Gly Thr Cys Gly Gly Ala Gly Cys Cys Gly Gly
                500                 505                 510
Ala Gly Ala Ala Thr Cys Ala Ala Cys Gly Gly Thr Gly Ala Ala Ala
        515                 520                 525
Thr Thr Ala Gly Gly Thr Cys Ala Gly Thr Thr Ala Cys Thr Thr Ala
    530                 535                 540
Ala Cys Gly Thr Gly Thr Gly Cys Ala Cys Cys Ala Cys Ala Ala Ala
545                 550                 555                 560
Cys Gly Cys Gly Thr Thr Ala Gly Cys Ala Cys Gly Ala Gly Thr Thr
                565                 570                 575
Ala Thr Gly Thr Thr Ala Gly Gly Cys Ala Gly Gly Ala Gly Ala Gly
        580                 585                 590
Thr Gly Thr Thr Thr Gly Gly Cys Gly Ala Thr Gly Ala Ala Gly
    595                 600                 605
Thr Gly Gly Ala Gly Gly Cys Gly Gly Cys Gly Ala Thr Thr Cys Gly
    610                 615                 620
Ala Ala Gly Thr Cys Gly Gly Ala Thr Gly Ala Ala Thr Thr Ala
625                 630                 635                 640
Ala Gly Gly Ala Thr Ala Thr Gly Gly Thr Gly Ala Thr Gly Ala
                645                 650                 655
Gly Ala Thr Gly Ala Thr Gly Gly Thr Gly Thr Gly Gly Cys Cys
            660                 665                 670
Gly Gly Ala Gly Ala Ala Thr Cys Ala Ala Cys Ala Thr Cys Gly
        675                 680                 685
Gly Cys Gly Ala Cys Thr Thr Cys Ala Thr Cys Cys Gly Gly Cys
    690                 695                 700
Thr Cys Thr Gly Gly Ala Cys Thr Gly Gly Cys Thr Gly Gly Ala Cys
```

-continued

```
705                 710                 715                 720

Cys Thr Gly Cys Ala Ala Thr Cys Cys Gly Thr Gly Ala Cys Gly Ala
                725                 730                 735

Ala Ala Ala Ala Gly Ala Thr Gly Ala Ala Gly Ala Ala Ala Cys Thr
            740                 745                 750

Cys Cys Ala Thr Gly Thr Thr Cys Gly Gly Thr Thr Cys Gly Ala Thr
        755                 760                 765

Thr Cys Gly Thr Thr Cys Cys Thr Thr Ala Ala Thr Ala Cys Gly Ala
    770                 775                 780

Thr Cys Cys Thr Gly Gly Ala Ala Gly Ala Gly Cys Ala Thr Ala Ala
785                 790                 795                 800

Ala Ala Gly Thr Gly Gly Thr Ala Ala Thr Ala Thr Gly Gly Ala Thr
                805                 810                 815

Thr Thr Thr Gly Thr Gly Ala Gly Cys Ala Gly Gly Thr Thr Gly Ala
            820                 825                 830

Thr Thr Thr Cys Cys Gly Thr Cys Ala Ala Gly Gly Ala Thr Gly Ala
        835                 840                 845

Thr Gly Cys Ala Gly Ala Cys Gly Gly Ala Cys Ala Gly Gly Gly Ala
    850                 855                 860

Gly Gly Gly Ala Ala Gly Cys Thr Thr Thr Cys Ala Gly Ala Cys Ala
865                 870                 875                 880

Cys Cys Gly Ala Ala Ala Thr Cys Ala Ala Ala Gly Cys Thr Thr Thr
                885                 890                 895

Ala Cys Thr Thr Cys Thr Gly Ala Ala Thr Thr Thr Gly Thr Thr Thr
            900                 905                 910

Gly Cys Cys Gly Cys Gly Gly Gly Ala Ala Cys Ala Gly Ala Cys Ala
        915                 920                 925

Cys Ala Thr Cys Ala Thr Cys Thr Ala Gly Cys Ala Cys Thr Gly Thr
    930                 935                 940

Thr Gly Ala Ala Thr Gly Gly Gly Cys Ala Ala Thr Cys Gly Cys Cys
945                 950                 955                 960

Gly Ala Ala Cys Thr Cys Ala Thr Thr Cys Gly Ala Cys Ala Thr Cys
                965                 970                 975

Cys Ala Cys Ala Ala Cys Thr Ala Thr Thr Gly Ala Ala Gly Cys Ala
            980                 985                 990

Ala Gly Cys Cys Cys Ala Ala Gly  Ala Ala Gly Ala Ala  Ala Thr Gly
        995                 1000                1005

Gly Ala  Cys Ala Cys Cys Ala  Thr Ala Gly Thr Thr  Gly Gly Thr
    1010                1015                1020

Cys Gly  Ala Gly Ala Cys Cys  Gly Gly Cys Thr Ala  Gly Thr Thr
    1025                1030                1035

Ala Cys  Thr Gly Ala Ala Gly  Thr Gly Gly Ala Cys  Cys Thr Ala
    1040                1045                1050

Ala Gly  Thr Ala Gly Ala Cys  Thr Ala Ala Cys Ala  Thr Thr Cys
    1055                1060                1065

Cys Thr  Cys Cys Ala Ala Gly  Cys Cys Ala Thr Thr  Gly Thr Gly
    1070                1075                1080

Ala Ala  Gly Gly Ala Gly Ala  Thr Ala Thr Thr Thr  Ala Gly Gly
    1085                1090                1095

Cys Thr  Cys Cys Ala Thr Cys  Cys Gly Thr Cys Ala  Ala Cys Ala
    1100                1105                1110

Cys Cys  Ala Cys Thr Cys Thr  Cys Ala Thr Thr Gly  Cys Cys Ala
    1115                1120                1125
```

```
Ala Gly Gly Ala Thr Thr Gly Cys Ala Thr Cys Ala Gly Ala Cys
1130             1135                 1140

Ala Cys Thr Thr Gly Thr Gly Ala Gly Gly Thr Thr Gly Ala Cys
1145             1150                 1155

Gly Gly Ala Thr Ala Thr Thr Ala Thr Ala Thr Cys Cys Thr
1160             1165                 1170

Ala Ala Ala Gly Gly Ala Thr Cys Cys Ala Cys Gly Cys Thr Cys
1175             1180                 1185

Cys Thr Thr Gly Thr Thr Ala Ala Thr Gly Thr Thr Gly Gly
1190             1195                 1200

Gly Cys Cys Ala Thr Cys Thr Cys Thr Cys Gly Ala Gly Ala Cys
1205             1210                 1215

Cys Cys Ala Ala Ala Ala Ala Thr Ala Thr Gly Gly Thr Cys Cys
1220             1225                 1230

Ala Ala Thr Cys Cys Ala Cys Thr Thr Gly Ala Ala Thr Thr Cys
1235             1240                 1245

Cys Ala Ala Cys Cys Ala Cys Thr Cys Gly Ala Thr Thr Cys
1250             1255                 1260

Thr Thr Gly Cys Cys Thr Gly Gly Thr Gly Gly Thr Gly Ala Ala
1265             1270                 1275

Ala Ala Gly Cys Cys Ala Gly Ala Thr Gly Cys Cys Gly Ala Thr
1280             1285                 1290

Gly Thr Cys Ala Ala Gly Gly Gly Ala Ala Ala Thr Gly Ala Thr
1295             1300                 1305

Thr Thr Thr Gly Ala Gly Cys Thr Cys Ala Thr Ala Cys Cys Ala
1310             1315                 1320

Thr Thr Thr Gly Gly Gly Gly Cys Thr Gly Gly Ala Cys Gly Ala
1325             1330                 1335

Ala Gly Gly Ala Thr Thr Thr Gly Thr Gly Cys Ala Gly Gly Thr
1340             1345                 1350

Ala Thr Gly Ala Gly Thr Cys Thr Gly Gly Gly Ala Thr Thr Ala
1355             1360                 1365

Ala Ala Gly Ala Thr Gly Gly Thr Cys Cys Ala Gly Thr Thr Ala
1370             1375                 1380

Cys Thr Cys Ala Cys Thr Gly Cys Ala Ala Cys Thr Cys Thr Ala
1385             1390                 1395

Gly Thr Cys Cys Ala Thr Gly Cys Ala Thr Thr Cys Gly Ala Thr
1400             1405                 1410

Thr Gly Gly Gly Ala Ala Thr Thr Gly Gly Cys Thr Ala Ala Cys
1415             1420                 1425

Gly Gly Gly Thr Thr Ala Gly Ala Cys Cys Cys Ala Gly Ala Thr
1430             1435                 1440

Ala Ala Gly Cys Thr Cys Ala Ala Cys Ala Thr Gly Gly Ala Ala
1445             1450                 1455

Gly Ala Ala Gly Cys Cys Thr Ala Thr Gly Gly Gly Thr Thr Ala
1460             1465                 1470

Ala Cys Cys Cys Thr Cys Cys Ala Ala Ala Gly Gly Cys Thr
1475             1480                 1485

Ala Cys Ala Cys Cys Thr Thr Gly Ala Thr Gly Gly Thr Gly
1490             1495                 1500

Cys Ala Cys Cys Cys Ala Ala Gly Gly Cys Cys Ala Ala Gly Gly
1505             1510                 1515

Thr Thr Ala Gly Cys Cys Cys Cys Thr Cys Ala Thr Gly Thr Ala
1520             1525                 1530
```

```
Thr Ala  Cys Cys Ala Ala  Gly Thr Gly Thr  Thr Ala Ala
    1535             1540              1545

Gly Gly  Ala Cys Thr Thr  Ala Ala Cys Cys  Gly Thr Thr Ala
    1550             1555              1560

Thr Thr  Thr Ala Thr Thr  Cys Gly Cys Ala  Thr Thr Thr Thr
    1565             1570              1575

Gly Thr  Thr Thr Gly Cys  Gly Ala Ala Thr  Ala Ala Thr
    1580             1585              1590

Thr Ala  Ala Thr Cys Ala  Thr Ala Thr Thr  Thr Cys Thr Cys
    1595             1600              1605

Thr Ala  Gly Cys Gly Ala  Thr Thr Ala Thr  Gly Thr Ala Cys Gly
    1610             1615              1620

Thr Thr  Cys Thr Cys Thr  Ala Ala Ala Ala  Thr Gly Thr Thr
    1625             1630              1635

Thr Thr  Thr Thr Thr Thr  Ala Ala Thr Ala  Thr Cys Thr Thr
    1640             1645              1650

Ala Thr  Thr Cys Ala Thr  Gly Thr Ala Ala  Gly Thr Thr Gly Thr
    1655             1660              1665

Thr Thr  Cys Ala Thr Gly  Thr Thr Thr Thr Gly Gly  Cys Thr Ala
    1670             1675              1680

Ala Ala  Thr Ala Ala Ala  Thr Ala Ala Thr  Thr Ala Ala Ala
    1685             1690              1695

Thr Ala  Cys Thr Cys Ala  Thr Cys Thr Ala  Thr Cys Ala Thr Thr
    1700             1705              1710

Thr Cys  Thr Thr Thr Cys  Ala Ala Ala Ala  Ala Ala Ala Ala
    1715             1720              1725

Ala Ala  Ala Ala Ala Ala  Ala Ala Ala Ala  Ala
    1730             1735              1740

<210> SEQ ID NO 29
<211> LENGTH: 1578
<212> TYPE: PRT
<213> ORGANISM: Centaurea cyanus

<400> SEQUENCE: 29

Ala Thr Gly Ala Cys Ala Thr Thr Cys Thr Ala Cys Cys Cys Cys
1               5                   10                  15

Thr Gly Gly Thr Thr Cys Thr Ala Thr Cys Ala Cys Cys Thr Cys
                20                  25                  30

Thr Gly Thr Cys Gly Cys Cys Thr Gly Thr Thr Ala Cys Thr Cys
                35                  40                  45

Cys Thr Cys Thr Ala Cys Gly Thr Ala Thr Thr Gly Cys Thr Thr Ala
            50                  55                  60

Ala Cys Cys Thr Ala Cys Gly Cys Ala Cys Cys Cys Thr Cys Gly
65                  70                  75                  80

Cys Thr Cys Gly Ala Ala Cys Cys Gly Cys Gly Gly Cys Thr Thr
                85                  90                  95

Cys Cys Cys Cys Cys Cys Gly Gly Cys Cys Gly Ala Cys Cys Cys
                100                 105                 110

Cys Gly Thr Gly Gly Cys Cys Gly Ala Thr Ala Gly Thr Cys Gly Gly
            115                 120                 125

Ala Ala Ala Cys Thr Thr Gly Cys Cys Thr Ala Thr Cys Thr Cys
            130                 135                 140

Gly Gly Cys Ala Ala Gly Ala Thr Gly Cys Cys Thr Cys Ala Cys Cys
145                 150                 155                 160
```

-continued

```
Ala Thr Gly Cys Ala Thr Thr Gly Gly Cys Cys Gly Cys Ala Ala Thr
                165                 170                 175

Gly Gly Cys Gly Gly Ala Cys Ala Ala Gly Thr Ala Cys Gly Gly Cys
            180                 185                 190

Cys Cys Cys Thr Thr Gly Ala Thr Gly Cys Ala Thr Cys Thr Ala Cys
        195                 200                 205

Gly Gly Thr Thr Cys Gly Gly Cys Gly Thr Thr Gly Thr Gly Gly Ala
    210                 215                 220

Cys Gly Thr Cys Gly Thr Gly Gly Thr Gly Gly Cys Cys Gly Cys Gly
225                 230                 235                 240

Thr Cys Thr Gly Cys Thr Thr Cys Cys Gly Thr Gly Gly Cys Cys Gly
                245                 250                 255

Cys Thr Cys Ala Gly Thr Thr Thr Thr Thr Gly Ala Ala Gly Gly Thr
            260                 265                 270

Cys Cys Ala Cys Gly Ala Cys Gly Cys Gly Ala Ala Cys Thr Thr Cys
        275                 280                 285

Gly Cys Gly Ala Gly Cys Ala Gly Gly Cys Cys Gly Cys Cys Cys Ala
    290                 295                 300

Ala Cys Thr Cys Cys Gly Gly Gly Gly Cys Gly Ala Ala Gly Cys Ala
305                 310                 315                 320

Thr Cys Thr Cys Gly Cys Gly Thr Ala Cys Gly Ala Thr Thr Ala Thr
                325                 330                 335

Cys Ala Gly Gly Ala Thr Cys Thr Cys Gly Thr Gly Thr Thr Thr Gly
            340                 345                 350

Cys Cys Cys Cys Ala Thr Ala Cys Gly Gly Thr Cys Thr Gly Ala Ala
        355                 360                 365

Gly Thr Gly Gly Ala Gly Gly Ala Thr Gly Cys Thr Thr Cys Gly Gly
    370                 375                 380

Ala Ala Gly Ala Thr Cys Thr Gly Cys Thr Cys Gly Gly Thr Gly Cys
385                 390                 395                 400

Ala Thr Cys Thr Gly Thr Thr Cys Thr Cys Gly Ala Ala Thr Ala Ala
                405                 410                 415

Gly Gly Cys Ala Cys Thr Cys Gly Ala Thr Gly Ala Thr Thr Thr Cys
            420                 425                 430

Cys Gly Thr Cys Ala Cys Gly Thr Thr Cys Gly Thr Gly Ala Gly Gly
        435                 440                 445

Ala Gly Gly Ala Gly Gly Thr Gly Gly Cys Gly Gly Thr Thr Thr Thr
    450                 455                 460

Gly Ala Cys Cys Cys Gly Thr Gly Cys Thr Thr Thr Gly Gly Cys Cys
465                 470                 475                 480

Gly Gly Ala Gly Cys Cys Gly Gly Ala Gly Gly Ala Thr Cys Gly Ala
                485                 490                 495

Cys Gly Gly Thr Gly Gly Cys Thr Thr Thr Ala Gly Gly Thr Cys Ala
            500                 505                 510

Ala Thr Thr Ala Cys Thr Thr Ala Ala Cys Gly Thr Thr Thr Gly Cys
        515                 520                 525

Ala Cys Cys Ala Cys Ala Ala Ala Cys Gly Cys Thr Thr Thr Gly Gly
    530                 535                 540

Cys Ala Cys Gly Ala Gly Thr Gly Ala Thr Gly Thr Thr Ala Gly Gly
545                 550                 555                 560

Thr Ala Gly Gly Ala Gly Ala Gly Thr Ala Thr Thr Thr Gly Gly Thr
                565                 570                 575

Gly Ala Cys Gly Gly Thr Ala Gly Cys Gly Gly Ala Gly Gly Cys Gly
```

```
                  580                 585                 590
Gly Ala Gly Ala Thr Cys Gly Ala Gly Cys Gly Gly Ala
            595                 600                 605
Thr Gly Ala Ala Thr Thr Cys Ala Ala Gly Gly Ala Ala Ala Thr Gly
610                 615                 620
Gly Thr Gly Gly Thr Thr Gly Ala Ala Thr Gly Ala Thr Gly Gly
625                 630                 635                 640
Thr Ala Thr Thr Gly Gly Cys Cys Gly Ala Gly Ala Ala Thr Thr
            645                 650                 655
Cys Ala Ala Cys Ala Thr Cys Gly Gly Cys Gly Ala Cys Thr Thr Cys
            660                 665                 670
Ala Thr Thr Cys Cys Gly Gly Cys Gly Cys Thr Thr Gly Ala Thr
            675                 680                 685
Gly Gly Cys Thr Gly Gly Ala Cys Cys Thr Gly Cys Ala Ala Gly Gly
            690                 695                 700
Cys Gly Thr Ala Ala Cys Cys Ala Ala Ala Ala Ala Thr Gly
705                 710                 715                 720
Ala Ala Ala Ala Cys Cys Thr Cys Cys Ala Thr Cys Thr Cys Cys
            725                 730                 735
Gly Ala Thr Thr Thr Gly Ala Thr Thr Cys Gly Thr Thr Cys Thr
            740                 745                 750
Thr Ala Ala Cys Gly Ala Ala Ala Thr Cys Cys Thr Cys Gly Ala Ala
            755                 760                 765
Gly Ala Cys Cys Ala Thr Ala Ala Ala Ala Thr Gly Gly Cys Gly
            770                 775                 780
Gly Thr Gly Ala Cys Ala Thr Cys Ala Thr Cys Ala Cys Thr Cys
785                 790                 795                 800
Cys Gly Gly Thr Ala Ala Cys Gly Thr Gly Gly Ala Cys Thr Thr Gly
            805                 810                 815
Cys Thr Ala Ala Cys Cys Ala Cys Gly Thr Gly Ala Thr Thr Thr
            820                 825                 830
Cys Ala Cys Thr Cys Ala Ala Gly Gly Ala Cys Gly Ala Cys Gly Cys
            835                 840                 845
Cys Gly Ala Thr Gly Gly Gly Ala Gly Gly Thr Gly Gly Gly
            850                 855                 860
Ala Ala Gly Cys Thr Thr Thr Cys Ala Gly Ala Cys Ala Thr Cys Gly
865                 870                 875                 880
Ala Ala Ala Thr Cys Ala Ala Gly Cys Thr Ala Thr Ala Cys Thr
            885                 890                 895
Thr Cys Thr Gly Ala Ala Thr Thr Thr Ala Thr Thr Ala Cys Thr
            900                 905                 910
Gly Cys Thr Gly Gly Ala Ala Cys Ala Gly Ala Cys Ala Cys Gly Thr
            915                 920                 925
Cys Ala Thr Cys Thr Ala Gly Thr Ala Cys Gly Gly Thr Gly Gly Ala
            930                 935                 940
Ala Thr Gly Gly Gly Cys Ala Ala Thr Gly Gly Cys Ala Gly Ala Ala
945                 950                 955                 960
Cys Thr Thr Ala Thr Cys Gly Ala Thr Ala Thr Cys Cys Ala Cys
            965                 970                 975
Ala Ala Cys Thr Ala Ala Thr Gly Cys Ala Ala Ala Ala Gly Cys
            980                 985                 990
Cys Cys Ala Ala Gly Ala Ala Gly  Ala Ala Ala Thr Ala  Gly Ala Ala
            995                 1000                1005
```

-continued

Ala Gly Cys Gly Thr Ala Gly Thr Cys Gly Gly Thr Ala Gly Gly
1010             1015              1020

Gly Ala Cys Cys Gly Ala Cys Thr Thr Gly Thr Ala Thr Cys Thr
1025             1030              1035

Gly Ala Ala Thr Thr Gly Gly Ala Cys Cys Thr Ala Cys Cys Cys
1040             1045              1050

Cys Gly Ala Cys Thr Ala Ala Cys Gly Thr Thr Cys Cys Thr Thr
1055             1060              1065

Gly Ala Ala Gly Cys Cys Gly Thr Thr Gly Thr Gly Ala Ala Gly
1070             1075              1080

Gly Ala Ala Ala Cys Cys Thr Thr Thr Ala Gly Cys Thr Cys
1085             1090              1095

Cys Ala Cys Cys Cys Gly Thr Cys Gly Ala Cys Cys Cys Ala
1100             1105              1110

Cys Thr Ala Thr Cys Cys Thr Gly Cys Cys Thr Ala Gly Ala
1115             1120              1125

Ala Thr Gly Gly Cys Ala Thr Thr Ala Gly Ala Gly Ala Gly Thr
1130             1135              1140

Thr Gly Thr Gly Ala Ala Gly Thr Cys Gly Ala Thr Gly Gly Gly
1145             1150              1155

Thr Ala Thr Thr Ala Cys Ala Thr Thr Cys Cys Cys Ala Ala Ala
1160             1165              1170

Gly Gly Ala Thr Cys Cys Ala Cys Gly Cys Thr Thr Cys Thr Thr
1175             1180              1185

Gly Thr Thr Ala Ala Cys Gly Thr Gly Thr Gly Gly Gly Cys Cys
1190             1195              1200

Ala Thr Thr Gly Cys Thr Cys Gly Ala Gly Ala Cys Cys Cys Ala
1205             1210              1215

Ala Ala Ala Ala Thr Gly Thr Gly Gly Gly Ala Thr Gly Ala Cys
1220             1225              1230

Cys Cys Gly Cys Thr Thr Gly Ala Ala Thr Thr Cys Cys Gly Ala
1235             1240              1245

Cys Cys Thr Ala Gly Ala Cys Gly Ala Thr Thr Cys Thr Thr Gly
1250             1255              1260

Cys Cys Ala Ala Gly Ala Gly Gly Thr Gly Ala Ala Ala Ala Ala
1265             1270              1275

Cys Cys Gly Ala Ala Thr Gly Cys Thr Ala Ala Thr Gly Thr Gly
1280             1285              1290

Ala Ala Ala Gly Gly Ala Ala Ala Thr Gly Ala Thr Thr Thr Cys
1295             1300              1305

Gly Ala Ala Ala Thr Cys Ala Thr Ala Cys Cys Gly Thr Thr Thr
1310             1315              1320

Gly Gly Gly Gly Cys Thr Gly Gly Ala Cys Gly Ala Ala Gly Ala
1325             1330              1335

Ala Thr Thr Thr Gly Thr Gly Cys Ala Gly Gly Cys Ala Thr Gly
1340             1345              1350

Ala Gly Cys Cys Thr Ala Gly Gly Gly Thr Thr Ala Ala Gly Gly
1355             1360              1365

Ala Thr Gly Gly Thr Cys Cys Ala Gly Thr Thr Gly Cys Thr Cys
1370             1375              1380

Ala Cys Cys Gly Cys Gly Ala Cys Ala Cys Thr Gly Gly Thr Cys
1385             1390              1395

Cys Ala Thr Gly Cys Cys Thr Thr Thr Gly Ala Thr Thr Gly Gly
1400             1405              1410

-continued

```
Ala Ala Ala Thr Thr Gly Gly  Cys Thr Ala Ala  Thr Gly Gly Gly
    1415                1420                1425

Thr Thr Ala Gly Ala Cys Thr  Cys Ala Gly Ala  Gly Ala Ala Ala
    1430                1435                1440

Thr Thr Gly Ala Ala Cys Ala  Thr Gly Ala Ala  Ala Gly Ala Ala
    1445                1450                1455

Gly Cys Thr Thr Ala Thr Gly  Gly Gly Thr Thr  Ala Ala Cys Cys
    1460                1465                1470

Cys Thr Thr Cys Ala Ala Ala  Gly Gly Gly Ala  Thr Gly Thr Ala
    1475                1480                1485

Cys Cys Thr Thr Thr Gly Ala  Thr Gly Gly Thr  Ala Cys Ala Cys
    1490                1495                1500

Cys Cys Thr Ala Gly Cys Cys  Cys Ala Ala Gly  Gly Thr Thr Ala
    1505                1510                1515

Gly Cys Thr Cys Cys Cys Gly  Ala Gly Thr Thr  Ala Thr Ala Cys
    1520                1525                1530

Ala Ala Ala Ala Gly Thr Gly  Gly Thr Thr Ala  Ala Gly Gly Thr
    1535                1540                1545

Cys Thr Gly Ala Ala Ala Ala  Ala Ala Cys Cys  Ala Ala Thr Gly
    1550                1555                1560

Thr Ala Gly Thr Gly Gly Thr  Cys Thr Ala Thr  Ala Gly Cys Ala
    1565                1570                1575

<210> SEQ ID NO 30
<211> LENGTH: 1539
<212> TYPE: PRT
<213> ORGANISM: Gerbera hybrid cultivar D1

<400> SEQUENCE: 30

Ala Thr Gly Ala Cys Gly Cys  Thr Thr Ala Ala  Cys Gly Cys
1               5                 10                  15

Thr Cys Cys Thr Thr Ala Thr  Cys Gly Gly Cys  Ala Cys Thr Gly
    20                  25                  30

Thr Gly Thr Cys Ala Cys Thr  Gly Gly Ala Thr  Thr Ala Thr Cys
    35                  40                  45

Cys Thr Cys Thr Ala Cys Gly  Thr Gly Thr Thr  Gly Cys Thr Ala
    50                  55                  60

Ala Cys Cys Gly Gly Thr Gly  Cys Ala Cys Cys  Gly Thr Ala Ala
65                  70                  75                  80

Cys Cys Cys Thr Ala Ala Cys  Cys Gly Cys Cys  Thr Cys Cys Gly
            85                  90                  95

Cys Cys Cys Gly Gly Cys Cys  Cys Ala Ala Cys  Gly Cys Cys Ala Thr
            100                 105                 110

Gly Gly Cys Cys Gly Gly Thr  Cys Gly Thr Cys  Gly Ala Ala Ala
            115                 120                 125

Cys Cys Thr Ala Cys Cys Gly  Cys Ala Thr Cys  Thr Cys Gly Gly Cys
130                 135                 140

Ala Cys Thr Ala Thr Ala Cys  Cys Ala Cys Ala  Cys Ala Cys Thr
145                 150                 155                 160

Cys Gly Cys Thr Gly Gly Cys  Gly Gly Cys Gly  Ala Thr Gly Gly Cys
            165                 170                 175

Gly Ala Ala Gly Ala Ala Gly  Thr Ala Thr Gly  Gly Cys Cys Cys Gly
            180                 185                 190

Thr Thr Gly Ala Thr Gly Cys  Ala Cys Cys Thr  Cys Cys Gly Gly Cys
            195                 200                 205
```

```
Thr Ala Gly Gly Cys Thr Thr Cys Gly Thr Cys Gly Ala Cys Gly Thr
    210                 215                 220
Cys Gly Thr Gly Gly Thr Gly Gly Cys Cys Gly Cys Thr Cys Cys
225                 230                 235                 240
Gly Cys Cys Thr Cys Cys Gly Thr Cys Gly Cys Gly Cys Gly Cys
                245                 250                 255
Ala Gly Thr Thr Thr Thr Thr Gly Ala Ala Gly Ala Cys Thr Cys Ala
                260                 265                 270
Cys Gly Ala Cys Gly Cys Gly Ala Ala Cys Thr Thr Cys Gly Cys Cys
            275                 280                 285
Gly Ala Thr Cys Gly Gly Cys Cys Thr Cys Cys Gly Ala Ala Cys Thr
        290                 295                 300
Cys Cys Gly Gly Ala Gly Cys Ala Ala Gly Cys Ala Thr Ala Thr
305                 310                 315                 320
Cys Gly Cys Gly Thr Ala Thr Ala Ala Thr Ala Thr Cys Ala Gly
                325                 330                 335
Gly Ala Thr Cys Thr Gly Gly Thr Gly Thr Thr Thr Gly Cys Thr Cys
                340                 345                 350
Cys Gly Thr Ala Cys Gly Gly Thr Cys Cys Gly Cys Gly Gly Thr Gly
            355                 360                 365
Gly Cys Gly Gly Ala Thr Gly Cys Thr Thr Cys Gly Gly Ala Ala Gly
        370                 375                 380
Ala Thr Thr Thr Gly Cys Thr Cys Gly Gly Thr Gly Cys Ala Cys Cys
385                 390                 395                 400
Thr Gly Thr Thr Thr Thr Cys Cys Ala Cys Cys Ala Ala Ala Gly Cys
                405                 410                 415
Gly Cys Thr Cys Gly Ala Thr Gly Ala Thr Thr Cys Cys Gly Gly
                420                 425                 430
Cys Ala Cys Gly Thr Cys Cys Gly Gly Cys Ala Gly Gly Ala Gly Gly
            435                 440                 445
Ala Gly Gly Thr Ala Gly Cys Gly Ala Thr Ala Cys Thr Ala Gly Cys
        450                 455                 460
Gly Cys Gly Cys Gly Cys Thr Thr Thr Gly Gly Thr Cys Gly Gly Cys
465                 470                 475                 480
Gly Cys Cys Gly Gly Ala Ala Ala Ala Thr Cys Ala Cys Cys Gly Gly
                485                 490                 495
Thr Gly Ala Ala Ala Thr Thr Ala Gly Gly Thr Cys Ala Gly Thr Thr
                500                 505                 510
Ala Cys Thr Gly Ala Ala Cys Gly Thr Gly Thr Gly Cys Ala Cys Cys
            515                 520                 525
Ala Cys Ala Ala Ala Cys Gly Cys Ala Thr Thr Gly Gly Cys Gly Cys
        530                 535                 540
Gly Ala Gly Thr Gly Ala Thr Gly Thr Thr Ala Gly Gly Ala Gly
545                 550                 555                 560
Gly Ala Gly Ala Gly Thr Ala Thr Thr Thr Gly Ala Cys Thr Cys Cys
                565                 570                 575
Gly Gly Cys Gly Ala Thr Gly Cys Thr Cys Ala Gly Cys Gly Gly
                580                 585                 590
Ala Thr Gly Ala Gly Thr Cys Ala Ala Gly Ala Cys Ala Thr
            595                 600                 605
Gly Gly Thr Gly Thr Thr Gly Ala Gly Cys Thr Gly Ala Thr Gly
        610                 615                 620
Gly Thr Gly Thr Thr Ala Gly Cys Cys Gly Gly Ala Gly Ala Ala Thr
```

```
                625                 630                 635                 640
Thr Cys Ala Ala Cys Ala Thr Cys Gly Cys Gly Ala Cys Thr Thr
                    645                 650                 655
Cys Ala Thr Cys Cys Cys Gly Thr Gly Cys Thr Thr Gly Ala Cys
                    660                 665                 670
Thr Gly Gly Cys Thr Gly Gly Ala Cys Cys Thr Gly Cys Ala Ala Gly
                    675                 680                 685
Gly Cys Gly Thr Gly Ala Cys Gly Ala Ala Gly Ala Gly Ala Thr
                    690                 695                 700
Gly Ala Ala Gly Ala Ala Ala Cys Thr Cys Ala Cys Gly Cys Gly
705                 710                 715                 720
Ala Ala Ala Thr Thr Cys Gly Ala Cys Thr Cys Gly Thr Thr Cys Cys
                    725                 730                 735
Thr Thr Ala Ala Cys Ala Cys Gly Ala Thr Cys Cys Thr Cys Gly Ala
                    740                 745                 750
Ala Gly Ala Ala Cys Ala Thr Ala Ala Ala Cys Cys Gly Gly Cys
                    755                 760                 765
Gly Cys Cys Gly Gly Thr Gly Ala Cys Gly Gly Thr Gly Thr Cys Gly
            770                 775                 780
Cys Gly Thr Cys Gly Gly Thr Ala Ala Gly Thr Thr Gly Ala
785                 790                 795                 800
Cys Thr Thr Gly Thr Thr Gly Ala Gly Cys Ala Cys Gly Thr Thr Gly
                    805                 810                 815
Ala Thr Thr Thr Cys Gly Cys Thr Gly Ala Ala Gly Gly Ala Thr Gly
                    820                 825                 830
Ala Cys Gly Cys Ala Gly Ala Thr Gly Ala Gly Ala Gly Gly Gly
                    835                 840                 845
Ala Gly Gly Gly Ala Ala Gly Cys Thr Gly Thr Cys Gly Gly Ala Cys
850                 855                 860
Ala Thr Thr Gly Ala Ala Ala Thr Cys Ala Ala Ala Gly Cys Thr Thr
865                 870                 875                 880
Thr Gly Cys Thr Thr Cys Thr Gly Ala Ala Cys Thr Thr Ala Thr Thr
                    885                 890                 895
Cys Ala Cys Ala Gly Cys Gly Gly Gly Gly Ala Cys Thr Gly Ala Cys
                    900                 905                 910
Ala Cys Ala Thr Cys Ala Thr Cys Thr Ala Gly Thr Ala Cys Thr Ala
                    915                 920                 925
Thr Thr Gly Ala Ala Thr Gly Gly Gly Cys Thr Ala Thr Ala Gly Cys
                    930                 935                 940
Thr Gly Ala Ala Cys Thr Ala Ala Thr Thr Cys Gly Cys Ala Ala Cys
945                 950                 955                 960
Cys Cys Gly Cys Ala Ala Cys Thr Ala Thr Thr Gly Ala Ala Cys Cys
                    965                 970                 975
Ala Ala Gly Cys Cys Gly Ala Ala Ala Ala Gly Ala Ala Ala Thr
                    980                 985                 990
Gly Gly Ala Cys Ala Cys Cys Ala Thr Ala Gly Thr Thr Gly Gly Thr
                    995                 1000                1005
Cys Ala Ala Gly Ala Cys Cys Gly Ala Cys Thr Thr Gly Thr Ala
                    1010                1015                1020
Ala Cys Cys Gly Ala Gly Thr Cys Ala Gly Ala Cys Cys Thr Ala
                    1025                1030                1035
Gly Gly Thr Cys Ala Ala Cys Thr Ala Ala Cys Ala Thr Thr Cys
                    1040                1045                1050
```

```
Cys Thr Cys Cys Ala Ala Gly Cys Cys Ala Thr Thr Ala Thr Cys
    1055                1060                1065

Ala Ala Gly Gly Ala Ala Ala Cys Thr Thr Thr Ala Gly Gly
    1070                1075                1080

Cys Thr Thr Cys Ala Cys Cys Gly Thr Cys Gly Ala Cys Cys
    1085                1090                1095

Cys Cys Ala Cys Thr Ala Thr Cys Ala Cys Thr Gly Cys Cys Ala
    1100                1105                1110

Ala Gly Gly Ala Thr Gly Gly Cys Ala Thr Thr Gly Gly Ala Ala
    1115                1120                1125

Ala Gly Thr Thr Gly Thr Gly Ala Gly Gly Thr Thr Gly Gly Cys
    1130                1135                1140

Gly Gly Thr Thr Ala Thr Thr Ala Cys Ala Thr Cys Cys Cys Thr
    1145                1150                1155

Ala Ala Ala Gly Gly Ala Thr Cys Cys Ala Cys Thr Cys Thr Cys
    1160                1165                1170

Cys Thr Thr Gly Thr Thr Ala Ala Thr Gly Thr Gly Thr Gly Gly
    1175                1180                1185

Gly Cys Cys Ala Thr Thr Thr Cys Thr Cys Gly Ala Gly Ala Cys
    1190                1195                1200

Cys Cys Thr Ala Ala Ala Ala Thr Thr Thr Gly Gly Gly Cys Cys
    1205                1210                1215

Gly Ala Thr Cys Cys Ala Cys Thr Thr Gly Ala Ala Thr Thr Thr
    1220                1225                1230

Cys Ala Gly Cys Cys Cys Ala Cys Thr Cys Gly Ala Thr Thr Cys
    1235                1240                1245

Thr Thr Ala Cys Cys Thr Gly Gly Gly Gly Gly Thr Gly Ala Ala
    1250                1255                1260

Ala Ala Gly Cys Cys Cys Ala Ala Thr Ala Cys Thr Gly Ala Thr
    1265                1270                1275

Ala Thr Cys Ala Ala Ala Gly Gly Ala Ala Ala Thr Gly Ala Thr
    1280                1285                1290

Thr Thr Thr Gly Ala Ala Gly Thr Cys Ala Thr Ala Cys Cys Gly
    1295                1300                1305

Thr Thr Thr Gly Gly Gly Gly Cys Cys Gly Gly Ala Cys Gly Ala
    1310                1315                1320

Ala Gly Gly Ala Thr Thr Thr Gly Thr Gly Thr Cys Gly Gly Ala
    1325                1330                1335

Ala Thr Gly Ala Gly Cys Cys Thr Ala Gly Gly Gly Thr Thr Ala
    1340                1345                1350

Ala Gly Gly Ala Thr Gly Gly Thr Cys Cys Ala Gly Thr Thr Gly
    1355                1360                1365

Thr Thr Gly Ala Cys Thr Gly Cys Ala Ala Cys Cys Cys Thr Ala
    1370                1375                1380

Ala Thr Cys Cys Ala Thr Gly Cys Cys Thr Thr Thr Gly Ala Thr
    1385                1390                1395

Thr Gly Gly Gly Ala Ala Cys Thr Gly Gly Cys Thr Gly Ala Thr
    1400                1405                1410

Gly Gly Gly Thr Thr Ala Ala Cys Cys Cys Ala Ala Ala Ala Gly
    1415                1420                1425

Ala Ala Gly Cys Thr Thr Ala Ala Cys Ala Thr Gly Gly Ala Ala
    1430                1435                1440

Gly Ala Gly Gly Cys Thr Thr Ala Cys Gly Gly Gly Cys Thr Gly
    1445                1450                1455
```

```
Ala Cys Cys Cys Thr Thr Cys Ala Ala Gly Gly Cys Cys
    1460                1465                1470

Gly Cys Ala Cys Cys Gly Thr Thr Ala Gly Thr Gly Gly Thr Thr
    1475                1480                1485

Cys Ala Cys Cys Cys Ala Ala Gly Gly Cys Cys Ala Ala Gly Gly
    1490                1495                1500

Thr Thr Ala Gly Cys Cys Cys Ala Cys Ala Thr Gly Thr Ala
    1505                1510                1515

Thr Ala Thr Gly Ala Gly Ala Cys Gly Ala Cys Thr Ala Ala Gly
    1520                1525                1530

Gly Thr Cys Thr Ala Gly
    1535

<210> SEQ ID NO 31
<211> LENGTH: 1801
<212> TYPE: PRT
<213> ORGANISM: Osteospermum hybrid cultivar

<400> SEQUENCE: 31

Gly Ala Ala Ala Ala Cys Cys Ala Cys Cys Thr Thr Ala Cys Ala
1               5                   10                  15

Thr Thr Cys Thr Thr Ala Thr Thr Thr Ala Thr Thr Ala Thr Thr
            20                  25                  30

Thr Ala Thr Thr Ala Cys Ala Cys Ala Thr Cys Ala Thr Ala Ala
            35                  40                  45

Gly Thr Ala Ala Ala Ala Thr Gly Ala Cys Cys Ala Thr Thr Thr
    50                  55                  60

Ala Cys Cys Cys Cys Thr Thr Gly Thr Ala Cys Thr Cys Thr Ala
65                  70                  75                  80

Ala Gly Thr Thr Gly Cys Ala Thr Cys Ala Cys Thr Gly Gly Ala Thr
                85                  90                  95

Thr Ala Gly Thr Gly Ala Thr Cys Thr Ala Thr Gly Thr Ala Cys Thr
            100                 105                 110

Gly Cys Thr Thr Ala Ala Cys Cys Thr Gly Cys Gly Cys Ala Cys Cys
            115                 120                 125

Cys Gly Thr Cys Ala Cys Thr Cys Thr Ala Ala Cys Cys Gly Cys Cys
    130                 135                 140

Thr Gly Cys Cys Cys Cys Cys Thr Gly Gly Gly Cys Cys Cys Ala Cys
145                 150                 155                 160

Ala Cys Cys Ala Thr Gly Gly Cys Cys Gly Ala Thr Cys Gly Thr Cys
                165                 170                 175

Gly Gly Ala Ala Ala Cys Cys Thr Ala Cys Cys Gly Cys Ala Thr Cys
            180                 185                 190

Thr Cys Gly Gly Cys Gly Thr Ala Gly Thr Thr Cys Cys Gly Cys Ala
            195                 200                 205

Thr Cys Ala Cys Thr Cys Gly Cys Thr Gly Cys Gly Gly Cys Ala
    210                 215                 220

Ala Thr Gly Gly Cys Gly Gly Ala Ala Ala Ala Thr Ala Cys Gly
225                 230                 235                 240

Gly Thr Cys Cys Gly Thr Thr Gly Ala Thr Gly Cys Ala Thr Cys Thr
                245                 250                 255

Cys Cys Gly Gly Thr Thr Ala Gly Gly Thr Thr Thr Gly Thr Thr
            260                 265                 270

Gly Ala Cys Gly Thr Gly Gly Thr Gly Gly Thr Gly Cys Gly Gly
    275                 280                 285
```

```
Cys Gly Thr Cys Thr Gly Cys Thr Gly Cys Cys Thr Gly Cys
    290                 295                 300
Thr Gly Cys Thr Cys Ala Gly Thr Thr Thr Thr Gly Ala Ala Ala
305                 310                 315                 320
Gly Thr Thr Cys Ala Thr Gly Ala Thr Gly Cys Gly Ala Ala Thr Thr
                325                 330                 335
Thr Thr Gly Cys Gly Ala Gly Thr Ala Gly Ala Cys Cys Gly Cys Cys
                340                 345                 350
Thr Ala Ala Thr Thr Cys Cys Gly Gly Thr Cys Gly Ala Ala Ala
            355                 360                 365
Cys Ala Thr Ala Thr Ala Gly Cys Gly Thr Ala Thr Ala Thr Thr
    370                 375                 380
Ala Thr Cys Ala Ala Gly Ala Cys Thr Thr Gly Gly Thr Gly Thr Thr
385                 390                 395                 400
Thr Gly Cys Gly Cys Cys Gly Thr Ala Cys Thr Ala Cys Gly Gly Thr
                405                 410                 415
Cys Cys Gly Cys Gly Gly Thr Gly Gly Cys Gly Thr Ala Thr Gly Cys
                420                 425                 430
Thr Thr Cys Gly Gly Ala Ala Gly Ala Thr Thr Thr Gly Cys Thr Cys
            435                 440                 445
Cys Gly Thr Thr Cys Ala Cys Cys Thr Gly Thr Thr Thr Thr Cys Thr
    450                 455                 460
Thr Cys Thr Ala Ala Ala Gly Cys Gly Cys Thr Thr Gly Ala Thr Gly
465                 470                 475                 480
Ala Thr Thr Thr Cys Cys Gly Gly Cys Ala Thr Gly Thr Cys Cys Gly
                485                 490                 495
Cys Cys Ala Gly Gly Ala Gly Gly Ala Gly Gly Thr Gly Cys Gly
                500                 505                 510
Ala Thr Ala Cys Thr Gly Ala Cys Gly Cys Gly Cys Gly Cys Thr Thr
            515                 520                 525
Thr Gly Ala Thr Cys Gly Gly Cys Gly Cys Cys Gly Gly Thr Gly Ala
            530                 535                 540
Cys Thr Cys Gly Cys Cys Gly Gly Thr Gly Ala Ala Ala Cys Thr Ala
545                 550                 555                 560
Gly Gly Thr Cys Ala Ala Thr Ala Cys Thr Gly Ala Ala Cys Gly
                565                 570                 575
Thr Gly Thr Gly Cys Ala Cys Ala Ala Cys Ala Ala Cys Gly Cys
            580                 585                 590
Ala Thr Thr Gly Gly Cys Gly Cys Gly Cys Gly Thr Gly Ala Thr Gly
                595                 600                 605
Thr Thr Ala Gly Gly Thr Ala Ala Gly Ala Gly Ala Gly Thr Ala Thr
            610                 615                 620
Thr Cys Gly Gly Thr Gly Ala Cys Ala Gly Ala Ala Gly Thr Gly Gly
625                 630                 635                 640
Thr Gly Gly Cys Gly Gly Thr Gly Ala Thr Cys Cys Ala Ala Ala Gly
                645                 650                 655
Gly Cys Gly Gly Ala Thr Gly Ala Gly Thr Cys Ala Ala Gly Gly
                660                 665                 670
Ala Thr Ala Thr Gly Gly Thr Gly Gly Thr Thr Gly Ala Gly Gly Thr
            675                 680                 685
Gly Ala Thr Gly Gly Ala Gly Thr Gly Gly Cys Cys Gly Gly Ala
            690                 695                 700
Gly Ala Ala Thr Thr Cys Ala Ala Thr Ala Thr Cys Gly Gly Thr Gly
```

-continued

```
705                 710                 715                 720

Ala Thr Thr Thr Thr Ala Thr Ala Cys Cys Gly Gly Thr Gly Cys Thr
                725                 730                 735

Thr Gly Ala Thr Thr Cys Thr Cys Thr Cys Gly Ala Thr Cys Thr Gly
            740                 745                 750

Cys Ala Ala Gly Gly Ala Ala Thr Cys Gly Cys Gly Ala Ala Gly Ala
        755                 760                 765

Ala Gly Ala Thr Gly Ala Ala Gly Gly Ala Ala Cys Thr Thr Cys Ala
    770                 775                 780

Cys Gly Thr Gly Cys Gly Ala Thr Thr Thr Gly Ala Thr Thr Cys Gly
785                 790                 795                 800

Thr Thr Cys Cys Thr Thr Gly Gly Thr Ala Ala Gly Ala Thr Cys Cys
                805                 810                 815

Thr Thr Gly Ala Ala Gly Ala Ala Cys Ala Thr Ala Ala Ala Ala Cys
            820                 825                 830

Cys Gly Gly Cys Ala Ala Cys Gly Gly Thr Gly Gly Cys Gly Cys Gly
        835                 840                 845

Thr Cys Gly Ala Gly Thr Cys Ala Ala Cys Ala Cys Ala Cys Thr Gly
    850                 855                 860

Ala Cys Thr Thr Gly Thr Thr Gly Ala Cys Thr Ala Cys Cys Thr Thr
865                 870                 875                 880

Gly Ala Thr Thr Thr Cys Ala Cys Thr Cys Ala Ala Gly Gly Ala Thr
                885                 890                 895

Gly Ala Thr Ala Cys Thr Gly Ala Thr Gly Ala Ala Gly Ala Gly Gly
            900                 905                 910

Gly Thr Gly Gly Gly Ala Ala Gly Cys Thr Thr Thr Cys Ala Gly Ala
        915                 920                 925

Cys Ala Thr Thr Gly Ala Ala Ala Thr Cys Ala Ala Ala Gly Cys Thr
    930                 935                 940

Thr Thr Gly Cys Thr Thr Cys Thr Gly Ala Ala Cys Thr Thr Ala Thr
945                 950                 955                 960

Thr Thr Ala Cys Thr Gly Cys Gly Gly Gly Ala Ala Cys Ala Gly Ala
                965                 970                 975

Cys Ala Cys Gly Thr Cys Ala Thr Cys Thr Ala Gly Thr Ala Cys Cys
            980                 985                 990

Gly Thr Gly Gly Ala Ala Thr Gly  Gly Gly Cys Ala Ala  Thr Ala Gly
        995                 1000                1005

Cys Cys  Gly Ala Ala Cys Thr  Cys Ala Thr Thr Cys  Gly Thr Cys
    1010                 1015                 1020

Ala Thr  Cys Cys Gly Cys Ala  Ala Cys Thr Ala Thr  Thr Gly Ala
    1025                 1030                 1035

Ala Ala  Cys Ala Gly Gly Cys  Cys Cys Ala Ala Gly  Ala Ala Gly
    1040                 1045                 1050

Ala Ala  Ala Thr Ala Gly Ala  Cys Ala Ala Thr Gly  Thr Ala Gly
    1055                 1060                 1065

Thr Ala  Gly Gly Cys Cys Gly  Ala Gly Ala Cys Cys  Ala Cys Cys
    1070                 1075                 1080

Thr Ala  Gly Thr Ala Ala Cys  Cys Gly Ala Ala Thr  Thr Gly Gly
    1085                 1090                 1095

Ala Cys  Cys Thr Ala Ala Cys  Cys Cys Ala Ala Cys  Thr Ala Cys
    1100                 1105                 1110

Cys Ala  Thr Thr Cys Cys Thr  Cys Cys Ala Ala Gly  Cys Cys Ala
    1115                 1120                 1125
```

| | | | | | | | | | | | | |
|---|---|---|---|---|---|---|---|---|---|---|---|---|
|Thr|Thr|Gly|Thr|Gly|Ala|Ala|Gly|Gly|Ala|Gly|Ala|Cys Cys Thr|
| |1130| | | |1135| | | |1140| | | |
|Thr|Thr|Ala|Gly|Gly|Cys|Thr|Cys|Cys|Ala|Cys|Cys|Cys Ala Thr|
| |1145| | | |1150| | | |1155| | | |
|Cys|Ala|Ala|Cys|Ala|Cys|Cys|Ala|Cys|Thr|Cys|Thr|Cys Ala Cys|
| |1160| | | |1165| | | |1170| | | |
|Thr|Ala|Cys|Cys|Ala|Ala|Gly|Ala|Ala|Thr|Thr|Gly|Cys Ala Thr|
| |1175| | | |1180| | | |1185| | | |
|Cys|Cys|Gly|Ala|Gly|Ala|Gly|Thr|Thr|Gly|Thr|Gly|Ala Gly Gly|
| |1190| | | |1195| | | |1200| | | |
|Thr|Cys|Ala|Ala|Cys|Gly|Gly|Gly|Thr|Ala|Cys|Cys|Ala Thr Ala|
| |1205| | | |1210| | | |1215| | | |
|Thr|Cys|Cys|Cys|Thr|Ala|Ala|Gly|Gly|Gly|Ala|Thr|Cys Cys Ala|
| |1220| | | |1225| | | |1230| | | |
|Cys|Ala|Cys|Thr|Cys|Cys|Thr|Thr|Gly|Thr|Thr|Ala|Ala Cys Gly|
| |1235| | | |1240| | | |1245| | | |
|Thr|Gly|Thr|Gly|Gly|Gly|Cys|Cys|Ala|Thr|Ala|Gly|Cys Cys Cys|
| |1250| | | |1255| | | |1260| | | |
|Gly|Ala|Gly|Ala|Cys|Cys|Cys|Ala|Ala|Ala|Ala|Ala|Thr Gly Thr|
| |1265| | | |1270| | | |1275| | | |
|Gly|Gly|Thr|Cys|Cys|Gly|Ala|Ala|Cys|Cys|Ala|Cys|Thr Thr Gly|
| |1280| | | |1285| | | |1290| | | |
|Ala|Ala|Thr|Thr|Cys|Cys|Gly|Thr|Cys|Cys|Ala|Gly|Cys Cys Cys|
| |1295| | | |1300| | | |1305| | | |
|Gly|Ala|Thr|Thr|Cys|Thr|Thr|Ala|Cys|Cys|Cys|Gly|Gly Gly Gly|
| |1310| | | |1315| | | |1320| | | |
|Gly|Thr|Gly|Ala|Ala|Ala|Ala|Gly|Cys|Cys|Cys|Gly|Ala Thr Gly|
| |1325| | | |1330| | | |1335| | | |
|Cys|Thr|Gly|Ala|Thr|Gly|Thr|Thr|Ala|Ala|Gly|Gly|Gly Cys Ala|
| |1340| | | |1345| | | |1350| | | |
|Ala|Cys|Gly|Ala|Thr|Thr|Thr|Thr|Gly|Ala|Ala|Gly|Thr Cys Ala|
| |1355| | | |1360| | | |1365| | | |
|Thr|Ala|Cys|Cys|Ala|Thr|Thr|Cys|Gly|Gly|Gly|Gly|Cys Cys Gly|
| |1370| | | |1375| | | |1380| | | |
|Gly|Ala|Ala|Gly|Gly|Ala|Gly|Gly|Ala|Gly|Thr|Thr|Gly Thr Gly|
| |1385| | | |1390| | | |1395| | | |
|Cys|Gly|Gly|Gly|Thr|Ala|Thr|Gly|Ala|Gly|Thr|Cys|Thr Ala Gly|
| |1400| | | |1405| | | |1410| | | |
|Gly|Ala|Thr|Thr|Gly|Ala|Gly|Ala|Ala|Thr|Gly|Gly|Thr Thr Cys|
| |1415| | | |1420| | | |1425| | | |
|Ala|Ala|Thr|Thr|Ala|Cys|Thr|Cys|Gly|Thr|Thr|Gly|Cys Ala Ala|
| |1430| | | |1435| | | |1440| | | |
|Cys|Gly|Thr|Thr|Gly|Gly|Thr|Ala|Cys|Ala|Ala|Ala|Cys Cys Thr|
| |1445| | | |1450| | | |1455| | | |
|Thr|Thr|Gly|Ala|Cys|Thr|Gly|Gly|Gly|Ala|Ala|Thr|Thr Gly Gly|
| |1460| | | |1465| | | |1470| | | |
|Cys|Thr|Ala|Ala|Thr|Gly|Gly|Gly|Thr|Thr|Gly|Ala|Ala Ala Cys|
| |1475| | | |1480| | | |1485| | | |
|Cys|Cys|Gly|Ala|Gly|Ala|Ala|Gly|Cys|Thr|Thr|Ala|Ala Cys Ala|
| |1490| | | |1495| | | |1500| | | |
|Thr|Gly|Gly|Ala|Ala|Gly|Ala|Ala|Gly|Cys|Gly|Thr|Ala Thr Gly|
| |1505| | | |1510| | | |1515| | | |
|Gly|Gly|Cys|Thr|Ala|Ala|Cys|Thr|Cys|Thr|Thr|Cys|Ala Ala Cys|
| |1520| | | |1525| | | |1530| | | |

```
Gly Gly Gly Cys Thr Gly Cys Ala Cys Cys Thr Thr Gly Thr
    1535                1540                1545

Thr Gly Gly Thr Ala Cys Ala Cys Cys Ala Ala Ala Gly Cys
    1550                1555                1560

Cys Gly Ala Gly Gly Thr Thr Ala Gly Cys Ala Cys Thr Cys
    1565                1570                1575

Ala Thr Gly Thr Gly Thr Ala Cys Gly Gly Ala Ala Gly Thr Ala
    1580                1585                1590

Ala Thr Thr Ala Ala Gly Gly Gly Cys Thr Ala Ala Ala Thr Thr
    1595                1600                1605

Cys Thr Cys Thr Ala Thr Gly Gly Cys Gly Thr Thr Thr Thr
    1610                1615                1620

Gly Thr Thr Thr Gly Cys Ala Thr Ala Ala Thr Thr Ala Thr Thr
    1625                1630                1635

Cys Ala Ala Thr Thr Cys Ala Ala Gly Thr Thr Thr Thr Gly
    1640                1645                1650

Thr Thr Thr Gly Cys Ala Thr Ala Ala Thr Thr Ala Thr Thr Cys
    1655                1660                1665

Ala Ala Thr Thr Cys Ala Ala Ala Thr Thr Thr Cys Gly Ala Thr
    1670                1675                1680

Thr Thr Cys Gly Ala Ala Thr Cys Gly Ala Ala Thr Ala Ala
    1685                1690                1695

Thr Thr Ala Gly Gly Thr Ala Ala Ala Cys Ala Ala Thr Thr Gly
    1700                1705                1710

Thr Ala Thr Thr Thr Gly Cys Thr Ala Thr Thr Thr Gly Ala Ala
    1715                1720                1725

Gly Thr Gly Thr Thr Ala Gly Thr Gly Thr Ala Thr Ala Thr Gly
    1730                1735                1740

Gly Thr Thr Thr Cys Thr Gly Thr Ala Ala Gly Thr Gly Ala Thr
    1745                1750                1755

Thr Gly Ala Gly Ala Thr Ala Thr Thr Thr Thr Cys Ala Thr Gly
    1760                1765                1770

Ala Thr Ala Ala Thr Gly Ala Ala Ala Ala Ala Ala Cys Ala Ala
    1775                1780                1785

Thr Gly Ala Thr Gly Cys Gly Ala Ala Ala Ala Ala
    1790                1795                1800

<210> SEQ ID NO 32
<211> LENGTH: 1679
<212> TYPE: PRT
<213> ORGANISM: Cichorium intybus

<400> SEQUENCE: 32

Gly Ala Ala Ala Ala Cys Thr Cys Cys Gly Thr Cys Thr Ala Cys Ala
1               5                   10                  15

Ala Ala Cys Thr Ala Cys Thr Thr Ala Cys Ala Thr Ala Cys Ala
            20                  25                  30

Cys Thr Thr Thr Thr Thr Gly Ala Ala Cys Cys Gly Ala Ala Cys Cys
        35                  40                  45

Cys Cys Cys Ala Thr Cys Ala Thr Ala Thr Gly Thr Ala Ala Ala Ala
50                  55                  60

Thr Gly Ala Cys Cys Cys Thr Thr Thr Ala Ala Cys Ala Cys Thr
65                  70                  75                  80

Ala Ala Thr Cys Ala Thr Cys Thr Ala Cys Gly Cys Cys Thr Gly Cys
            85                  90                  95
```

-continued

```
Gly Thr Cys Ala Cys Thr Gly Gly Ala Thr Ala Gly Cys Ala Gly
                100                 105                 110
Cys Cys Thr Ala Thr Gly Thr Ala Thr Thr Gly Cys Thr Ala Ala
                115                 120                 125
Cys Cys Thr Gly Cys Gly Gly Ala Ala Cys Cys Gly Cys Gly Gly
                130                 135                 140
Gly Cys Ala Ala Ala Cys Gly Cys Thr Gly Cys Cys Gly Cys
145                 150                 155                 160
Cys Cys Gly Gly Cys Cys Ala Ala Cys Cys Cys Ala Thr Gly
                165                 170                 175
Gly Cys Cys Cys Ala Thr Ala Gly Thr Cys Gly Gly Ala Ala Ala Cys
                180                 185                 190
Thr Thr Ala Cys Cys Thr Cys Ala Cys Thr Cys Gly Gly Thr Ala
                195                 200                 205
Cys Ala Ala Thr Cys Cys Gly Cys Ala Cys Ala Cys Thr Cys
                210                 215                 220
Gly Thr Thr Gly Gly Cys Cys Gly Cys Thr Thr Ala Gly Cys Ala
225                 230                 235                 240
Ala Cys Ala Ala Gly Thr Ala Cys Gly Ala Cys Cys Gly Thr
                245                 250                 255
Thr Gly Ala Thr Gly Cys Ala Cys Cys Thr Ala Cys Gly Thr Cys Thr
                260                 265                 270
Cys Gly Gly Cys Thr Thr Cys Gly Thr Thr Gly Ala Cys Gly Thr Gly
                275                 280                 285
Gly Thr Gly Gly Thr Gly Gly Cys Gly Gly Cys Ala Thr Cys Gly Gly
                290                 295                 300
Cys Ala Thr Cys Cys Gly Thr Cys Gly Cys Thr Gly Cys Ala Cys Ala
305                 310                 315                 320
Gly Thr Thr Thr Thr Thr Gly Ala Ala Gly Gly Cys Thr Cys Ala Thr
                325                 330                 335
Gly Ala Cys Gly Cys Thr Ala Ala Thr Thr Thr Cys Gly Cys Cys Ala
                340                 345                 350
Gly Cys Ala Gly Gly Cys Cys Gly Cys Cys Ala Ala Thr Thr Cys
                355                 360                 365
Cys Gly Gly Ala Gly Cys Gly Ala Ala Gly Cys Ala Thr Ala Thr Gly
                370                 375                 380
Gly Cys Gly Thr Ala Thr Ala Ala Thr Ala Thr Cys Ala Gly Gly
385                 390                 395                 400
Ala Thr Cys Thr Gly Gly Thr Ala Thr Thr Cys Gly Cys Gly Cys Cys
                405                 410                 415
Gly Thr Ala Cys Gly Gly Thr Cys Cys Gly Cys Gly Gly Thr Gly Gly
                420                 425                 430
Cys Gly Ala Ala Thr Cys Thr Thr Cys Gly Gly Ala Ala Ala Ala
                435                 440                 445
Thr Thr Thr Gly Cys Thr Cys Gly Gly Thr Gly Cys Ala Thr Cys Thr
                450                 455                 460
Gly Thr Thr Thr Thr Cys Thr Gly Cys Cys Ala Ala Ala Thr Cys Ala
465                 470                 475                 480
Cys Thr Thr Gly Ala Thr Gly Ala Thr Thr Cys Cys Gly Thr Cys
                485                 490                 495
Ala Cys Gly Thr Thr Cys Gly Ala Cys Ala Gly Gly Ala Gly Gly Ala
                500                 505                 510
Gly Gly Thr Ala Gly Cys Gly Ala Thr Ala Cys Thr Cys Ala Cys Gly
```

```
            515                 520                 525
Cys Gly Cys Gly Cys Thr Cys Thr Gly Thr Thr Gly Ala Thr Gly
    530                 535                 540
Cys Cys Gly Gly Ala Ala Ala Thr Cys Ala Ala Cys Gly Gly Thr
545                 550                 555                 560
Gly Ala Thr Ala Thr Thr Gly Gly Gly Thr Cys Ala Gly Cys Thr Ala
                565                 570                 575
Cys Thr Thr Ala Ala Cys Gly Thr Gly Thr Gly Cys Ala Cys Cys Ala
            580                 585                 590
Cys Ala Ala Ala Cys Gly Cys Ala Thr Thr Gly Gly Cys Ala Cys Gly
        595                 600                 605
Ala Gly Thr Ala Ala Thr Gly Thr Thr Ala Gly Gly Cys Ala Gly Gly
610                 615                 620
Ala Gly Ala Gly Thr Ala Thr Thr Gly Gly Cys Gly Ala Thr Gly
625                 630                 635                 640
Gly Ala Ala Gly Cys Gly Gly Ala Gly Gly Ala Gly Cys Gly Ala
                645                 650                 655
Thr Cys Cys Ala Ala Gly Gly Cys Ala Gly Ala Thr Gly Ala Gly
    660                 665                 670
Thr Thr Cys Ala Ala Gly Gly Ala Thr Ala Thr Gly Thr Gly Gly
    675                 680                 685
Thr Thr Gly Ala Ala Cys Thr Gly Ala Thr Gly Gly Thr Gly Thr Thr
    690                 695                 700
Ala Gly Cys Cys Gly Gly Ala Gly Ala Ala Thr Thr Cys Ala Ala Cys
705                 710                 715                 720
Ala Thr Cys Gly Gly Thr Gly Ala Cys Thr Thr Cys Ala Thr Cys Cys
                725                 730                 735
Cys Gly Gly Cys Gly Cys Thr Thr Gly Ala Thr Ala Thr Thr Cys Thr
            740                 745                 750
Gly Gly Ala Cys Cys Thr Gly Cys Ala Ala Gly Gly Cys Gly Thr Gly
        755                 760                 765
Ala Cys Gly Ala Ala Ala Ala Gly Ala Thr Gly Ala Ala Gly Ala
    770                 775                 780
Ala Ala Cys Thr Thr Cys Ala Cys Ala Cys Gly Gly Ala Thr Thr
785                 790                 795                 800
Cys Gly Ala Thr Thr Cys Gly Thr Thr Cys Thr Cys Thr Ala Ala Cys
                805                 810                 815
Ala Cys Gly Ala Thr Cys Cys Thr Cys Gly Ala Ala Gly Ala Gly Cys
            820                 825                 830
Ala Thr Ala Ala Ala Cys Cys Gly Gly Cys Gly Gly Cys Ala Gly
        835                 840                 845
Cys Gly Gly Cys Gly Cys Gly Thr Cys Gly Gly Cys Thr Cys Ala Cys
    850                 855                 860
Gly Thr Ala Gly Ala Cys Thr Thr Gly Thr Thr Gly Ala Gly Cys Ala
865                 870                 875                 880
Cys Gly Thr Thr Gly Ala Thr Thr Thr Cys Gly Cys Thr Gly Ala Ala
                885                 890                 895
Gly Gly Ala Thr Gly Ala Thr Gly Cys Cys Gly Ala Thr Gly Gly Ala
            900                 905                 910
Gly Ala Gly Gly Gly Ala Gly Gly Ala Ala Gly Cys Thr Thr Thr
        915                 920                 925
Cys Gly Gly Ala Cys Ala Cys Cys Gly Ala Ala Thr Thr Ala Ala
    930                 935                 940
```

```
Ala Gly Cys Thr Thr Thr Ala Cys Thr Thr Cys Thr Gly Ala Ala Thr
945                 950                 955                 960

Thr Thr Ala Thr Thr Cys Gly Cys Thr Gly Cys Gly Gly Gly Ala Ala
                965                 970                 975

Cys Cys Gly Ala Thr Ala Cys Gly Thr Cys Ala Thr Cys Thr Ala Gly
            980                 985                 990

Thr Ala Cys Cys Gly Thr Gly Gly  Ala Ala Thr Gly Gly  Gly Cys Ala
        995                 1000                1005

Ala Thr  Ala Gly Cys Gly Gly  Ala Ala Cys Thr Cys  Ala Thr Cys
    1010                1015                1020

Cys Gly  Cys Cys Ala Thr Cys  Cys Gly Cys Ala Thr  Thr Thr Ala
    1025                1030                1035

Ala Thr  Gly Ala Ala Ala Cys  Ala Ala Gly Cys Cys  Cys Ala Ala
    1040                1045                1050

Cys Ala  Ala Gly Ala Ala Ala  Thr Gly Gly Ala Cys  Ala Cys Ala
    1055                1060                1065

Gly Thr  Ala Gly Thr Ala Gly  Gly Thr Cys Ala Ala  Gly Ala Cys
    1070                1075                1080

Cys Gly  Gly Cys Thr Thr Gly  Thr Ala Ala Cys Cys  Gly Ala Ala
    1085                1090                1095

Thr Thr  Gly Gly Ala Cys Cys  Thr Gly Ala Gly Thr  Cys Ala Ala
    1100                1105                1110

Cys Thr  Ala Ala Cys Ala Thr  Thr Cys Cys Thr Cys  Cys Ala Ala
    1115                1120                1125

Gly Cys  Cys Ala Thr Thr Gly  Thr Gly Ala Ala Gly  Gly Ala Ala
    1130                1135                1140

Ala Cys  Cys Thr Thr Thr Ala  Gly Gly Cys Thr Cys  Cys Ala Cys
    1145                1150                1155

Cys Cys  Ala Thr Cys Ala Ala  Cys Ala Cys Cys Ala  Cys Thr Cys
    1160                1165                1170

Thr Cys  Cys Thr Thr Ala Cys  Cys Ala Ala Gly Ala  Ala Thr Ala
    1175                1180                1185

Gly Cys  Ala Thr Cys Cys Gly  Ala Gly Ala Gly Cys  Thr Gly Thr
    1190                1195                1200

Gly Ala  Gly Ala Thr Cys Ala  Ala Cys Gly Gly Gly  Thr Ala Cys
    1205                1210                1215

Ala Ala  Cys Ala Thr Thr Cys  Cys Ala Ala Ala Ala  Gly Gly Ala
    1220                1225                1230

Thr Cys  Cys Ala Cys Ala Cys  Thr Cys Cys Thr Thr  Gly Thr Cys
    1235                1240                1245

Ala Ala  Cys Gly Thr Gly Thr  Gly Gly Gly Cys Cys  Ala Thr Ala
    1250                1255                1260

Gly Cys  Cys Cys Gly Cys Gly  Ala Cys Cys Cys Gly  Ala Ala Ala
    1265                1270                1275

Ala Thr  Gly Thr Gly Gly Ala  Cys Cys Ala Ala Cys  Cys Cys Gly
    1280                1285                1290

Cys Thr  Thr Cys Ala Gly Thr  Thr Cys Cys Ala Gly  Cys Cys Cys
    1295                1300                1305

Gly Cys  Cys Cys Gly Gly Thr  Thr Cys Ala Thr Gly  Cys Cys Cys
    1310                1315                1320

Gly Gly  Gly Gly Gly Cys Gly  Ala Ala Ala Ala Gly  Cys Cys Cys
    1325                1330                1335

Ala Ala  Thr Gly Cys Thr Gly  Ala Thr Gly Thr Cys  Ala Ala Gly
    1340                1345                1350
```

Gly Gly Ala Ala Ala Thr Gly Ala Thr Thr Thr Gly Ala Ala
    1355                1360                1365

Gly Thr Gly Ala Thr Ala Cys Cys Ala Thr Thr Gly Gly Gly
    1370                1375                1380

Gly Cys Ala Gly Gly Ala Cys Gly Ala Ala Gly Ala Thr Thr
    1385                1390                1395

Thr Gly Thr Gly Cys Gly Gly Gly Thr Ala Thr Gly Ala Gly Cys
    1400                1405                1410

Cys Thr Ala Gly Gly Gly Thr Thr Gly Ala Gly Ala Ala Thr Gly
    1415                1420                1425

Gly Thr Cys Cys Ala Ala Thr Thr Gly Cys Thr Cys Ala Cys Thr
    1430                1435                1440

Gly Cys Ala Ala Cys Ala Cys Thr Cys Gly Thr Thr Cys Ala Ala
    1445                1450                1455

Gly Cys Cys Thr Thr Thr Gly Ala Thr Thr Gly Gly Ala Ala
    1460                1465                1470

Thr Thr Gly Gly Cys Thr Ala Ala Thr Gly Gly Thr Thr Gly
    1475                1480                1485

Gly Ala Ala Cys Cys Ala Gly Cys Cys Gly Ala Cys Cys Thr Thr
    1490                1495                1500

Ala Ala Cys Ala Thr Gly Gly Ala Ala Gly Ala Ala Gly Cys Cys
    1505                1510                1515

Thr Ala Thr Gly Gly Gly Thr Gly Ala Cys Cys Cys Thr Thr
    1520                1525                1530

Cys Ala Ala Ala Gly Gly Gly Cys Thr Gly Cys Ala Cys Cys Cys
    1535                1540                1545

Thr Thr Gly Gly Thr Thr Gly Thr Gly Cys Ala Cys Cys Cys Ala
    1550                1555                1560

Ala Gly Gly Cys Cys Gly Ala Gly Gly Thr Thr Ala Gly Cys Cys
    1565                1570                1575

Cys Cys Cys Thr Ala Thr Gly Thr Gly Thr Ala Cys Ala Ala Ala
    1580                1585                1590

Ala Cys Thr Thr Ala Ala Gly Ala Cys Cys Cys Gly Ala Thr Ala
    1595                1600                1605

Ala Ala Cys Cys Gly Ala Ala Thr Gly Cys Thr Cys Thr Thr Thr
    1610                1615                1620

Thr Gly Thr Gly Thr Thr Thr Thr Thr Gly Thr Thr Gly Cys
    1625                1630                1635

Thr Thr Ala Ala Thr Ala Thr Ala Ala Thr Thr Gly Gly Ala Gly
    1640                1645                1650

Thr Thr Thr Gly Thr Gly Thr Thr Thr Cys Ala Ala Ala Ala Ala
    1655                1660                1665

Ala Ala Ala Ala Ala Ala Ala Ala Ala Ala
    1670                1675

<210> SEQ ID NO 33
<211> LENGTH: 1981
<212> TYPE: PRT
<213> ORGANISM: Antirrhinum majus

<400> SEQUENCE: 33

Gly Cys Cys Gly Gly Cys Cys Thr Ala Ala Thr Ala Ala Cys Thr Ala
1               5                   10                  15

Ala Ala Ala Gly Cys Cys Cys Ala Cys Thr Cys Thr Thr Cys Cys
                20                  25                  30

```
Gly Ala Cys Cys Ala Thr Cys Thr Ala Thr Ala Cys Ala Thr Gly Cys
        35                  40                  45

Ala Ala Cys Ala Cys Cys Ala Ala Thr Ala Thr Thr Ala Thr Thr Cys
    50                  55                  60

Thr Thr Thr Ala Ala Thr Thr Ala Cys Gly Ala Thr Gly Gly Ala Thr
65                  70                  75                  80

Gly Ala Thr Ala Thr Thr Ala Gly Cys Ala Thr Ala Ala Cys Cys Ala
                85                  90                  95

Gly Cys Thr Thr Ala Thr Thr Gly Gly Thr Gly Cys Cys Ala Thr Gly
            100                 105                 110

Thr Ala Cys Thr Thr Thr Thr Ala Thr Ala Thr Thr Ala Gly Gly Gly
        115                 120                 125
Thr Thr Cys Thr Thr Gly Cys Thr Thr Cys Thr Ala Thr Ala Thr Thr
    130                 135                 140

Cys Cys Thr Thr Cys Cys Thr Cys Ala Ala Cys Ala Gly Ala Ala Ala
145                 150                 155                 160
Ala Gly Thr Ala Ala Ala Gly Cys Cys Ala Cys Thr Gly Cys Cys Ala
                165                 170                 175
Cys Cys Thr Gly Gly Ala Cys Cys Gly Ala Ala Gly Cys Cys Ala Thr
            180                 185                 190

Gly Gly Cys Cys Cys Ala Thr Cys Gly Thr Cys Gly Gly Ala Ala Ala
        195                 200                 205

Thr Cys Thr Gly Cys Cys Ala Cys Ala Thr Cys Thr Thr Gly Gly Gly
    210                 215                 220

Cys Cys Gly Ala Ala Gly Cys Cys Cys Cys Ala Cys Cys Ala Gly Thr
225                 230                 235                 240

Cys Gly Ala Thr Gly Gly Cys Gly Gly Cys Gly Cys Thr Gly Gly Cys
                245                 250                 255

Ala Cys Gly Gly Gly Thr Gly Cys Ala Cys Gly Gly Cys Cys Cys Ala
            260                 265                 270

Thr Thr Ala Ala Thr Thr Cys Ala Thr Cys Thr Gly Ala Ala Gly Ala
        275                 280                 285

Thr Gly Gly Gly Cys Thr Thr Thr Gly Thr Gly Cys Ala Thr Gly Thr
    290                 295                 300

Gly Gly Thr Thr Gly Thr Gly Gly Cys Cys Thr Cys Cys Thr Cys Ala
305                 310                 315                 320

Gly Cys Ala Thr Cys Cys Gly Thr Thr Gly Cys Gly Gly Ala Gly Ala
                325                 330                 335

Ala Ala Thr Thr Thr Cys Thr Gly Ala Ala Gly Gly Thr Gly Cys Ala
            340                 345                 350

Thr Gly Ala Cys Gly Cys Ala Ala Ala Cys Thr Thr Cys Thr Cys Gly
        355                 360                 365

Ala Gly Cys Ala Gly Gly Cys Cys Thr Cys Cys Cys Ala Ala Thr Thr
    370                 375                 380

Cys Gly Gly Gly Thr Gly Cys Ala Ala Ala Ala Cys Ala Cys Gly Thr
385                 390                 395                 400

Gly Gly Cys Cys Thr Ala Cys Ala Ala Cys Thr Ala Thr Cys Ala Gly
                405                 410                 415

Gly Ala Cys Thr Thr Gly Gly Thr Cys Thr Thr Thr Gly Cys Thr Cys
            420                 425                 430

Cys Thr Thr Ala Thr Gly Gly Cys Cys Cys Ala Cys Gly Cys Thr Gly
        435                 440                 445

Gly Cys Gly Gly Ala Thr Gly Cys Thr Cys Ala Gly Gly Ala Ala Ala
```

-continued

```
                450                 455                 460
Ala Thr Cys Thr Gly Thr Gly Cys Ala Cys Thr Cys Cys Ala Cys Cys
465                 470                 475                 480

Thr Cys Thr Thr Cys Thr Cys Cys Gly Cys Ala Ala Ala Gly Cys
                    485                 490                 495

Cys Thr Thr Gly Ala Ala Cys Gly Ala Cys Thr Thr Cys Ala Cys Ala
                500                 505                 510

Cys Ala Cys Gly Thr Cys Ala Gly Ala Cys Ala Gly Gly Ala Thr Gly
                515                 520                 525

Ala Gly Gly Thr Gly Gly Gly Gly Ala Thr Cys Cys Thr Cys Ala Cys
530                 535                 540

Thr Cys Gly Cys Gly Thr Thr Cys Thr Ala Gly Cys Ala Gly Ala Thr
545                 550                 555                 560

Gly Cys Ala Gly Gly Ala Gly Ala Ala Ala Cys Gly Cys Cys Gly Thr
                565                 570                 575

Thr Gly Ala Ala Ala Thr Thr Ala Gly Gly Gly Cys Ala Gly Ala Thr
                580                 585                 590

Gly Ala Thr Gly Ala Ala Cys Ala Cys Ala Thr Gly Cys Gly Cys Cys
                595                 600                 605

Ala Cys Cys Ala Ala Thr Gly Cys Ala Ala Thr Ala Gly Cys Gly Cys
610                 615                 620

Gly Thr Gly Thr Thr Ala Thr Gly Thr Thr Gly Gly Thr Cys Gly
625                 630                 635                 640

Ala Cys Gly Cys Gly Thr Gly Gly Thr Thr Gly Gly Ala Cys Ala Cys
                645                 650                 655

Gly Cys Ala Gly Ala Cys Thr Cys Ala Ala Gly Gly Cys Gly Gly
                660                 665                 670

Ala Gly Gly Ala Gly Thr Thr Ala Ala Gly Gly Cys Ala Ala Thr
675                 680                 685

Gly Gly Thr Ala Gly Thr Gly Gly Ala Gly Thr Thr Gly Ala Thr Gly
690                 695                 700

Gly Thr Ala Thr Thr Ala Gly Cys Thr Gly Gly Thr Gly Thr Gly Thr
705                 710                 715                 720

Thr Cys Ala Ala Cys Thr Thr Ala Gly Gly Thr Gly Ala Thr Thr Thr
                725                 730                 735

Thr Ala Thr Cys Cys Ala Cys Cys Thr Cys Thr Thr Gly Ala Ala
                740                 745                 750

Ala Ala Ala Thr Thr Gly Gly Ala Thr Cys Thr Thr Cys Ala Ala Gly
                755                 760                 765

Gly Thr Gly Thr Cys Ala Thr Thr Gly Cys Thr Ala Ala Gly Ala Thr
770                 775                 780

Gly Ala Ala Gly Ala Ala Gly Cys Thr Thr Cys Ala Cys Thr Thr Gly
785                 790                 795                 800

Cys Gly Thr Thr Thr Cys Gly Ala Cys Thr Cys Gly Thr Thr Cys Thr
                805                 810                 815

Thr Gly Ala Gly Thr Ala Gly Ala Thr Cys Cys Thr Thr Gly Ala
                820                 825                 830

Ala Gly Ala Cys Cys Ala Cys Ala Ala Gly Ala Thr Cys Ala Ala Cys
                835                 840                 845

Ala Gly Cys Thr Cys Ala Gly Ala Thr Gly Ala Ala Ala Cys Cys Ala
                850                 855                 860

Ala Ala Gly Gly Cys Cys Ala Thr Thr Cys Gly Gly Ala Thr Thr Thr
865                 870                 875                 880
```

-continued

```
Gly Thr Thr Gly Ala Ala Cys Ala Thr Gly Thr Ala Thr Thr
            885                 890                 895
Thr Cys Thr Thr Thr Gly Ala Ala Gly Gly Ala Cys Gly Thr Gly
            900                 905                 910
Ala Thr Gly Ala Thr Gly Cys Cys Gly Ala Gly Gly Ala Gly Gly
            915                 920                 925
Gly Ala Gly Gly Cys Thr Cys Ala Cys Cys Gly Ala Cys Gly Thr Ala
        930                 935                 940
Gly Ala Ala Thr Thr Ala Ala Gly Cys Gly Thr Thr Gly Cys
945                 950                 955                 960
Thr Cys Thr Thr Gly Ala Ala Cys Thr Gly Thr Thr Gly Cys
            965                 970                 975
Thr Gly Cys Ala Gly Gly Ala Ala Cys Thr Gly Ala Cys Ala Cys Ala
            980                 985                 990
Ala Cys Ala Thr Cys Ala Ala Gly Cys Ala Cys Thr Gly Thr Gly Gly
        995                 1000                1005
Ala Ala  Thr Gly Gly Thr Gly  Cys Ala Thr Ala Gly  Cys Thr Gly
        1010                1015                1020
Ala Gly  Thr Thr Ala Gly Thr  Ala Cys Gly Ala Cys  Ala Thr Cys
        1025                1030                1035
Cys Thr  Gly Ala Ala Ala Thr  Cys Cys Thr Thr Gly  Cys Cys Cys
        1040                1045                1050
Ala Ala  Gly Thr Cys Ala Ala  Ala Ala Ala Gly  Ala Ala Cys
        1055                1060                1065
Thr Cys  Gly Ala Cys Thr Cys  Thr Gly Thr Thr Gly  Thr Thr Gly
        1070                1075                1080
Gly Thr  Ala Ala Gly Ala Ala  Thr Cys Gly Gly Gly  Thr Gly Gly
        1085                1090                1095
Thr Gly  Ala Ala Gly Gly Ala  Gly Gly Cys Thr Gly  Ala Thr Cys
        1100                1105                1110
Thr Gly  Gly Cys Cys Gly Gly  Ala Thr Thr Ala Cys  Cys Ala Thr
        1115                1120                1125
Thr Cys  Cys Thr Cys Cys Ala  Ala Gly Cys Gly Gly  Thr Cys Gly
        1130                1135                1140
Thr Cys  Ala Ala Gly Gly Ala  Ala Ala Ala Thr Thr  Thr Cys Cys
        1145                1150                1155
Gly Ala  Cys Thr Cys Thr Ala  Thr Cys Cys Thr Cys  Cys Cys Ala
        1160                1165                1170
Cys Cys  Cys Cys Gly Cys Thr  Cys Thr Cys Cys Cys  Thr Ala Cys
        1175                1180                1185
Cys Gly  Ala Gly Gly Ala Thr  Cys Gly Cys Ala Cys  Ala Thr Gly
        1190                1195                1200
Ala Gly  Ala Gly Thr Thr Gly  Thr Gly Ala Ala Gly  Thr Gly Ala
        1205                1210                1215
Ala Thr  Gly Gly Ala Thr Ala  Cys Thr Gly Ala Thr  Thr Thr Cys
        1220                1225                1230
Cys Ala  Ala Ala Gly Gly Gly  Thr Thr Cys Gly Ala  Cys Ala Cys
        1235                1240                1245
Thr Thr  Cys Thr Thr Gly Thr  Cys Ala Ala Thr Gly  Thr Thr Thr
        1250                1255                1260
Gly Gly  Gly Cys Ala Ala Thr  Thr Gly Cys Thr Cys  Gly Cys Gly
        1265                1270                1275
Ala Thr  Cys Cys Ala Ala Ala  Thr Gly Thr Gly Thr  Gly Gly Gly
        1280                1285                1290
```

```
Ala Thr Gly Ala Ala Cys Cys Ala Cys Thr Ala Gly Ala Gly Thr
1295                1300                1305

Thr Cys Cys Gly Gly Cys Cys Thr Gly Ala Ala Cys Gly Ala Thr
1310                1315                1320

Thr Cys Thr Thr Gly Ala Ala Gly Gly Cys Gly Gly Gly Gly
1325                1330                1335

Ala Ala Ala Ala Gly Cys Cys Thr Ala Ala Thr Gly Thr Cys Gly
1340                1345                1350

Ala Thr Gly Thr Thr Ala Gly Ala Gly Gly Ala Ala Thr Gly
1355                1360                1365

Ala Thr Thr Thr Cys Gly Ala Ala Thr Thr Gly Ala Thr Ala Cys
1370                1375                1380

Cys Gly Thr Thr Cys Gly Gly Ala Gly Cys Gly Gly Cys Cys
1385                1390                1395

Gly Ala Ala Gly Ala Ala Thr Thr Thr Gly Thr Gly Cys Ala Gly
1400                1405                1410

Gly Ala Ala Thr Gly Ala Gly Cys Thr Thr Ala Gly Gly Ala Ala
1415                1420                1425

Thr Ala Cys Gly Thr Ala Thr Gly Gly Thr Cys Cys Ala Gly Thr
1430                1435                1440

Thr Gly Thr Thr Gly Ala Cys Ala Gly Cys Ala Ala Cys Thr Thr
1445                1450                1455

Thr Gly Ala Thr Cys Cys Ala Thr Gly Cys Gly Thr Thr Thr Gly
1460                1465                1470

Ala Cys Thr Thr Thr Gly Ala Thr Thr Thr Gly Gly Cys Gly Gly
1475                1480                1485

Ala Thr Gly Gly Ala Cys Ala Gly Thr Thr Gly Cys Cys Thr Gly
1490                1495                1500

Ala Ala Ala Gly Cys Thr Thr Ala Ala Ala Cys Ala Thr Gly Gly
1505                1510                1515

Ala Gly Gly Ala Ala Gly Cys Thr Thr Ala Thr Gly Gly Gly Cys
1520                1525                1530

Thr Gly Ala Cys Cys Thr Thr Gly Cys Ala Ala Cys Gly Ala Gly
1535                1540                1545

Cys Thr Gly Ala Cys Cys Cys Thr Thr Thr Gly Gly Thr Ala Gly
1550                1555                1560

Thr Gly Cys Ala Cys Cys Cys Gly Ala Ala Gly Cys Cys Thr Ala
1565                1570                1575

Gly Gly Thr Thr Gly Gly Cys Ala Cys Cys Thr Cys Ala Thr Gly
1580                1585                1590

Thr Thr Thr Ala Thr Cys Ala Ala Ala Cys Thr Thr Ala Gly Gly
1595                1600                1605

Ala Cys Thr Cys Ala Thr Gly Thr Thr Thr Ala Gly Ala Gly Ala
1610                1615                1620

Ala Cys Cys Thr Cys Thr Thr Gly Thr Thr Gly Thr Thr Thr Thr
1625                1630                1635

Ala Thr Cys Ala Gly Ala Thr Thr Gly Ala Ala Gly Thr Gly Thr
1640                1645                1650

Gly Ala Thr Gly Thr Cys Cys Ala Ala Gly Ala Cys Cys Cys
1655                1660                1665

Cys Thr Thr Thr Ala Thr Thr Ala Gly Cys Ala Thr Ala Ala Gly
1670                1675                1680

Thr Ala Cys Cys Thr Ala Cys Cys Cys Ala Thr Gly Gly Cys Gly
```

1685 1690 1695

Cys Ala Thr Cys Thr Gly Thr Ala Ala Thr Ala Ala Ala Ala Thr
1700 1705 1710

Cys Thr Gly Gly Gly Thr Cys Ala Ala Ala Thr Gly Cys Cys Ala
1715 1720 1725

Ala Ala Ala Cys Thr Ala Cys Thr Cys Gly Thr Gly Thr Gly Thr
1730 1735 1740

Thr Ala Thr Cys Thr Cys Cys Ala Cys Thr Thr Gly Gly Cys Ala
1745 1750 1755

Ala Thr Thr Ala Ala Ala Gly Thr Cys Cys Thr Ala Thr Gly Thr
1760 1765 1770

Thr Ala Thr Thr Thr Cys Ala Ala Thr Thr Ala Gly Cys Ala Ala
1775 1780 1785

Ala Ala Ala Ala Ala Cys Cys Cys Cys Thr Gly Thr Gly Cys Ala
1790 1795 1800

Cys Ala Ala Thr Ala Cys Cys Ala Ala Ala Cys Thr Thr Thr Gly
1805 1810 1815

Cys Thr Cys Cys Cys Ala Ala Thr Thr Cys Cys Cys Ala Ala Cys
1820 1825 1830

Thr Cys Ala Thr Thr Thr Thr Cys Ala Ala Cys Thr Thr Thr Gly
1835 1840 1845

Ala Cys Thr Gly Gly Ala Thr Gly Cys Ala Ala Ala Ala Thr Gly
1850 1855 1860

Gly Cys Cys Thr Thr Thr Thr Thr Gly Cys Cys Cys Ala Thr Ala
1865 1870 1875

Thr Ala Thr Ala Ala Ala Gly Cys Thr Thr Cys Thr Ala Ala Thr
1880 1885 1890

Cys Ala Thr Thr Thr Ala Ala Gly Ala Ala Thr Thr Thr Thr Ala
1895 1900 1905

Cys Thr Thr Cys Ala Ala Ala Gly Ala Thr Thr Thr Thr Gly Ala
1910 1915 1920

Ala Ala Cys Thr Ala Ala Ala Ala Thr Thr Cys Thr Thr Thr Thr
1925 1930 1935

Thr Cys Ala Thr Thr Ala Ala Ala Ala Ala Ala Ala Ala Ala Ala
1940 1945 1950

Ala Ala Ala Ala Ala Ala Ala Ala Ala Ala Ala Ala Ala Ala Ala
1955 1960 1965

Ala Ala Ala Ala Ala Ala Ala Ala Ala Ala Ala Ala Ala
1970 1975 1980

<210> SEQ ID NO 34
<211> LENGTH: 1542
<212> TYPE: PRT
<213> ORGANISM: Arabidopsis thaliana chromosome V

<400> SEQUENCE: 34

Ala Thr Gly Gly Cys Ala Ala Cys Thr Cys Thr Ala Thr Thr Thr Cys
1 5 10 15

Thr Cys Ala Cys Ala Ala Thr Cys Cys Thr Cys Cys Thr Ala Gly Cys
20 25 30

Cys Ala Cys Thr Gly Thr Cys Cys Thr Cys Thr Thr Cys Cys Thr Cys
35 40 45

Ala Thr Cys Cys Thr Cys Cys Gly Thr Ala Thr Cys Thr Thr Cys Thr
50 55 60

Cys Thr Cys Ala Cys Cys Gly Thr Cys Gly Cys Ala Ala Cys Cys Gly

```
65                  70                  75                  80

Cys Ala Gly Cys Cys Ala Cys Ala Ala Cys Ala Ala Cys Cys Gly Thr
                85                  90                  95

Cys Thr Thr Cys Cys Ala Cys Cys Gly Gly Gly Gly Cys Cys Ala Ala
            100                 105                 110

Ala Cys Cys Cys Ala Thr Gly Gly Cys Cys Cys Ala Thr Cys Ala Thr
        115                 120                 125

Cys Gly Gly Ala Ala Ala Cys Cys Thr Cys Cys Cys Thr Cys Ala Cys
    130                 135                 140

Ala Thr Gly Gly Gly Cys Ala Cys Thr Ala Ala Gly Cys Cys Thr Cys
145                 150                 155                 160

Ala Thr Cys Gly Ala Ala Cys Cys Cys Thr Thr Thr Cys Cys Gly Cys
                165                 170                 175

Cys Ala Thr Gly Gly Thr Thr Ala Cys Thr Ala Cys Thr Thr Ala Cys
            180                 185                 190

Gly Gly Cys Cys Cys Thr Ala Thr Cys Cys Thr Cys Cys Ala Cys Cys
        195                 200                 205

Thr Cys Cys Gly Ala Cys Thr Ala Gly Gly Gly Thr Thr Cys Gly Thr
    210                 215                 220

Ala Gly Ala Cys Gly Thr Cys Gly Thr Gly Gly Thr Cys Gly Cys Cys
225                 230                 235                 240

Gly Cys Thr Thr Cys Thr Ala Ala Ala Thr Cys Cys Gly Thr Gly Gly
                245                 250                 255

Cys Cys Gly Ala Gly Cys Ala Gly Thr Thr Cys Thr Thr Gly Ala Ala
            260                 265                 270

Ala Ala Thr Ala Cys Ala Cys Gly Ala Cys Gly Cys Cys Ala Ala Thr
        275                 280                 285

Thr Thr Cys Gly Cys Thr Ala Gly Cys Cys Gly Ala Cys Cys Ala Cys
    290                 295                 300

Cys Ala Ala Ala Cys Thr Cys Ala Gly Gly Ala Gly Cys Thr Ala Ala
305                 310                 315                 320

Ala Cys Ala Cys Ala Thr Gly Gly Cys Ala Thr Ala Thr Ala Ala Cys
                325                 330                 335

Thr Ala Thr Cys Ala Ala Gly Ala Thr Cys Thr Thr Gly Thr Cys Thr
            340                 345                 350

Thr Thr Gly Cys Ala Cys Cys Thr Thr Ala Cys Gly Gly Ala Cys Ala
        355                 360                 365

Cys Cys Gly Ala Thr Gly Gly Ala Gly Ala Cys Thr Gly Thr Thr Gly
    370                 375                 380

Ala Gly Ala Ala Ala Gly Ala Thr Thr Ala Gly Thr Thr Cys Thr Gly
385                 390                 395                 400

Thr Thr Cys Ala Thr Cys Thr Ala Thr Thr Thr Thr Cys Ala Gly Cys
                405                 410                 415

Thr Ala Ala Ala Gly Cys Thr Cys Thr Cys Gly Ala Ala Gly Ala Thr
            420                 425                 430

Thr Thr Cys Ala Ala Ala Cys Ala Thr Gly Thr Thr Cys Gly Ala Cys
        435                 440                 445

Ala Gly Gly Ala Ala Gly Ala Gly Gly Thr Thr Gly Gly Ala Ala Cys
    450                 455                 460

Gly Cys Thr Ala Ala Cys Gly Cys Gly Gly Gly Ala Gly Cys Thr Ala
465                 470                 475                 480

Gly Thr Gly Cys Gly Thr Gly Thr Thr Gly Gly Cys Ala Cys Gly Ala
                485                 490                 495
```

Ala Ala Cys Cys Cys Gly Thr Gly Ala Ala Thr Thr Thr Ala Gly Gly
500 505 510

Cys Cys Ala Gly Thr Thr Gly Gly Thr Gly Ala Ala Cys Ala Thr Gly
515 520 525

Thr Gly Thr Gly Thr Ala Gly Thr Cys Ala Ala Cys Gly Cys Thr Cys
530 535 540

Thr Ala Gly Gly Ala Cys Gly Ala Gly Ala Gly Ala Thr Gly Ala Thr
545 550 555 560

Cys Gly Gly Ala Cys Gly Gly Cys Gly Ala Thr Thr Gly Thr Thr Cys
565 570 575

Gly Gly Cys Gly Cys Cys Gly Ala Cys Gly Cys Cys Gly Ala Thr Cys
580 585 590

Ala Thr Ala Ala Ala Gly Cys Thr Gly Ala Cys Gly Ala Gly Thr Thr
595 600 605

Thr Cys Gly Ala Thr Cys Ala Ala Thr Gly Gly Thr Gly Ala Cys Gly
610 615 620

Gly Ala Ala Ala Thr Gly Ala Thr Gly Gly Cys Thr Cys Thr Cys Gly
625 630 635 640

Cys Cys Gly Gly Ala Gly Thr Ala Thr Thr Cys Ala Ala Cys Ala Thr
645 650 655

Cys Gly Gly Ala Gly Ala Cys Thr Thr Cys Gly Thr Gly Cys Cys Gly
660 665 670

Thr Cys Ala Cys Thr Thr Gly Ala Thr Thr Gly Gly Thr Thr Ala Gly
675 680 685

Ala Thr Thr Thr Ala Cys Ala Ala Gly Gly Cys Gly Thr Cys Gly Cys
690 695 700

Thr Gly Gly Thr Ala Ala Ala Ala Thr Gly Ala Ala Ala Cys Gly Gly
705 710 715 720

Cys Thr Thr Cys Ala Cys Ala Ala Gly Ala Gly Ala Thr Thr Cys Gly
725 730 735

Ala Cys Gly Cys Thr Thr Thr Thr Cys Thr Ala Thr Cys Gly Thr Cys
740 745 750

Gly Ala Thr Thr Thr Thr Gly Ala Ala Ala Gly Ala Gly Cys Ala Cys
755 760 765

Gly Ala Ala Ala Thr Gly Ala Ala Cys Gly Gly Thr Cys Ala Ala Gly
770 775 780

Ala Thr Cys Ala Ala Ala Ala Gly Cys Ala Thr Ala Cys Ala Gly Ala
785 790 795 800

Thr Ala Thr Gly Cys Thr Thr Ala Gly Cys Ala Cys Thr Thr Thr Ala
805 810 815

Ala Thr Cys Thr Cys Cys Cys Thr Thr Ala Ala Ala Gly Gly Ala Ala
820 825 830

Cys Thr Gly Ala Thr Cys Thr Thr Gly Ala Cys Gly Gly Thr Gly Ala
835 840 845

Cys Gly Gly Ala Gly Gly Ala Ala Gly Cys Thr Thr Ala Ala Cys Gly
850 855 860

Gly Ala Thr Ala Cys Thr Gly Ala Gly Ala Thr Thr Ala Ala Ala Gly
865 870 875 880

Cys Cys Thr Thr Gly Cys Thr Ala Thr Thr Gly Ala Ala Cys Ala Thr
885 890 895

Gly Thr Thr Cys Ala Cys Ala Gly Cys Thr Gly Gly Ala Ala Cys Thr
900 905 910

Gly Ala Cys Ala Cys Gly Thr Cys Ala Gly Cys Ala Ala Gly Thr Ala
915 920 925

```
Cys Gly Gly Thr Gly Gly Ala Cys Thr Gly Gly Cys Thr Ala Thr
    930             935             940

Ala Gly Cys Thr Gly Ala Ala Cys Thr Thr Ala Thr Cys Cys Gly Thr
945             950             955             960

Cys Ala Cys Cys Cys Gly Gly Ala Thr Ala Thr Ala Ala Thr Gly Gly
                965             970             975

Thr Thr Ala Ala Ala Gly Cys Cys Cys Ala Ala Gly Ala Ala Gly Ala
            980             985             990

Ala Cys Thr Thr Gly Ala Thr Ala Thr Thr Gly Thr Thr Gly Thr Gly
        995             1000            1005

Gly Gly Cys Cys Gly Thr Gly Ala Cys Ala Gly Gly Cys Cys Thr
    1010            1015            1020

Gly Thr Thr Ala Ala Thr Gly Ala Ala Thr Cys Ala Gly Ala Cys
    1025            1030            1035

Ala Thr Cys Gly Cys Thr Cys Ala Gly Cys Thr Thr Cys Cys Thr
    1040            1045            1050

Thr Ala Cys Cys Thr Thr Cys Ala Gly Gly Cys Gly Gly Thr Thr
    1055            1060            1065

Ala Thr Cys Ala Ala Ala Gly Ala Gly Ala Ala Thr Thr Thr Cys
    1070            1075            1080

Ala Gly Gly Cys Thr Thr Cys Ala Thr Cys Cys Ala Cys Cys Ala
    1085            1090            1095

Ala Cys Ala Cys Cys Ala Cys Thr Cys Thr Cys Gly Thr Thr Ala
    1100            1105            1110

Cys Cys Ala Cys Ala Cys Ala Thr Cys Gly Cys Gly Thr Cys Ala
    1115            1120            1125

Gly Ala Gly Ala Gly Cys Thr Gly Thr Gly Ala Gly Ala Thr Cys
    1130            1135            1140

Ala Ala Cys Gly Gly Cys Thr Ala Cys Cys Ala Thr Ala Thr Cys
    1145            1150            1155

Cys Cys Gly Ala Ala Ala Gly Gly Ala Thr Cys Gly Ala Cys Thr
    1160            1165            1170

Cys Thr Ala Thr Thr Gly Ala Cys Gly Ala Ala Cys Ala Thr Ala
    1175            1180            1185

Thr Gly Gly Gly Cys Cys Ala Thr Ala Gly Cys Cys Cys Gly Thr
    1190            1195            1200

Gly Ala Cys Cys Cys Gly Gly Ala Thr Cys Ala Ala Thr Gly Gly
    1205            1210            1215

Thr Cys Cys Gly Ala Cys Cys Cys Gly Thr Thr Ala Gly Cys Ala
    1220            1225            1230

Thr Thr Thr Ala Ala Ala Cys Cys Cys Gly Ala Gly Ala Gly Ala
    1235            1240            1245

Thr Thr Cys Thr Thr Ala Cys Cys Cys Gly Gly Thr Gly Gly Thr
    1250            1255            1260

Gly Ala Ala Ala Ala Ala Thr Cys Cys Gly Gly Cys Gly Thr Thr
    1265            1270            1275

Gly Ala Thr Gly Thr Gly Ala Ala Gly Gly Ala Ala Gly Cys
    1280            1285            1290

Gly Ala Thr Thr Thr Cys Gly Ala Gly Cys Thr Ala Ala Thr Ala
    1295            1300            1305

Cys Cys Gly Thr Thr Cys Gly Ala Gly Cys Thr Gly Gly Gly
    1310            1315            1320

Ala Gly Gly Ala Gly Ala Ala Thr Cys Thr Gly Thr Gly Cys Cys
```

1325 1330 1335

Gly Gly Thr Thr Thr Ala Ala Gly Thr Thr Thr Ala Gly Gly Gly
1340 1345 1350

Thr Thr Ala Cys Gly Thr Ala Cys Gly Ala Thr Thr Cys Ala Gly
1355 1360 1365

Thr Thr Thr Cys Thr Thr Ala Cys Gly Gly Cys Gly Ala Cys Gly
1370 1375 1380

Thr Thr Gly Gly Thr Thr Cys Ala Ala Gly Gly Ala Thr Thr Thr
1385 1390 1395

Gly Ala Thr Thr Gly Gly Gly Ala Ala Thr Thr Ala Gly Cys Thr
1400 1405 1410

Gly Gly Ala Gly Gly Ala Gly Thr Thr Ala Cys Gly Cys Cys Gly
1415 1420 1425

Gly Ala Gly Ala Ala Gly Cys Thr Gly Ala Ala Thr Ala Thr Gly
1430 1435 1440

Gly Ala Gly Gly Ala Gly Ala Gly Thr Thr Ala Thr Gly Gly Gly
1445 1450 1455

Cys Thr Thr Ala Cys Ala Cys Thr Gly Cys Ala Ala Ala Gly Ala
1460 1465 1470

Gly Cys Gly Gly Thr Thr Cys Cys Thr Thr Thr Gly Gly Thr Gly
1475 1480 1485

Gly Thr Ala Cys Ala Thr Cys Cys Thr Ala Ala Gly Cys Cys Ala
1490 1495 1500

Ala Gly Gly Thr Thr Gly Gly Cys Thr Cys Cys Gly Ala Ala Cys
1505 1510 1515

Gly Thr Thr Thr Ala Thr Gly Gly Ala Cys Thr Cys Gly Gly Gly
1520 1525 1530

Thr Cys Gly Gly Gly Thr Thr Ala Ala
1535 1540

<210> SEQ ID NO 35
<211> LENGTH: 1704
<212> TYPE: PRT
<213> ORGANISM: Callistephus chinensis

<400> SEQUENCE: 35

Ala Thr Thr Ala Cys Ala Thr Cys Cys Cys Cys Cys Thr Cys Ala Cys
1 5 10 15

Ala Thr Gly Thr Gly Cys Ala Ala Thr Gly Ala Cys Cys Ala Thr Thr
20 25 30

Thr Thr Ala Cys Cys Cys Thr Thr Thr Ala Thr Thr Thr Thr Cys Thr
35 40 45

Ala Cys Ala Cys Ala Thr Gly Thr Ala Thr Cys Ala Cys Thr Gly Cys
50 55 60

Cys Thr Thr Ala Gly Thr Gly Cys Thr Cys Thr Ala Thr Gly Thr Ala
65 70 75 80

Thr Thr Gly Cys Thr Thr Ala Ala Cys Cys Thr Thr Thr Thr Gly Ala
85 90 95

Cys Cys Cys Gly Thr Ala Ala Cys Cys Cys Ala Ala Ala Cys Cys Gly
100 105 110

Cys Cys Thr Thr Cys Cys Cys Cys Cys Ala Gly Gly Thr Cys Cys Ala
115 120 125

Ala Cys Cys Cys Cys Ala Thr Gly Gly Cys Cys Cys Ala Thr Ala Gly
130 135 140

Thr Thr Gly Gly Ala Ala Ala Cys Cys Thr Ala Cys Cys Ala Cys Ala

-continued

```
            145                 150                 155                 160
Cys Cys Thr Thr Gly Gly Cys Ala Thr Gly Ala Thr Cys Cys Ala
                165                 170                 175
Cys Ala Cys Cys Ala Cys Thr Cys Ala Thr Thr Ala Gly Cys Gly Gly
                180                 185                 190
Cys Cys Thr Thr Gly Gly Cys Cys Ala Ala Ala Gly Thr Ala
                195                 200                 205
Thr Gly Gly Thr Cys Cys Gly Cys Thr Gly Ala Thr Cys Ala Cys
        210                 215                 220
Cys Thr Ala Cys Gly Cys Cys Thr Cys Gly Gly Thr Thr Gly
225                 230                 235                 240
Thr Thr Gly Ala Cys Gly Thr Gly Gly Thr Cys Gly Thr Gly Gly Cys
                245                 250                 255
Cys Gly Cys Gly Thr Cys Ala Gly Cys Ala Thr Cys Cys Gly Thr Thr
                260                 265                 270
Gly Cys Gly Gly Cys Ala Cys Ala Ala Thr Thr Cys Thr Ala Ala
        275                 280                 285
Ala Ala Ala Cys Thr Cys Ala Thr Gly Ala Cys Gly Cys Ala Ala
        290                 295                 300
Cys Thr Thr Thr Gly Cys Ala Ala Gly Thr Ala Gly Ala Cys Cys Ala
305                 310                 315                 320
Cys Cys Cys Ala Ala Cys Thr Cys Thr Gly Gly Ala Gly Cys Cys Ala
                325                 330                 335
Ala Gly Cys Ala Thr Ala Thr Thr Gly Cys Cys Thr Ala Thr Ala Ala
                340                 345                 350
Cys Thr Ala Thr Cys Ala Ala Gly Ala Thr Cys Thr Thr Gly Thr Gly
                355                 360                 365
Thr Thr Cys Gly Cys Ala Cys Cys Thr Thr Ala Thr Gly Gly Thr Cys
        370                 375                 380
Cys Ala Ala Gly Gly Thr Gly Gly Cys Gly Ala Ala Thr Gly Cys Thr
385                 390                 395                 400
Thr Ala Gly Gly Ala Ala Ala Thr Thr Gly Thr Thr Cys Gly
                405                 410                 415
Gly Thr Thr Cys Ala Cys Thr Thr Gly Thr Thr Thr Cys Cys Ala
                420                 425                 430
Cys Thr Ala Ala Ala Gly Cys Ala Cys Thr Ala Gly Ala Cys Gly Ala
                435                 440                 445
Cys Thr Thr Cys Cys Gly Thr Cys Ala Thr Gly Thr Thr Cys Gly Ala
                450                 455                 460
Gly Ala Gly Gly Ala Ala Gly Ala Gly Gly Thr Ala Gly Cys Gly Ala
465                 470                 475                 480
Thr Ala Cys Thr Gly Ala Cys Gly Cys Gly Ala Gly Thr Gly Thr Thr
                485                 490                 495
Ala Gly Thr Cys Thr Cys Ala Thr Gly Cys Gly Gly Gly Thr Gly Ala Ala
                500                 505                 510
Thr Cys Ala Gly Cys Gly Gly Thr Gly Ala Ala Thr Ala Gly
                515                 520                 525
Gly Ala Cys Ala Ala Cys Thr Ala Cys Thr Gly Ala Ala Cys Gly Thr
                530                 535                 540
Gly Thr Gly Cys Ala Cys Cys Ala Cys Ala Ala Cys Cys Gly
545                 550                 555                 560
Thr Thr Ala Gly Cys Ala Cys Gly Ala Gly Thr Gly Ala Thr Gly Cys
                565                 570                 575
```

-continued

```
Thr Ala Gly Gly Cys Cys Gly Gly Ala Gly Thr Thr Thr
            580                 585                 590

Cys Gly Cys Gly Gly Ala Cys Gly Cys Ala Gly Thr Gly Ala Ala
            595                 600                 605

Gly Gly Cys Cys Gly Gly Gly Ala Gly Thr Cys Gly Ala Cys Cys
            610                 615                 620

Cys Ala Ala Gly Gly Cys Ala Gly Ala Thr Gly Ala Gly Thr Thr
625                 630                 635                 640

Cys Ala Ala Gly Gly Ala Cys Ala Thr Gly Gly Thr Gly Gly Thr
                645                 650                 655

Gly Ala Ala Cys Thr Cys Ala Thr Gly Gly Ala Ala Thr Ala Gly
            660                 665                 670

Cys Cys Gly Gly Thr Gly Ala Ala Thr Thr Cys Ala Ala Cys Ala Thr
            675                 680                 685

Ala Gly Gly Thr Gly Ala Cys Thr Cys Ala Thr Ala Cys Cys Ala
            690                 695                 700

Cys Cys Ala Cys Thr Gly Ala Cys Thr Gly Cys Thr Thr Gly
705                 710                 715                 720

Ala Thr Thr Thr Gly Cys Ala Ala Gly Gly Cys Ala Thr Cys Ala Cys
            725                 730                 735

Cys Ala Ala Ala Ala Ala Gly Ala Thr Gly Ala Ala Gly Ala Ala
            740                 745                 750

Cys Thr Thr Cys Ala Thr Gly Cys Thr Cys Gly Ala Thr Thr Cys Gly
            755                 760                 765

Ala Cys Ala Ala Gly Thr Thr Thr Cys Thr Thr Ala Ala Cys Ala Thr
770                 775                 780

Cys Ala Thr Cys Thr Ala Gly Ala Cys Gly Ala Cys Cys Ala Thr
785                 790                 795                 800

Ala Ala Ala Ala Thr Cys Gly Ala Ala Ala Ala Gly Gly Cys Gly
            805                 810                 815

Cys Gly Gly Cys Cys Gly Gly Cys Cys Gly Cys Cys Gly Thr Cys Ala
            820                 825                 830

Thr Ala Gly Thr Gly Ala Cys Thr Thr Gly Cys Thr Gly Ala Cys Cys
            835                 840                 845

Ala Cys Gly Cys Thr Gly Ala Thr Thr Thr Cys Ala Cys Thr Cys Ala
            850                 855                 860

Ala Gly Gly Ala Thr Gly Thr Thr Gly Ala Thr Cys Thr Gly Cys
865                 870                 875                 880

Thr Gly Ala Thr Gly Ala Thr Gly Ala Thr Ala Ala Gly Ala Ala
            885                 890                 895

Gly Gly Gly Ala Ala Cys Thr Thr Thr Cys Ala Gly Ala Cys Ala
            900                 905                 910

Thr Thr Gly Ala Ala Ala Thr Cys Ala Ala Gly Gly Cys Thr Thr Thr
            915                 920                 925

Gly Cys Thr Cys Cys Thr Gly Ala Ala Cys Thr Thr Ala Thr Thr Thr
            930                 935                 940

Gly Cys Thr Gly Cys Ala Gly Gly Ala Ala Cys Ala Gly Ala Cys Ala
945                 950                 955                 960

Cys Ala Thr Cys Ala Thr Cys Thr Ala Gly Thr Ala Cys Cys Gly Thr
            965                 970                 975

Gly Gly Ala Ala Thr Gly Gly Gly Cys Ala Gly Thr Ala Gly Cys Cys
            980                 985                 990

Gly Ala Ala Cys Thr Thr Ala Thr  Thr Cys Gly Thr Cys  Ala Thr Cys
            995                 1000                1005
```

Cys Gly Gly Ala Ala Cys Thr Ala Thr Thr Gly Ala Ala Ala Cys
1010 1015 1020

Ala Ala Gly Cys Ala Cys Gly Cys Gly Ala Ala Gly Ala Ala Ala
1025 1030 1035

Thr Gly Gly Ala Thr Ala Thr Cys Gly Thr Ala Gly Thr Thr Gly
1040 1045 1050

Gly Thr Cys Gly Ala Gly Ala Cys Cys Gly Gly Cys Thr Thr Gly
1055 1060 1065

Thr Ala Ala Cys Cys Gly Ala Ala Thr Thr Gly Gly Ala Cys Thr
1070 1075 1080

Thr Ala Ala Gly Cys Cys Gly Gly Cys Thr Ala Ala Cys Ala Thr
1085 1090 1095

Thr Cys Cys Thr Ala Cys Ala Ala Gly Cys Cys Ala Thr Thr Gly
1100 1105 1110

Thr Gly Ala Ala Gly Gly Ala Gly Ala Cys Cys Thr Thr Thr Ala
1115 1120 1125

Gly Gly Cys Thr Cys Cys Ala Cys Cys Cys Thr Thr Cys Gly Ala
1130 1135 1140

Cys Gly Cys Cys Ala Cys Thr Cys Thr Cys Cys Cys Thr Thr Cys
1145 1150 1155

Cys Ala Ala Gly Gly Ala Thr Gly Gly Cys Gly Thr Cys Gly Gly
1160 1165 1170

Ala Gly Ala Gly Thr Thr Gly Cys Gly Ala Gly Gly Thr Gly Gly
1175 1180 1185

Ala Thr Gly Gly Gly Thr Ala Cys Thr Ala Cys Ala Thr Thr Cys
1190 1195 1200

Cys Cys Ala Ala Ala Gly Gly Ala Thr Cys Cys Ala Cys Ala Cys
1205 1210 1215

Thr Cys Cys Thr Thr Gly Thr Thr Ala Ala Thr Gly Thr Ala Thr
1220 1225 1230

Gly Gly Gly Cys Cys Ala Thr Ala Gly Cys Cys Cys Gly Cys Gly
1235 1240 1245

Ala Cys Cys Cys Ala Ala Ala Ala Ala Thr Gly Thr Gly Gly Ala
1250 1255 1260

Cys Thr Ala Ala Cys Cys Cys Ala Cys Thr Thr Gly Ala Gly Thr
1265 1270 1275

Thr Cys Ala Gly Gly Cys Cys Cys Ala Gly Thr Cys Gly Gly Thr
1280 1285 1290

Thr Cys Thr Thr Ala Cys Cys Cys Gly Gly Gly Gly Gly Thr Gly
1295 1300 1305

Ala Ala Ala Ala Gly Cys Cys Cys Gly Ala Thr Gly Cys Ala Gly
1310 1315 1320

Ala Thr Ala Thr Cys Ala Ala Ala Gly Gly Ala Ala Ala Thr Gly
1325 1330 1335

Ala Thr Thr Thr Thr Gly Ala Gly Gly Thr Cys Ala Thr Ala Cys
1340 1345 1350

Cys Ala Thr Thr Thr Gly Gly Gly Gly Cys Cys Gly Gly Gly Ala
1355 1360 1365

Gly Ala Ala Gly Ala Ala Thr Ala Thr Gly Thr Gly Cys Gly Gly
1370 1375 1380

Gly Thr Ala Thr Gly Ala Gly Cys Cys Thr Ala Gly Gly Gly Ala
1385 1390 1395

Thr Gly Ala Gly Ala Ala Thr Gly Gly Thr Cys Cys Ala Gly Thr

```
                1400                1405                1410
Thr Gly Cys Thr Cys Ala Thr Gly Cys Ala Ala Cys Ala Thr
        1415                1420                1425
Thr Gly Gly Thr Cys Ala Ala Ala Cys Cys Thr Thr Thr Gly
1430                1435                1440
Ala Thr Thr Gly Gly Gly Ala Ala Thr Gly Gly Cys Thr Ala
    1445                1450                1455
Ala Thr Gly Gly Gly Thr Thr Ala Gly Ala Cys Cys Gly Gly
    1460                1465                1470
Ala Gly Ala Ala Gly Cys Thr Cys Ala Ala Cys Ala Thr Gly Gly
    1475                1480                1485
Ala Ala Gly Ala Ala Gly Cys Thr Thr Ala Cys Gly Gly Gly Cys
    1490                1495                1500
Thr Ala Ala Cys Cys Cys Thr Thr Cys Ala Ala Ala Gly Gly Gly
    1505                1510                1515
Cys Thr Gly Ala Ala Cys Cys Cys Thr Thr Ala Ala Thr Gly Gly
1520                1525                1530
Thr Gly Cys Ala Cys Cys Ala Ala Gly Gly Cys Cys Cys Ala
    1535                1540                1545
Gly Gly Cys Thr Ala Thr Cys Thr Cys Cys Cys Ala Thr Gly
    1550                1555                1560
Thr Ala Thr Ala Thr Gly Ala Ala Ala Gly Thr Cys Gly Thr Thr
    1565                1570                1575
Ala Ala Gly Gly Ala Cys Thr Ala Ala Ala Cys Gly Gly Ala
    1580                1585                1590
Thr Thr Thr Thr Gly Gly Thr Gly Thr Thr Thr Gly Gly Thr
    1595                1600                1605
Thr Ala Gly Cys Cys Ala Ala Gly Thr Thr Gly Gly Ala Ala Ala
    1610                1615                1620
Thr Thr Cys Gly Gly Cys Ala Thr Thr Thr Gly Thr Ala Thr Thr
    1625                1630                1635
Thr Cys Ala Ala Ala Thr Gly Ala Thr Thr Ala Thr Gly Gly Ala
    1640                1645                1650
Ala Ala Gly Thr Ala Ala Thr Gly Thr Cys Thr Thr Thr Gly Cys
    1655                1660                1665
Thr Cys Thr Thr Cys Gly Ala Ala Thr Thr Gly Thr Thr Gly Gly
    1670                1675                1680
Thr Ala Ala Ala Ala Ala Ala Ala Ala Ala Ala Ala Ala Ala
    1685                1690                1695
Ala Ala Ala Ala Ala Ala
    1700

<210> SEQ ID NO 36
<211> LENGTH: 508
<212> TYPE: PRT
<213> ORGANISM: Cosmos sulphureus

<400> SEQUENCE: 36

Met Thr Ile Leu Pro Leu Leu Leu Tyr Pro Ser Leu Thr Ala Leu Leu
1               5                   10                  15

Leu Tyr Val Leu Leu Asn Leu Arg Pro Arg His Pro Asn Arg Leu Pro
            20                  25                  30

Pro Gly Pro Ser Pro Trp Pro Ile Val Gly Asn Leu Pro His Leu Gly
        35                  40                  45

Thr Thr Pro His His Ser Leu Ala Ala Leu Ala Ala Lys Tyr Gly Pro
```

```
            50                  55                  60
Leu Met His Leu Arg Leu Gly Phe Val Asp Val Val Ala Ala Ser
 65                  70                  75                  80

Ala Ser Val Ala Ser Gln Phe Leu Lys Thr His Asp Ala Asn Phe Ala
                 85                  90                  95

Ser Arg Pro Pro Asn Ser Gly Ala Glu His Met Ala Tyr Asn Tyr Gln
                100                 105                 110

Asp Leu Val Phe Ala Pro Tyr Gly Pro Arg Trp Arg Met Leu Arg Lys
                115                 120                 125

Ile Cys Ser Val His Leu Phe Ser Gly Lys Ala Leu Asp Asp Phe Arg
            130                 135                 140

His Val Arg Gln Glu Glu Val Ala Val Leu Thr Arg Ala Leu Ala Gly
145                 150                 155                 160

Ala Gly Lys Ser Pro Val Lys Leu Gly Gln Leu Leu Ser Val Cys Thr
                165                 170                 175

Thr Asn Ala Leu Ala Arg Val Met Leu Gly Arg Arg Val Phe Gly Glu
            180                 185                 190

Arg Asp Ala Lys Ala Asp Glu Phe Lys Asp Met Val Val Glu Met Met
                195                 200                 205

Val Leu Ala Gly Glu Phe Asn Ile Gly Asp Phe Ile Pro Ala Leu Asp
210                 215                 220

Trp Leu Asp Leu Gln Gly Ile Thr Lys Met Lys Lys Leu His Ala
225                 230                 235                 240

Gln Phe Asp Ser Phe Leu Asn Thr Ile Leu Glu Glu His Lys Thr Gly
                245                 250                 255

Lys Gly Gly Ser Ser Ser His Arg Asp Leu Ser Ser Thr Leu Ile Ala
                260                 265                 270

Leu Lys Asp Asp Ala Asp Gly Glu Gly Lys Leu Ser Asp Ile Glu
            275                 280                 285

Ile Lys Ala Leu Leu Asn Leu Phe Ile Ala Gly Thr Asp Thr Ser
            290                 295                 300

Ser Ser Thr Val Glu Trp Ala Ile Ala Glu Leu Ile Arg Cys Pro Gln
305                 310                 315                 320

Ile Leu Arg Gln Ala His Glu Glu Met Asp Asn Val Val Gly Arg Glu
                325                 330                 335

Arg Leu Val Thr Glu Ser Asp Leu Gly Lys Leu Thr Phe Leu Gln Ala
                340                 345                 350

Ile Val Lys Glu Thr Phe Arg Leu His Pro Ser Thr Pro Leu Ser Leu
            355                 360                 365

Pro Arg Ile Ala Ser Glu Ser Cys Glu Ile Asp Gly Tyr Phe Ile Pro
370                 375                 380

Lys Gly Ser Thr Leu Leu Val Asn Val Trp Ala Ile Ala Arg Asp Pro
385                 390                 395                 400

Lys Met Trp Thr Asp Pro Leu Glu Phe Arg Pro Thr Arg Phe Leu Pro
                405                 410                 415

Gly Gly Glu Lys Pro Asn Val Asp Val Lys Gly Asn Asp Phe Glu Val
                420                 425                 430

Ile Pro Phe Gly Ala Gly Arg Arg Ile Cys Val Gly Ile Ser Leu Gly
            435                 440                 445

Leu Arg Met Val Gln Leu Leu Val Ala Thr Leu Val Gln Thr Phe Asp
            450                 455                 460

Trp Glu Leu Ala Asn Gly Val Leu Pro Glu Lys Leu Asn Met Asn Glu
465                 470                 475                 480
```

```
Ala Phe Gly Leu Thr Leu Gln Arg Ala Glu Pro Leu Ile Val Tyr Pro
                485                 490                 495

Lys Pro Arg Leu Ala Pro His Val Tyr Glu Ser Gly
        500                 505

<210> SEQ ID NO 37
<211> LENGTH: 23
<212> TYPE: PRT
<213> ORGANISM: Cosmos sulphureus

<400> SEQUENCE: 37

Ser Arg Pro Leu Ser Ser Gly Gly Lys Tyr Ile Ala Tyr Asn Tyr Gln
1               5                   10                  15

Asp Met Val Phe Ala Pro Tyr
            20

<210> SEQ ID NO 38
<211> LENGTH: 16
<212> TYPE: PRT
<213> ORGANISM: Cosmos sulphureus

<400> SEQUENCE: 38

Arg Arg Val Phe Ala Asp Gly Ser Ala Gly Gly Asp Pro Lys Ala Asp
1               5                   10                  15

<210> SEQ ID NO 39
<211> LENGTH: 21
<212> TYPE: PRT
<213> ORGANISM: Cosmos sulphureus

<400> SEQUENCE: 39

Asp Val Gln Gly Asn Asn Phe Glu Val Ile Pro Phe Gly Ala Gly Arg
1               5                   10                  15

Arg Ile Cys Val Gly
            20

<210> SEQ ID NO 40
<211> LENGTH: 23
<212> TYPE: PRT
<213> ORGANISM: Cosmos sulphureus

<400> SEQUENCE: 40

Ser Arg Pro Pro Asn Ser Gly Ala Glu His Met Ala Tyr Asn Tyr Gln
1               5                   10                  15

Asp Leu Val Phe Ala Pro Tyr
            20

<210> SEQ ID NO 41
<211> LENGTH: 12
<212> TYPE: PRT
<213> ORGANISM: Cosmos sulphureus

<400> SEQUENCE: 41

Arg Arg Val Phe Gly Glu Arg Asp Ala Lys Ala Asp
1               5                   10

<210> SEQ ID NO 42
<211> LENGTH: 21
<212> TYPE: PRT
<213> ORGANISM: Cosmos sulphureus

<400> SEQUENCE: 42

Asp Val Lys Gly Asn Asn Phe Glu Val Ile Pro Phe Gly Ala Gly Arg
1               5                   10                  15
```

Arg Ile Cys Val Gly
        20

<210> SEQ ID NO 43
<211> LENGTH: 23
<212> TYPE: PRT
<213> ORGANISM: Dahlia variabilis

<400> SEQUENCE: 43

Ser Arg Pro Pro Asn Ser Gly Ala Lys His Ile Ala Tyr Asn Tyr Gln
1               5                   10                  15

Asp Leu Val Phe Ala Pro Tyr
        20

<210> SEQ ID NO 44
<211> LENGTH: 13
<212> TYPE: PRT
<213> ORGANISM: Cosmos sulphureus

<400> SEQUENCE: 44

Arg Arg Val Phe Gly Asp Thr Gly Asp Leu Lys Ala Asp
1               5                   10

<210> SEQ ID NO 45
<211> LENGTH: 21
<212> TYPE: PRT
<213> ORGANISM: Cosmos sulphureus

<400> SEQUENCE: 45

Asp Val Lys Gly Asn Asp Phe Glu Val Ile Pro Phe Gly Ala Gly Arg
1               5                   10                  15

Arg Ile Cys Val Gly
        20

<210> SEQ ID NO 46
<211> LENGTH: 23
<212> TYPE: PRT
<213> ORGANISM: Targetes erecta

<400> SEQUENCE: 46

Ser Arg Pro Pro Asn Ser Gly Ala Lys His Ile Ala Tyr Asn Tyr Gln
1               5                   10                  15

Asp Leu Val Phe Ala Pro Tyr
        20

<210> SEQ ID NO 47
<211> LENGTH: 13
<212> TYPE: PRT
<213> ORGANISM: Targetes erecta

<400> SEQUENCE: 47

Arg Arg Val Phe Gly Asp Thr Gly Asp Leu Lys Ala Asp
1               5                   10

<210> SEQ ID NO 48
<211> LENGTH: 21
<212> TYPE: PRT
<213> ORGANISM: Targetes erecta

<400> SEQUENCE: 48

Asp Val Lys Gly Asn Asp Phe Glu Val Ile Pro Phe Gly Ala Gly Arg
1               5                   10                  15

Arg Ile Cys Val Gly

<210> SEQ ID NO 49
<211> LENGTH: 23
<212> TYPE: PRT
<213> ORGANISM: Rudbeckia hirta

<400> SEQUENCE: 49

Ser Arg Pro Pro Asn Ser Gly Ala Lys His Ile Ala Tyr Asn Tyr Gln
1               5                   10                  15

Asp Leu Val Phe Ala Pro Tyr
            20

<210> SEQ ID NO 50
<211> LENGTH: 13
<212> TYPE: PRT
<213> ORGANISM: Rudbeckia hirta

<400> SEQUENCE: 50

Arg Arg Val Phe Ser Asp Thr Ser Asp Leu Lys Ala Asp
1               5                   10

<210> SEQ ID NO 51
<211> LENGTH: 21
<212> TYPE: PRT
<213> ORGANISM: Rudbeckia hirta

<400> SEQUENCE: 51

Asp Val Lys Gly Asn Asp Phe Glu Val Ile Pro Phe Gly Ala Gly Arg
1               5                   10                  15

Arg Ile Cys Val Gly
            20

<210> SEQ ID NO 52
<211> LENGTH: 23
<212> TYPE: PRT
<213> ORGANISM: Echinops bannaticus

<400> SEQUENCE: 52

Ser Arg Pro Pro Asn Ser Gly Ala Lys His Met Ala Tyr Asn Tyr Gln
1               5                   10                  15

Asp Met Val Phe Ala Pro Tyr
            20

<210> SEQ ID NO 53
<211> LENGTH: 16
<212> TYPE: PRT
<213> ORGANISM: Echinops bannaticus

<400> SEQUENCE: 53

Arg Arg Val Phe Gly Asp Gly Ser Gly Gly Asp Ser Lys Ser Asp
1               5                   10                  15

<210> SEQ ID NO 54
<211> LENGTH: 21
<212> TYPE: PRT
<213> ORGANISM: Echinops bannaticus

<400> SEQUENCE: 54

Asp Val Lys Gly Asn Asp Phe Glu Leu Ile Pro Phe Gly Ala Gly Arg
1               5                   10                  15

Arg Ile Cys Ala Gly
            20

<210> SEQ ID NO 55
<211> LENGTH: 23
<212> TYPE: PRT
<213> ORGANISM: Centaurea cyanus

<400> SEQUENCE: 55

Ser Arg Pro Pro Asn Ser Gly Ala Lys His Leu Ala Tyr Asp Tyr Gln
1               5                   10                  15

Asp Leu Val Phe Ala Pro Tyr
            20

<210> SEQ ID NO 56
<211> LENGTH: 16
<212> TYPE: PRT
<213> ORGANISM: Centaurea cyanus

<400> SEQUENCE: 56

Arg Arg Val Phe Gly Asp Gly Ser Gly Gly Asp Pro Lys Ala Asp
1               5                   10                  15

<210> SEQ ID NO 57
<211> LENGTH: 21
<212> TYPE: PRT
<213> ORGANISM: Centaurea cyanus

<400> SEQUENCE: 57

Asn Val Lys Gly Asn Asp Phe Glu Ile Ile Pro Phe Gly Ala Gly Arg
1               5                   10                  15

Arg Ile Cys Ala Gly
            20

<210> SEQ ID NO 58
<211> LENGTH: 23
<212> TYPE: PRT
<213> ORGANISM: Gerbera hybrida

<400> SEQUENCE: 58

Asp Arg Pro Pro Asn Ser Gly Ala Lys His Ile Ala Tyr Asn Tyr Gln
1               5                   10                  15

Asp Leu Val Phe Ala Pro Tyr
            20

<210> SEQ ID NO 59
<211> LENGTH: 12
<212> TYPE: PRT
<213> ORGANISM: Gerbera hybrida

<400> SEQUENCE: 59

Arg Arg Val Glu Asp Ser Gly Asp Ala Gln Ala Asp
1               5                   10

<210> SEQ ID NO 60
<211> LENGTH: 21
<212> TYPE: PRT
<213> ORGANISM: Gerbera hybrida

<400> SEQUENCE: 60

Asp Ile Lys Gly Asn Asp Phe Glu Val Ile Pro Phe Gly Ala Gly Arg
1               5                   10                  15

Arg Ile Cys Val Gly
            20

<210> SEQ ID NO 61

```
<211> LENGTH: 23
<212> TYPE: PRT
<213> ORGANISM: Osteospermum hybrida

<400> SEQUENCE: 61

Ser Arg Pro Pro Asn Ser Gly Ala Lys His Met Ala Tyr Asn Tyr Gln
1               5                   10                  15

Asp Leu Val Phe Ala Pro Tyr
            20

<210> SEQ ID NO 62
<211> LENGTH: 12
<212> TYPE: PRT
<213> ORGANISM: Osteospermum hybrida

<400> SEQUENCE: 62

Arg Arg Val Phe Asp Ser Gly Asp Ala Gln Ala Asp
1               5                   10

<210> SEQ ID NO 63
<211> LENGTH: 21
<212> TYPE: PRT
<213> ORGANISM: Osteospermum hybrida

<400> SEQUENCE: 63

Asp Ile Lys Gly Asn Asp Phe Glu Val Ile Pro Phe Gly Ala Gly Arg
1               5                   10                  15

Arg Ile Cys Val Gly
            20

<210> SEQ ID NO 64
<211> LENGTH: 23
<212> TYPE: PRT
<213> ORGANISM: Cichorium intvbus

<400> SEQUENCE: 64

Ser Arg Pro Pro Asn Ser Gly Ala Lys His Met Ala Tyr Asn Tyr Gln
1               5                   10                  15

Asp Leu Val Phe Ala Pro Tyr
            20

<210> SEQ ID NO 65
<211> LENGTH: 16
<212> TYPE: PRT
<213> ORGANISM: Cichorium intybus

<400> SEQUENCE: 65

Arg Arg Val Phe Gly Asp Gly Ser Gly Gly Gly Asp Pro Lys Ala Asp
1               5                   10                  15

<210> SEQ ID NO 66
<211> LENGTH: 21
<212> TYPE: PRT
<213> ORGANISM: Cichorium intvbus

<400> SEQUENCE: 66

Asp Val Lys Gly Asn Asp Phe Glu Val Ile Pro Phe Gly Ala Gly Arg
1               5                   10                  15

Arg Ile Cys Ala Gly
            20

<210> SEQ ID NO 67
<211> LENGTH: 23
<212> TYPE: PRT
```

<213> ORGANISM: Antirrhinum majus

<400> SEQUENCE: 67

Ser Arg Pro Pro Asn Ser Gly Ala Lys His Val Ala Tyr Asn Tyr Gln
1               5                   10                  15

Asp Leu Val Phe Ala Pro Tyr
            20

<210> SEQ ID NO 68
<211> LENGTH: 12
<212> TYPE: PRT
<213> ORGANISM: Antirrhinum majus

<400> SEQUENCE: 68

Arg Arg Val Val Gly His Ala Asp Ser Lys Ala Glu
1               5                   10

<210> SEQ ID NO 69
<211> LENGTH: 21
<212> TYPE: PRT
<213> ORGANISM: Antirrhinum majus

<400> SEQUENCE: 69

Asp Val Pro Gly Asn Asp Phe Glu Leu Ile Pro Phe Gly Ala Gly Arg
1               5                   10                  15

Arg Ile Cys Ala Gly
            20

<210> SEQ ID NO 70
<211> LENGTH: 23
<212> TYPE: PRT
<213> ORGANISM: Arabidopsis thaliana

<400> SEQUENCE: 70

Ser Arg Pro Pro Asn Ser Gly Ala Lys His Met Ala Tyr Asn Tyr Gln
1               5                   10                  15

Asp Leu Val Phe Ala Pro Tyr
            20

<210> SEQ ID NO 71
<211> LENGTH: 13
<212> TYPE: PRT
<213> ORGANISM: Arabidopsis thaliana

<400> SEQUENCE: 71

Arg Arg Leu Phe Gly Ala Asp Ala Asp His Lys Ala Asp
1               5                   10

<210> SEQ ID NO 72
<211> LENGTH: 21
<212> TYPE: PRT
<213> ORGANISM: Arabidopsis thaliana

<400> SEQUENCE: 72

Asp Val Lys Gly Ser Asp Phe Glu Leu Ile Pro Phe Gly Ala Gly Arg
1               5                   10                  15

Arg Ile Cys Ala Gly
            20

<210> SEQ ID NO 73
<211> LENGTH: 1601
<212> TYPE: DNA
<213> ORGANISM: Cosmos sulphureus -continued

<400> SEQUENCE: 73

```
atgactattc taccccctact actctaccct tccctaactg ccttactact gtacgtactt      60
cttaacctgc gcccccgtca ccctaaccgt ctcccgccgg gaccaagccc atggccgatc     120
gtcggaaacc taccgcacct cggcacaact ccgcatcact cgcttgcggc attggcggca     180
aagtacggcc cgttgatgca cctccgactc ggctttgttg acgtggtcam gccgcctctg     240
cgtcagtcgc ttcacagttt ttgaaaactc atgacgcgaa tttcgccagc cggccgccga     300
actccggcgc ggagcatatg gcgtataatt atcaggatct ggtgtttgcg ccgtacggtc     360
ctcggtggcg gatgcttcgg aagatatcct ccgtgcacct atttttccggc aaagcactcg    420
atgacttccg tcatgttcgg caggaggaag tagcggtact gacgcgcgct ttagccggtg     480
cggggaaatc accggtgaaa ttaggtcaac tgcttagcgt gtgcaccacc aacgcattag     540
cacgagtgat gttaggcagg agagtattcg gtgagcgtga tgcgaaggcg gatgagttca     600
aggatatggt ggtggagatg atggtgttgg cgggagaatt caatatcggt gactttatcc     660
cggcgcttga ctggctggac ctgcaaggca tcacgaaaaa aatgaagaag ctgcacgctc     720
aattcgattc gtttcttaac acgattcttg aagagcataa aaccggcaag gcggctcttt    780
cgagtcacag ggatttgtcg agcacgctga ttgcactcaa ggatgatgcc gatggagagg     840
gagggaaact ttcagatatt gaaatcaaag ctttgcttct gaacttattc attgcgggaa     900
cagatacatc atctagcacc gtggaatggg caatagctga actaattcgc tgtccacaaa     960
tactacggca agcacacgaa gaaatggaca atgttgttgg tcgagagcgg cttgtaaccg    1020
aatcagacct tggtaaacta acattcctcc aagccattgt aaaggagacc tttagactcc    1080
acccgtctac accactctca ttgccaagaa ttgcgtccga gagttgtgaa attgatggct    1140
atttcattcc taagggggtcc acacttcttg ttaatgtgtg ggccattgcc cgtgacccaa    1200
aaatgtggac ggatccactt gaatttaggc ccacacggtt cttgcccgga ggtgaaaaac    1260
ccaatgttga tgttaaagga aatgacttcg aggttatacc atttggggcc ggacgaagga    1320
tttgtgtggg tattagccta gggttgagaa tggtccagtt gcttgtcgct acgctagtcc    1380
aaaccttga ctgggaattg gctaacgggg tactacccga gaagctcaac atgaatgaag    1440
cgtttgggct aacccttcaa agagccgagc ccttgatagt gtacccgaag ccgaggctag    1500
ctcctcacgt atatgaaagt ggttaaggac taaatttccg tttgaaaatt aaataaattt    1560
gtatttctgt tttggtttat tgttgtaagt tgagacatcc t                         1601
```

<210> SEQ ID NO 74
<211> LENGTH: 1645
<212> TYPE: DNA
<213> ORGANISM: Dahlia variabilis

<400> SEQUENCE: 74

```
atggccattc taaccctact actttacacc tccatcactt cccccgtgct gtacctcctg      60
cttaacctgc gcaccccgtca ccctaaccgt ctccctcccg gcccaacccc atggccgatc    120
gtcggaaacc tcccgcacct cggcacaatt ccgcaccact cgctagcgcg gctggcggta    180
aagtacggcc cgttgatgca cctccggctc ggcttcgttg acgtggtggt cgccgcctcg     240
gcgtccgtcg ctgctcagtt tttaaaaact aatgacgcga ttttcgccag ccggccgccg    300
aactccggcg cgaagcatat cgcgtataac taccaggatc tggtgtttgc accgtacggt    360
ccgcggtggc ggatgctgcg gaagatctgc tcggtgcacc ttttctccgc caaagccctc     420
gatgatttcc gtcatattcg acaggaggag gtggcgatac tcacacgtgc tttgatcggc    480
```

```
gccggagaat caacggtgaa actaggtcaa ctactcaacg tgtgcaccac aaacgcatta      540
gcgcgtgtga tgttaggtag gagagtgttc ggcgacaccg gtgatctaaa ggcggatgag      600
tttaaagata tggtggttca gctgatggtg ttggccggag aatttaacat tggtgacttt      660
atcccggcgc ttgactggct ggacatgcaa ggcattgcga agaagatgaa gaaactccat      720
gctcaatttg attcgttcct taacgcgatc cttgaagaac ataaatccgg caatggccgc      780
acgtcgggtc acggtgactt gctgagcacg ctgatcgcac tcaaggatga tgctgacggt      840
gagggtggga aactttcaga tattgaaatc aaagctttgt tactgaactt attcgttgca      900
ggaacagaca cgtcatctag cacagtggaa tgggcaatag ccgaactcat tcgccatcca      960
cgaatgctaa acaagccca agaagaaatg gacaacgtag ttggccgaga ccggcttgta     1020
tccgaatctg atctcagcca actaccattc ctccaagcca ttgtaaagga gacctttaga     1080
ctcgacccct caacaccct ctccttgcca agaatctcat ccgagaattg cgaagttgac     1140
gggtatcaca ttccaaaagg atccacactc ctcgtcaatg tgtgggccat tgctcgtgac     1200
ccaaagatgt gggcggaccc acttgagttc cgccccgcac ggttcttgcc tggaggcgaa     1260
aagcccaatg ttgatgtgaa agggaatgat tttgaagtta taccgttcgg ggctggacga     1320
aggatttgtg tgggtattag cctcgggttg aggatggtcc agttgcttgt tgcaacgtcg     1380
gtccagacct tcgattggga attagctaac gggttaaagc cggagaagct caacatgaat     1440
gaagcttatg ggctaaccct tcaaagagaa gagcccttgg tggtgcaccc aaagccgagg     1500
ttagctcctc atgtatatga aagtggttaa agattgacta gttgtcgttt ggaaaattga     1560
tagctttcaa ttaaacaggt tatgtttgtt gtatctacgt tgtacgttaa ttgttttaag     1620
ttgagaacac ccaatttgta atggg                                          1645

<210> SEQ ID NO 75
<211> LENGTH: 1700
<212> TYPE: DNA
<213> ORGANISM: Targetes erecta

<400> SEQUENCE: 75
atgtccattc taaccctact actttacacc tccatcactt cccccgtgct gtacctcctg       60
cttaacctgc gcacccgtca ccctaaccgt ctccctcccg gcccaacccc atggccgatc      120
gtcggaaacc tcccgcacct cggcacaatt ccgcaccact cgctagcgcg gctggcggta      180
aagtacggcc cgttgatgca cctccgcctc ggcttcgttg acgtggtggt cgccgcctcg      240
gcgtccgtcg ctgctcagtt ttaaaaaact aatgacgcga ttttcgccag ccggccgccg      300
aactccggcg cgaagcatat cgcgtataac taccaggatc tggtgtttgc accgtacggt      360
ccgcggtggc ggatgctgcg gaagatctgc tcggtgcacc ttttctccgc caaagccctc      420
gatgatttcc gtcatattcg acaggaggag gtggcgatac tcacacgtgc tttgatcggc      480
gccggagaat caacggtgaa actaggtcaa ctactcaacg tgtgcaccac aaacgcatta      540
gcgcgtgtga tgttaggtag gagagtgttc ggcgacaccg gtgatctaaa ggcggatgag      600
tttaaagata tggtggttca gctgatggtg ttggccggag aatttaacat tggtgacttt      660
atcccggcgc ttgactggct ggacatgcaa ggcattacga agaagatgaa gaaactccat      720
gctcaatttg attcgttcct taacgcgatt cttgaagaac ataaatccg gcatggccgc      780 acgtcgggtc acggtgactt gctgagcacg ctgatcgcac tcaaggatga tgctgacggt      840
gagggtggga aactttcaga tattgaaatc aaagctttgt tactgaactt attcgttgca      900
ggaacagaca cgtcatctag cacagtggaa tgggcaatag ccgaactcat tcgccatcca      960
```

| | |
|---|---|
| cgaatgctaa aacaagccca agaagaaatg gacaacgtag ttggccgaga ccggcttgta | 1020 |
| tccgaatctg atctcagcca actaccattc ctccaagcca ttgtaaagga gacctttaga | 1080 |
| ctccacccct caacacccct ctccttgcca agaatctcat ccgagaattg cgaagttgac | 1140 |
| gggtatcaca ttccaaaagg atccacactc ctcgtcaatg tgtgggccat tgctcgtgac | 1200 |
| ccaaagatgt gggcggaccc acttgagttc cgccccacac ggttcttgcc tggaggcgaa | 1260 |
| aagcccaatt tgatgtgaa agggaatgat tttgaagtta taccgttcgg ggctgggcga | 1320 |
| aggatttgtg tgggtattag cctcgggttg aggatggtcc agttgcttgt tgcaacgttg | 1380 |
| gtccagacct tcgattggga attagctaac gggttaaagc cggagaagct caacatgaat | 1440 |
| gaagcttatg ggctaacccct tcaaagagaa gagcccttgg tggtgcaccc aaagccgagg | 1500 |
| ttagctcctc atgtatatga aagtggttar agattgacta gttgtcgttt ggaaaattga | 1560 |
| taactttcaa ttaaacaggt tatgtttgtt gtatctacgt tgtacgttaa ttgtttttaag | 1620 |
| ttgagaacac ccaatttggg atgggttata tattcgttaa gttaataata aaataaatat | 1680 |
| tgcataaaaa aaaaaaaaaa | 1700 |

<210> SEQ ID NO 76
<211> LENGTH: 1625
<212> TYPE: DNA
<213> ORGANISM: Rudbeckia hirta
<220> FEATURE:
<221> NAME/KEY: misc_feature
<222> LOCATION: (1204)..(1204)
<223> OTHER INFORMATION: n is a, c, g, or t

<400> SEQUENCE: 76

| | |
|---|---|
| atggccattc taaccctact actttacacc tccatcactt ccctcgtgct gtacctcctg | 60 |
| cttaacctgc gcacccgtca ccctaaccgt ctcccacccg gcccaacccc atggccgatc | 120 |
| gtcggaaacc tcccgcacct cggtacaatt ccacaccact cgctagcgcg gttggccgca | 180 |
| aagtacggcc cgttgatgca cctccgcctc ggcttcgttg acgtggtggt cgcggcctcg | 240 |
| gcgtccgtcg ctgctcagtt tttgaaaact aatgacgcga ttttcgccag ccggccgccg | 300 |
| aactccggcg cgaagcatat cgcgtataac taccaggatc tggtgtttgc accatacggt | 360 |
| ccgcggtggc ggatgctgcg gaagatctgc tcggtgcacc ttttctccgc caaagcactc | 420 |
| gatgatttcc gtcatattcg acaggaggag gtggcgatac tcacgcgtgc tttgatcggc | 480 |
| gccggagaat caacggtgaa actaggtcaa ctactcaacg tgtgcaccac aaacgcatta | 540 |
| gcgcgtgtga tgttaggcag gagagtgttc agcgacaccg tgatctaaa ggcggatgag | 600 |
| tttaaagata tggtggttca gctgatggtg ttggccggag aatttaacat tggtgacttt | 660 |
| atcccggcgc ttgactggct ggacattcaa ggcattacga agaagatgaa gaaactccat | 720 |
| gctcaatttg attcgttcct taacgcgatc cttgaagaac ataaatccgg caatggccgc | 780 |
| acgtcgggtc acggtgactt gctgagcacg ctgatcgcac tcaaggatga tgctgacggt | 840 |
| gagggtggga aactttcaga tattgaaatc aaagctttgc tactgaactt attcgttgca | 900 |
| ggaacagaca cgtcatctag cacagtggaa tgggcaatag ccgaactcat cgccatcca | 960 |
| cgaatgctaa aacaagccca agaagaaatg gacaacgtag ttggccgaga ccggcttgta | 1020 |
| tccgaatctg atctcggcca actaccattc ctccaagcca ttgtaaagga gacctttaga | 1080 |
| ctccacccct caacacccct ctccttgcca agaatctcat ccgagaattg cgaagttgac | 1140 |
| gggtatcaca ttccaaaagg atccacactc cttgtcaacg tgtgggccat tgctcgtgac | 1200 |
| ccanagatgt gggcggaccc acttgagttc cgccccacac ggttcttgcc tggaggcgaa | 1260 |

```
aagcccaatg ttgatgtgaa agggaatgat tttgaagtta taccgttcgg ggctggacga    1320
aggatttgtg tgggtattag cctcgggttg aggatggtcc aattgcttgt tgcaacgttg    1380
gtccagacct tcgattggga attggctaac gggttagagc cggagaagct caacatgaat    1440
gaagcttatg gctaacccct tcaaagagaa gagcccttga tggtgcaccc aaagccgagg    1500
ttagctcctc atgtatatga aagtggttaa ggactgacta gttgtcactt tcaataaaac    1560
aggttgtttg ctgtatctac gttgtacgtt aatttgtaag ttgagaacac ccaatttgta    1620
atggg                                                                1625

<210> SEQ ID NO 77
<211> LENGTH: 1740
<212> TYPE: DNA
<213> ORGANISM: Echinops bannaticus

<400> SEQUENCE: 77
cctccaaact ccatatgtaa aatgaccatt ctaaccttcc tcctgtacac ctgcattact      60
gggttagtct tctatgcatt gcacttgttt aacctgcgca cacctcaccg taaccgcctc     120 cccccggcc caacaccatg gccaatcgtc ggcaacttac cacatctcgg cagagttccg      180
caccattcgc tggcggactt ggcgacaaag tacgcccgt tgctgcatct ccggctcgga      240
tttgttgacg tggtggtggc cggatcggct tctgtcgccg cacagttttt gaaggttcat     300
gatgcgaatt tcgctagcag gccgccgaac tccggagcga agcatatggc gtataattat     360
caggatatgg tgttcgcacc gtacggtccg aaatgccgga tgcttcggaa gatttgctcg     420
gtgcaccttt tctctaccaa agcactcgat gatttccgtc acgttcgtca ggaggaggta     480
gcgatacttg ctcgcgcttt ggtcggagcc ggagaatcaa cggtgaaatt aggtcagtta     540
cttaacgtgt gcaccacara cgcgttagca cgagttatgt taggcaggag agtgtttggc     600
gatgcaagtg gaggcggcga ttcgaagtcg gatgaattta aggatatggt gatggagatg     660
atggtgttgg ccggagaatt caacatcggc gacttcattc cggctctgga ctggctggac     720
ctgcaatccg tgacgaaaaa gatgaagaaa ctccatgttc ggttcgattc gttccttaat     780
acgatcctgg aagagcataa aagtggtaat atggattttg tgagcaggtt gatttccgtc     840
aaggatgatg cagacggaca gggagggaag cttttcagaca ccgaaatcaa agctttactt     900
ctgaatttgt ttgccgcggg aacagacaca tcatctagca ctgttgaatg ggcaatcgcc     960
gaactcattc gacatccaca actattgaag caagcccaag aagaaatgga caccatagtt    1020
ggtcgagacc ggctagttac tgaagtcgac ctaagtagac taacattcct ccaagccatt    1080
gtgaaggaga tatttagcct ccatccgtca acaccactct cattgccaag gattgcatca    1140
gacacttgtg aggttgacgg atattatatt cctaaaggat ccacgctcct tgttaatgtg    1200
tgggccatct ctcgagaccc aaaaatatgg tccaatccac ttgaattcca acccactcga    1260
ttcttccctg gtggtgaaaa gccagatgcc gatgtcaagg gaaatgattt tgagctcata    1320
ccatttgggg ctggacgaag gatttgtgca ggtatgagtc tgggattaaa gatggtccag    1380
ttactcactg caactctagt ccatgcattc gattgggaat tggctaacgg gttagaccca    1440
gataagctca acatggaaga agcctatggg ttaaccctcc aaagggctac acccttgatg    1500
gtgcacccaa ggccaaggtt agcccctcat gtataccaaa gtggttaagg acttaacccg    1560
ttatttattc gcattttttgt ttgcgaaatt aattaatcat attttctcta gcgattatgt    1620
acgttctcta aaaatgtttt ttttaattat cttattcatg taagttgttt catgtttttgg    1680 ctaaataaat aatttaaata ctcatctatc attcttttca aaaaaaaaaa aaaaaaaaa    1740
```

<210> SEQ ID NO 78
<211> LENGTH: 1578
<212> TYPE: DNA
<213> ORGANISM: Centaurea cyanus

<400> SEQUENCE: 78

```
atgacatttc taccoctggt tctatacacc tctgtcgccc tgttactcct ctacgtattg      60
cttaacctac gcacccctcg ctcgaaccgc cggcttcccc ccggcccgac cccgtggccg     120
atagtcggaa acttgcctca tctcggcaag atgcctcacc atgcattggc cgcaatggcg     180
gacaagtacg gcccttgat gcatctacgg ttcggcgttg tggacgtcgt ggtggccgcg      240
tctgcttccg tggccgctca gttttgaag gtccacgacg cgaacttcgc gagcaggccg      300
cccaactccg gggcgaagca tctcgcgtac gattatcagg atctcgtgtt tgccccatac     360
ggtctgaagt ggaggatgct tcggaagatc tgctcggtgc atctgttctc gaataaggca     420
ctcgatgatt ccgtcacgt tcgtgaggag gaggtggcgg ttttgacccg tgctttggcc      480
ggagccggag atcgacggt ggcttaggt caattactta acgtttgcac cacaaacgct       540
ttggcacgag tgatgttagg taggagagta tttggtgacg gtagcggagg cggagatcgg     600
aaggcggatg aattcaagga aatggtggtt gaaatgatgg tattggccgg agaattcaac     660
atcggcgact tcattccggc gcttgattgg ctggacctgc aaggcgtaac caaaaaaatg     720
aaaaacctcc atctccgatt tgattcgttt cttaacgaaa tcctcgaaga ccataaaaat     780
ggcggtgaca tcatcactic cggtaacgtg gacttgctaa ccacgttgat ttcactcaag     840
gacgacgccg atgggaggg tgggaagctt tcagacatcg aaatcaaagc tatacttctg     900
aatttattta ctgctggaac agacaccctca tctagtacgg tggaatgggc aatggcagaa     960
cttattcgat atccacaact aatgcaaaaa gcccaagaag aaatagaaag cgtagtcggt    1020
agggaccgac ttgtatctga attggaccta ccccgactaa cgttccttga agccgttgtg    1080
aaggaaacct ttaggctcca cccgtcgacc ccactatcct tgcctagaat ggcattagag    1140
agttgtgaag tcgatgggta ttacattccc aaaggatcca cgcttcttgt taacgtgtgg    1200
gccattgctc gagacccaaa aatgtgggat gacccgcttg aattccgacc tagacgattc    1260
ttgccaagag gtgaaaaacc gaatgctaat gtgaaggaa atgatttcga aatcataccg     1320
tttgggctg gacgaagaat ttgtgcaggc atgagcctag ggttaaggat ggtccagttg     1380
ctcaccgcga cactggtcca tgcctttgat tggaaattgg ctaatgggtt agactcagag     1440
aaattgaaca tgaaagaagc ttatggggtta acccttcaaa gggatgtacc tttgatggta    1500
cacccctagcc caaggttagc tcccgagtta tacaaaagtg gttaaggtct tgaaaaacca    1560
atgtagtggt ctatagca                                                    1578
```

<210> SEQ ID NO 79
<211> LENGTH: 1539
<212> TYPE: DNA
<213> ORGANISM: Gerbera hybrida

<400> SEQUENCE: 79

```
atgacgcctt taacgctcct tatcggcacc tgtgtcactg gattattcct ctacgtgttg      60
cttaaccggt gcacccgtaa ccctaaccgc ctcccgcccg gcccaacgcc atggccggtc     120
gtcggaaacc taccgcatct cggcactata ccacaccact cgctggcggc gatggcgaag     180
aagtatggcc cgttgatgca cctccggcta ggcttcgtcg acgtcgtggt ggccgcctcc     240
gcctccgtcg ccgcgcagtt tttgaagact cacgacgcga acttcgccga tcggcctccg     300
```

```
aactccggag ccaagcatat cgcgtataat tatcaggatc tggtgtttgc tccgtacggt    360
ccgcggtggc ggatgcttcg gaagatttgc tcggtgcacc tgttttccac caaagcgctc    420
catgatttcc ggcacgtccg gcaggaggag gtagcgatac tagcgcgcgc tttggtcggc    480
gccggaaaat caccggtgaa attaggtcag ttactgaacg tgtgcaccac aaacgcattg    540
gcgcgagtga tgttagggag gagagtattt gactccggcg atgctcaggc ggatgagttc    600
aaggacatgg tggttgagct gatggtgtta gccgagaat  tcaacatcgg cgacttcatc    660
cccgtgcttg actggctgga cctgcaaggc gtgacgaaga agatgaagaa actccacgcg    720
aaattcgact cgttccttaa cacgatcctc gaagaacata aaaccggcgc cggtgacggt    780
gtcgcgtcgg gtaaagttga cttgttgagc acgttgattt cgctgaagga tgacgcagat    840
ggagagggag ggaagctgtc ggacattgaa atcaaagctt tgcttctgaa cttattcaca    900
gcggggactg acacatcatc tagtactatt gaatgggcta tagctgaact aattcgcaac    960
ccgcaactat tgaaccaagc ccgaaaagaa atggacacca tagttggtca agaccgactt   1020
gtaaccgagt cagacctagg tcaactaaca ttcctccaag ccattatcaa ggaaactttt   1080
aggcttcacc cgtcgacccc actatcactg ccaaggatgg cattggaaag ttgtgaggtt   1140
ggcggttatt acatccctaa aggatccact ctccttgtta atgtgtgggc catttctcga   1200
gaccctaaaa tttgggccga tccacttgaa tttcagccca ctcgattctt acctgggggt   1260
gaaaagccca atactgatat caaaggaaat gatttttgaag tcataccgtt tggggccgga   1320
cgaaggattt tgtgtcggaat gagcctaggg ttaaggatgg tccagttgtt gactgcaacc   1380
ctaatccatg cctttgattg ggaactggct gatgggttaa acccaaagaa gcttaacatg   1440
gaagaggctt acgggctgac ccttcaaagg gccgcaccgt tagtggttca cccaaggcca   1500
aggttagccc cacatgtata tgagacgact aaggtctag                          1539

<210> SEQ ID NO 80
<211> LENGTH: 1801
<212> TYPE: DNA
<213> ORGANISM: Osteospermum hybrida

<400> SEQUENCE: 80
gaaaaccacc tttacattct tatttattta tttattacac atacataagt aaaatgacca     60 ttttaccccct tgtactctac agttgcatca ctggattagt gatctatgta ctgcttaacc   120
tgcgcacccg tcactctaac cgcctgcccc ctgggcccac accatggccg atcgtcggaa   180
acctaccgca tctcggcgta gttccgcatc actcgctggc ggcaatggcg gaaaaatacg   240
gtccgttgat gcatctccgg ttaggttttg ttgacgtggt ggtggcggcg tctgctgccg   300
ttgctgctca gttttttgaaa gttcatgatg cgaattttgc gagtagaccg cctaattccg   360
gtgcgaaaca tatagcgtat aattatcaag acttggtgtt tgcgccgtac tacggtccgc   420
ggtggcgtat gcttcggaag atttgctccg ttcacctgtt tccttctaaa gcgcttgatg   480
atttccggca tgtccgccag gaggaggtgg cgatactgac gcgcgctttg atcggcgccg   540
gtgactcgcc ggtgaaacta ggtcaattac tgaacgtgtg cacaacaaac gcattggcgc   600
gcgtgatgtt aggtaagaga gtattcggtg acagaagtgg tggcggtgat ccaaaggcgg   660
atgagttcaa ggatatggtg gttgaggtga tggagttggc cggagaattc aatatccggtg   720 attttatacc ggtgcttgat tctctcgatc tgcaaggaat cgcgaagaag atgaaggaac   780
ttcacgtgcg atttgattcg ttccttggta agatccttga agaacataaa accggcaacg   840
gtggcgcgtc gagtcaacac actgacttgt tgactaccct tgatttcactc aaggatgata   900
```

```
ctgatgaaga gggtgggaag ctttcagaca ttgaaatcaa agctttgctt ctgaacttat      960
ttactgcggg aacagacacg tcatctagta ccgtggaatg ggcaatagcc gaactcattc     1020
gtcatccgca actattgaaa caggcccaag aagaaataga caatgtagta ggccgagacc     1080
acctagtaac cgaattggac ctaacccaac taccattgct ccaagccatt gtgaaggaga     1140
cctttaggct ccacccatca acaccactct cactaccaag aattgcatcc gagagttgtg     1200
aggtcaacgg gtaccatatc cctaagggat ccacactcct tgttaacgtg tgggccatag     1260
cccgagaccc raaaatgtgg tccgaaccac ttgaattccg tccagcccga ttcttacccg     1320
ggggtgaaaa gcccgatgct gatgttaagg gcaacgattt tgaagtcata ccattcgggg     1380
ccggaaggag gagttgtgcg ggtatgagtc taggattgag aatggttcaa ttactcgttg     1440
caacgttggt acaaaccttt gactgggaat tggctaatgg gttgaaaccc gagaagctta     1500
acatggaaga agcgtatggg ctaactcttc aacgggctgc acccttgttg gtacacccaa     1560
agccgaggtt agcacctcat gtgtacggaa gtaattaagg gctaaattct ctatggcgtt     1620
tttgtttgca taattattca attcaagttt ttgtttgcat aattattcaa ttcaaatttc     1680
gatttcgaat tcgaataatt aggtaaacaa ttgtatttgc tatttgaagt gttagtgtat     1740
atggtttctg taagtgattg agatattttc atgataatga aaaacaatg atgcgaaaaa     1800 a                                                                    1801

<210> SEQ ID NO 81
<211> LENGTH: 1663
<212> TYPE: DNA
<213> ORGANISM: Cichorium intybus

<400> SEQUENCE: 81
gaaaactccg tctacaaact acttacatca cactttttga accgaacccc catcatatgt       60
aaaatgaccc ttttaacact aatcatctac gcctgcgtca ctgggatagc agcctatgta      120
ttgctaaacc tgcggaaccg tcgggcaaaa cgcctgccgc ccggcccaac cccatggccc      180
atagtcggaa acttacctca cctcggtaca atcccgcacc actcgttggc cgctttagca      240
acaaggtacg gaccgttgat gcacctacgt ctcggcttcg ttgacgtggt ggtggcggca      300
tcggcatccg tcgctgcaca gttttttgaag gctcatgacg ctaatttcgc cagcaggccg      360
cccaattccg gagcgaagca tatggcgtat aattatcagg atctggtatt cgcgccgtac      420
ggtccgcggt ggcgaatgct tcggaaaatt tgctcggtgc atctgttttc tgccaaatca      480
cttgatgatt tccgtcacgt tcgacaggag gaggtagcga tactcacgcg cgctctggtt      540
gatgccggaa atcaacggt gatattgggt cagctactta acgtgtgcac cacaaacgca      600
ttggcacgag taatgttagg caggagagta tttggcgatg gaagcggagg aggcgatcca      660
aaggcagatg agttcaagga tatggtggtt gaactgatgg tgttagccgg agaattcaac      720
atcggtgact tcatcccggc gcttgatatt ctggacctgc aaggcgtgac gaaaaagatg      780
aagaaacttc acactcgatt cgattcgttc cttaacacga tcctcgaaga gcataaaacc      840
ggcggcagcg cgcgtcggc tcacgtagac ttgttgagca cgttgatttc gctgaaggat      900
gatgccgatg gagagggagg gaagctttcg acaccgaaa ttaaagctt acttctgaat      960 ttattcgctg cgggaaccga tacgtcatct agtaccgtgg aatgggcaat agcggaactc     1020
atccgccatc cgcatttaat gaaacaagcc caacaagaaa tggacacagt agtaggtcaa     1080
gaccggcttg taaccgaatt ggacctgagt caactaacat tcctccaagc cattgtgaag     1140 gaaacccttta ggctccaccc atcaacacca ctctccttac caagaatagc atccgagagc     1200
```

```
tgtgagatca acgggtacaa cattccaaaa ggatccacac tccttgtcaa cgtgtgggcc    1260
atagcccgcg acccgaaaat gtggaccaac ccgcttcagt tccagcccgc ccggttcatc    1320
cccgggggcg aaaagcccaa tgctgatgtc aagggaaatg attttgaagt gataccattt    1380
ggggcaggac gaaggatttg tgcgggtatg agcctagggt tgagaatggt ccaattgctc    1440
actgcaacac tcgttcaagc cttttgattgg gaattggcta atgggttgga accagccgac    1500
cttaacatgg aagaagccta tgggttgacc cttcaaaggg ctgcacccct ggttgtgcac    1560
ccaaggccga ggttagcccc ctatgtgtac aaaacttaag acccgataaa ccgaatgctc    1620
ttttgtgttt ttgtttgctt aatataattg gagtttgtgt ttc                     1663

<210> SEQ ID NO 82
<211> LENGTH: 1981
<212> TYPE: DNA
<213> ORGANISM: Antirrhinum majus

<400> SEQUENCE: 82
gccggcctaa taactaaaag cccactcttt ccgaccatct atacatgcaa caccaatatt     60
attctttaat tacgatggat gatattagca taaccagctt attggtgcca tgtactttta    120
tattagggtt cttgcttcta tattccttcc tcaacagaaa agtaaagcca ctgccacctg    180
gaccgaagcc atgcccatc gtcggaaatc tgccacatct tgggccgaag ccccaccagt    240
cgatggcggc gctggcacgg gtgcacggcc cattaattca tctgaagatg gctttgtgc    300 atgtggttgt ggcctcctca gcatccgttg cggagaaatt tctgaaggtg catgacgcaa    360
acttctcgag caggcctccc aattcgggtg caaaacacgt ggcctacaac tatcaggact    420
tggtctttgc tccttatggc ccacgctggc ggatgctcag gaaaatctgt gcactccacc    480
tcttctccgc caaagccttg aacgacttca cacacgtcag acaggatgag gtggggatcc    540
tcactcgcgt tctagcagat gcaggagaaa cgccgttgaa attagggcag atgatgaaca    600
catgcgccac caatgcaata gcgcgtgtta tgttgggtcg acgcgtggtt ggacacgcag    660
actcaaaggc ggaggagttt aaggcaatgg tagtggagtt gatggtatta gctggtgtgt    720
tcaacttagg tgattttatc ccacctcttg aaaaattgga tcttcaaggt gtcattgcta    780
agatgaagaa gcttcacttg cgtttcgact cgttcttgag taagatcctt gaagaccaca    840
agatcaacag ctcagatgaa accaaaggcc attcggattt gttgaacatg ttaatttctt    900
tgaaggacgc tgatgatgcc gaaggaggga ggctcaccga cgtagaaatt aaagcgttgc    960
tcttgaactt gtttgctgca ggaactgaca caacatcaag cactgtggaa tggtgcatag   1020
ctgagttagt acgacatcct gaaatccttg cccaagtcca aaaagaactc gactctgttg   1080
ttggtaagaa tcgggtggtg aaggaggctg atctggccgg attaccattc ctccaagcgg   1140
tcgtcaagga aaatttccga ctccatccct ccaccccgct ctccctaccg aggatcgcac   1200
atgagagttg tgaagtgaat ggtacttga ttccaaaggg ttcgacactt cttgtcaatg    1260
tttgggcaat tgctcgcgat ccaaatgtgt gggatgaacc actagagttc cggcctgaac   1320
gattcttgaa gggcggggaa aagcctaatg tcgatgttag agggaatgat ttcgaattga   1380
taccgttcgg agcgggccga agaatttgtg caggaatgag cttaggaata cgtatggtcc   1440
agttgttgac agcaactttg atccatgcgt ttgactttga tttggcggat ggacagttgc   1500
ctgaaagctt aaacatggag gaagcttatg gctgaccctt gcaacgagct gacccttttgg  1560 tagtgcaccc gaagcctagg ttggcacctc atgtttatca aacttaggac tcatgtttag   1620
agaacctctt gttgttttat cagattgaag tgtgatgtcc aagaccccct ttattagcat   1680
```

```
aagtacctac ccatggcgca tctgtaataa aatctgggtc aaatgccaaa actactcgtg    1740
tgttatctcc acttggcaat taaagtccta tgttatttca attagcaaaa aaaccccctgt   1800 gcacaatacc aaactttgct cccaattccc aactcatttt caactttgac tggatgcaaa   1860
atggcctttt tgcccatata taaagcttct aatcatttaa gaattttact tcaaagattt    1920
tgaaactaaa attcttttc attaaaaaaa aaaaaaaaa aaaaaaaaa aaaaaaaaa       1980 a                                                                   1981

<210> SEQ ID NO 83
<211> LENGTH: 1542
<212> TYPE: DNA
<213> ORGANISM: Arabidopsis thaliana

<400> SEQUENCE: 83
atggcaactc tatttctcac aatcctccta gccactgtcc tcttcctcat cctccgtatc     60
ttctctcacc gtcgcaaccg cagccacaac aaccgtcttc caccggggcc aaacccatgg    120
cccatcatcg gaaacctccc tcacatgggc actaagcctc atcgaaccct tccgccatg    180 gttactactt acggccctat cctccacctc cgactagggt tcgtagacgt cgtggtcgcc    240
gcttctaaat ccgtggccga gcagttcttg aaaatacacg acgccaattt cgctagccga    300
ccaccaaact caggagctaa acacatggca tataactatc aagatcttgt cttttgcacct    360 tacggacacc gatggagact gttgagaaag attagttctg ttcatctatt ttcagctaaa    420
gctctcgaag atttcaaaca tgttcgacag gaagaggttg gaacgctaac gcggagcta     480 gtgcgtgttg gcacgaaacc cgtgaattta ggccagttgg tgaacatgtg tgtagtcaac    540
gctctaggac gagagatgat cggacggcga ttgttcggcg ccgacgccga tcataaagct    600
gacgagtttc gatcaatggt gacggaaatg atggctctcg ccggagtatt caacatcgga    660
gacttcgtgc cgtcacttga ttggttagat ttacaaggcg tcgctggtaa aatgaaacgg    720
cttcacaaga gattcgacgc ttttctatcg tcgattttga aagagcacga aatgaacggt    780
caagatcaaa agcatacaga tatgcttagc actttaatct ccttaaagg aactgatctt    840 gacggtgacg gaggaagctt aacggatact gagattaaag gcttgctatt gaacatgttc    900
acagctggaa ctgacacgtc agcaagtacg gtggactggg ctatagctga acttatccgt    960
cacccggata taatggttaa agcccaagaa gaacttgata ttgttgtggg ccgtgacagg   1020
cctgttaatg aatcagacat cgctcagctt ccttaccttc aggcggttat caaagagaat   1080
ttcaggcttc atccaccaac accactctcg ttaccacaca tcgcgtcaga gagctgtgag   1140
atcaacggct accatatccc gaaaggatcg actctattga cgaacatatg gccatagcc    1200 cgtgacccgg atcaatggtc cgacccgtta gcatttaaac ccgagagatt cttacccggt   1260
ggtgaaaaat ccggcgttga tgtgaaagga agcgatttcg agctaatacc gttcggagct   1320
gggaggagaa tctgtgccgg tttaagttta ggttacgta cgattcagtt tcttacggcg    1380
acgttggttc aaggatttga ttgggaatta gctggaggag ttacgccgga aagctgaat    1440 atggaggaga gttatgggct tacactgcaa agagcggttc cttttggtggt acatcctaag   1500 ccaaggttgg ctccgaacgt ttatggactc gggtcgggtt aa                      1542

<210> SEQ ID NO 84
<211> LENGTH: 1704
<212> TYPE: DNA
<213> ORGANISM: Callistephus chinensis

<400> SEQUENCE: 84
```

```
                                              -continued
attacatccc cctcacatgt gcaatgacca ttttaccctt tattttctac acatgtatca      60
ctgccttagt gctctatgta ttgcttaacc ttttgacccg taacccaaac cgccttcccc     120
caggtccaac cccatggccc atagttggaa acctaccaca ccttggcatg ataccacacc     180
actcattagc ggccttggcc caaaagtatg gtccgctgat gcacctacgc ctcgggtttg     240
ttgacgtggt cgtggccgcg tcagcatccg ttgcggcaca atttctaaaa actcatgacg     300
caaactttgc aagtagacca cccaagtctg gagccaagca tattgcctat aactatcaag     360
atcttgtgtt cgcaccttat ggtccaaggt ggcgaatgct taggaaaatt tgttcggttc     420
acttgttttc cactaaagca ctagacgact tccgtcatgt tcgagaggaa gaggtagcga     480
tactgacgcg agtgttagtc catgcgggtg aatcagcggt gaaattagga carctactga     540
acgtgtgcac cacaaacgcg ttagcacgag tgatgctagg ccgagagtt ttcgcggacg      600 gcagtgaagg ccggggagtc gacccaaagg cagatgagtt caaggacatg gtggtggaac     660
tcatggaatt agccggtgaa ttcaacatag gtgacttcat accaccactt gactgccttg     720
atttgcaagg catcaccaaa aagatgaaga aacttcatgc tcgattcgac aagtttctta     780
acatcatcct agacgaccat aaaatcgaaa aaggcgcggc cggccgccgt catagtgact     840
tgctgaccac gctgatttca ctcaaggatg ttgatgctgc tgatgatgat gaagaaggga     900
aactttcaga cattgaaatc aaggctttgc tcctgaactt atttgctgca ggaacagaca     960
catcatctag taccgtggaa tgggcagtag ccgaacttat tcgtcatccg gaactattga    1020
aacaagcacg cgaagaaatg gatatcgtag ttggtcgaga ccggcttgta accgaattgg    1080
acttaagccg gctaacattc ctacaagcca ttgtgaagga gacctttagg ctccaccctt    1140
cgacgccact ctcccttcca aggatggcgt cggagagttg cgaggtggat gggtactaca    1200
ttcccaaagg atccacactc cttgttaatg tatgggccat agcccgcgac ccaaaaatgt    1260
ggactaaccc acttgagttc aggcccagtc ggttcttacc cgggggtgaa aagcccgatg    1320
cacatatcaa aggaaatgat tttgaggtca taccatttgg ggccgggaga agaatatgtg    1380
cgggtatgag cctagggatg agaatggtcc agttgctcat tgcaacattg gtccaaacct    1440
ttgattggga attggctaat gggttagacc cggagaagct caacatgaa gaagcttacg     1500 ggctaaccct tcaaagggct gaaccctta tggtgcaccc aaggcccagg ctatctcccc     1560
atgtatatga aagtcgttaa ggactaaaac ggattttggt gttttggtta gccaagttgg    1620
aaattcggca tttgtatttc aaatgattat ggaaagtaat gtctttgctc ttcgaattgt    1680
tggtaaaaaa aaaaaaaaa aaaa                                           1704
```

CHALCONE 3-HYDROXYLASE

BACKGROUND OF THE INVENTION

1. Field of the Invention

The present invention relates to nucleic acid molecules, comprising a nucleotide sequence encoding a polypeptide with chalcone 3-hydroxylase activity.

2. Description of Related Art

The flower color is one of the most striking characteristics of ornamental plants and is therefore a significant factor for their market value. Beside traditional growing, genetic approaches for the creation of new species increasingly gain significance. Examples for that are the generation of blue carnations as well as that of the so-called blue rose, which is already commercially available in a great many countries worldwide.

The development of the flower colors is mainly based on the presence of two different pigment groups, the carotenoids and the flavonoids. The flavonoid class of anthocyanins is mainly responsible for the formation of the red, blue and purple flower colors, while the yellow flower color in most of the cases results from the accumulation of carotenoids. In some plant species, however, the yellow plant color is formed by yellow flavonoids and their biosynthetically related anthochlor pigments (chalcones and aurones). Therefore, a modification of the chalcone or flavonoid metabolism, respectively, may decisively contribute to the alteration of the flower colors. Beside growing plants with blue flowers, the introduction of the yellow flower color in ornamental plants, of which no or only occasional yellow varieties are available, is of particular interest. Often only small modifications in the pigment structure result in drastic color changes. This above all applies to the number of the hydroxyl groups in the basic structures.

Although many flavonoids in their chemically pure form have a pale yellow color, their presence in petals does not result in the development of the yellow flower color. Beside the common 5,7-hydroxylation pattern of the A-ring, the so-called "yellow flavonols" have an additional hydroxyl group at positions 6 or 8, which effects an absorption shift into the longer-wave region and thus an intensification of the yellow color. The presence of such higher hydroxylated compounds results in the development of the yellow flower color. Quercetagetin was first identified as the yellow pigment in various species of marigold and is also present in the flowers of *Rudbeckia hirta*.

Yellow flavones represent the main pigments in some flowers of Asteraceae. While the common prevalent flavones do not result in the development of yellow flower colors, the presence of an additional hydroxyl group at position 2' of the B-ring of luteolin effects a yellow coloration of the pigment. Isoetin (2'-hydroxyluteolin) was identified as the yellow main pigment of *Heywoodiella oligocephala*. The introduction of a hydroxylase, which catalyses the 2'-hydroxylation, could result in the formation of yellow-colored flavones in the flowers of transgenic plants, which generally only produce common flavones.

Contrary to the yellow flavonols, for which the presence of an additional hydroxyl group results in the development of the yellow flower color, the loss of a hydroxyl group at position 3 of anthocyanins or anthocyanidins, respectively, is responsible for a shift of the absorption into the shorter-wave region and thus for the orange and yellow color of the so-called 3-deoxyanthocyanins. 3-deoxyanthocyanins are rare plant pigments, which as such exist in only a few plants like Gesneriaceae, *Zea mays* (maize) and in species of *Sorghum* (millet). Three representatives of this group could be identified, apigeninidin (3-deoxypelargonidin), luteolinidin (3-deoxycyanidin) and columnidin. Of these, however, only apigeninidin derivatives contribute to the yellow flower color. The others have an orange to light red coloration. The biochemical formation of the flavan-4-ols as precursors for the 3-deoxyanthocyanins is caused by the reduction of the carbonyl group of the flavanones at position 4. This reaction is catalysed by dihydroflavonol-4-reductase in a high number of cultivated and ornamental plants, however, commonly only takes place in plants, in which the FHT reaction is inhibited.

The deep yellow anthochlor pigments (chalcones and aurones) have only a limited spread in nature, however, frequently exist in species of Asteraceae or Scrophulariaceae. In general, two types of chalcones can be synthesised in the flowers, the 6'-hydroxychalcones (phloroglucinol type) and the 6'-deoxychalcones (resorcinol type). The respective aurones are the 4-hydroxy- and the 4-deoxyaurones (identical position, different numbering of the rings). 6'-deoxychalcones are formed by chalcone synthase together with chalcone ketide reductase (CHKR, synonyms polyketide reductase, PKR, chalcone reductase) via a polyketide intermediate.

Chalcones are secondary plant metabolites and biochemical precursors for all flavonoid classes. Therefore, and due to their physiological functions in plants, like e.g. the influence on the flower color, they play an important role in the plant physiology. Beside the common 6'-hydroxychalcones, which represent intermediates of the biosynthesis of the widespread 5-hydroxyflavonoids, the more rare 6'-deoxychalcones are often accumulated in the flowers of Asteraceae species, since chemically they cannot be converted into the respective 5-deoxyflavanones and are also not accepted as substrates by the chalcone isomerases (CHIs) of most plants. The accumulation of 6'-deoxychalcones results in the development of the yellow flower color. 6'-hydroxychalcones, on the other hand, are accumulated in the plant tissue in rare cases only, since they can be easily converted into flavanones enzymatically or chemically. Therefore, in a few cases only, they are responsible for the yellow coloration of flowers, as in the yellow flowers of carnations (*Dianthus caryophyllus*), snapdragon (*Antirrhinum majus*) and everlasting flowers (*Helichrysum bracteatum*), since beside the CHI, these mutants are lacking at least one more enzymatic activity of the flavonoid metabolism.

Like flavonoids, chalcones, too, can have further hydroxyl groups beside the hydroxyl group at position 4 (corresponding to position 4' in flavonoids) in the B-ring, namely at positions 3 or 3 and 5 (corresponding to positions 3' or 3' and 5' in flavonoids). Contrary to the very well investigated hydroxylation of flavonoids at positions 3' and 3', 5', which are catalysed by the cytochrome P450-dependent monooxygenases flavonoid-3'-hydroxylase (F3'H) or flavonoid-3',5'-hydroxylase (F3', 5'H), respectively, for a long time there has been uncertainty about which enzyme is responsible for the introduction of additional hydroxyl groups in the B-ring of chalcones. It could be demonstrated that the introduction of a hydroxyl group at position 3 of 6'-deoxychalcones is catalysed by a cytochrome-P450-dependent monooxygenase. Investigations with recombinant F3'Hs of various plants, which accumulate chalcones in their petals, as well as of such ones, which do not accumulate chalcones, demonstrated, however, that these F3'Hs are not able to catalyse the hydroxylation of chalcones.

As mentioned already, the F3'Hs are membrane-bound cytochrome (cyt) P450-dependent monooxygenases. The super family of cyt P450 enzymes is a group of very different enzymes, which catalyses many different and complex oxygenation reactions with a high number of substrates in the presence of NADPH or NADH. They include a haem group and exist in prokaryotes as well as in eukaryotes. In plants, an extraordinarily high number of cyt P450 genes can be found. In *Arabidopsis* for example, 272 cyt P450 genes could be detected. The sequence identities of the cyt P450 enzymes are often very low.

SUMMARY OF THE INVENTION

Object of the present invention is the provision of nucleic acids encoding polypeptides, which are able to hydroxylate chalcones in the B-ring in order to, for example, influence the coloring in plants.

The present invention relates to an isolated nucleic acid molecule, comprising a nucleotide sequence, which encodes a polypeptide with chalcone 3-hydroxylase activity, wherein the nucleotide sequence comprises SEQ ID NO. 1 or has at least a 60% identity with SEQ ID NO. 1 or is able to hybridize with a molecule comprising the sequence of SEQ ID NO. 1, wherein the nucleotide sequence encodes a polypeptide, which comprises the motif $FASRPLSX_1X_2G(X_3)_m$ $(GSAGGD)_n$ (SEQ ID NO. 3), wherein $X_1$ is threonine or serine, $X_2$ is alanine or glycine, $X_3$ is any amino acid, m is an integer between 50 and 200, and n is 0 or 1.

According to the invention it was found out that polypeptides, in particular hydroxylases, as for example flavonoid 3'-hydroxylases, which have a certain motif (as defined above), are able to hydroxylate chalcones at position 3. The knowledge of such hydroxylases enables the modulation of the expression of these hydroxylases in order to, for example, overexpress or inhibit these in vivo. In particular, the knowledge of these enzymes enables the modulation of the quantity of hydroxylated chalcones in a plant or plant cell, respectively, in order to thus change the color composition in the latter. Thus, plants, which comprise the nucleic acid molecules according to the invention, have, for example, flowers with an intensive yellow coloration.

The nucleic acid molecule according to the invention catalyses the hydroxylation of various chalcones (this, for example, also includes 6'-deoxychalcones and dihydrochalcones) at position 3. In case of the 6'-hydroxychalcones and 4-deoxyaurones, this results in an intensification of the yellow coloration due to the enrichment of chalcones with a 3,4-hydroxy pattern, and also in an increased formation of aurones, since such chalcones also represent the preferred precursors for aurone-forming enzymes. In case of the dihydrochalcones, the formation of 3-hydroxychalcone derivatives is promoted, which are involved in the pathogen defence or due to their antioxidant properties have beneficial effects for health, respectively.

The nucleic acid molecule according to the invention can have SEQ ID NO. 1 as the nucleotide sequence or an at least 60%, preferably at least 65%, preferably at least 70%, preferably at least 75%, preferably at least 80%, preferably at least 85%, preferably at least 90%, preferably at least 95%, preferably at least 97%, preferably at least 98%, preferably at least 99%, in particular 100% identity with SEQ ID NO. 1.

Identity between at least two sequences can be achieved by overlapping, in which one nucleic acid or amino acid sequence is placed on top of at least one further respective sequence ("alignment"), for example according to the method of D. J. Lipman and W. R. Pearson (Science 227 (1985), 1435-1441) or F. Corpet (Nucl. Acids Res. 16 (1988), 10881-10890). Preferably, this takes place via algorithms, which are applied by commercially available computer programmes. This includes, for example, the programme Vector NTi""Suite 7.0, available from the company InforMax, Inc., USA, preferably with the default standard parameters. A further software, using which sequence identity can be determined, is, e.g., "Sequence Analysis Software Package of the Genetics Computer Group, University of Wisconsin Biotechnology Center, 1710 University Avenue, Madison, Wis. 53705". This software overlaps similar sequences by allocation of degrees of homology.

The nucleic acid molecule according to the invention is able to hybridize with a molecule comprising the sequence of SEQ ID NO. 1.

Hybridization designates the binding of complementary strands of nucleic acids (i.e. sense:antisense strands) with one another by hydrogen bonds, similar to the bonds, which occur naturally in chromosomal DNA. In that, stringency levels are used, in order to hybridize a nucleic acid with a target nucleic acid. These conditions may be easily varied by a person skilled in the art. According to the invention, the nucleic acid molecule hybridizes under more or less stringent conditions.

The term "stringent hybridization" is used here to designate conditions, under which nucleic acid hybrids are stable. As is known to the person skilled in the art, the stability of hybrids is reflected in the melting temperature (Tm) of the hybrids. In general, the stability of a hybrid is a function of the sodium concentration and the temperature. Typically, the hybridization reaction is performed under conditions of lower stringency, followed by washings of varying, but higher stringency. Reference to hybridization stringency relates to such washing conditions.

As used herein, the term "moderately stringent hybridization" designates conditions, which allow a target nucleic acid to bind a complementary nucleic acid, which has about 60% identity, preferably about 75% identity, more preferred about 85% identity with the target DNA; wherein more than about 90% identity with the target DNA are particularly preferred. Preferably, moderately stringent conditions are conditions equivalent to hybridization in 50% formamide, 5×Denhardt's solution, 5×SSPE, 0.2% SDS at 42° C. and subsequent washing in 0.2×SSPE, 0.2% SDS at 65%.

The term "hybridization with high stringency" designates conditions, which allow hybridization of only those nucleic acid sequences, which form stable hybrids in 0.018 M NaCl at 65° C. (i.e., if a hybrid is not stable in 0.018 M NaCl at 65° C., it will not be stable under high stringency conditions, as they are considered here). High stringency conditions may, for example, be provided by hybridization in 50% formamide, 5×Denhardt's solution, 5×SSPE, 0.2% SDS at 42° C. and subsequent washing in 0.1×SSPE and 0.1% SDS at 65° C.

The term "hybridization with low stringency" designates conditions equivalent to hybridization in 10% formamide, 5×Denhardt's solution, 6×SSPE, 0.2% SDS at 42° C. and subsequent washing in 0.1×SSPE, 0.2% SDS at 50° C. Denhardt's solution and SSPE (see e.g. Sambrook et al., Molecular Cloning, A Laboratory Manual, Cold Spring Harbor Laboratory Press, 1989) are known to the person skilled in the art, as are other suitable hybridization buffers.

According to the invention, SEQ ID NO. 1 has the following nucleotide sequence:

ATGACTATTCTACCCCTACTACTCTACCCTTCCCTAACTGCCTTACTA

CTGTACGTACTTCTTAACCTGCGCCCCCGTCACCCTAACCGTCTCCCG

CCGGGACCAAGCCCATGGCCGATCGTCGGAAACCTACCGCACCTCGGC

GCGAGTCCGCATCAGTCGCTGGCGACGTTGGCCGCAAAGTACGGCCCG

-continued

```
TTGATGTACCTCCGACTCGGGTTTGTTGACGTGGTGGTGGCGGCGTCT

GCTTCAGTCGCTGCACAGTTTTTAAAAGTTCATGATCTTAACTTCGCA

AGCCGGCCGCTGAGCTCTGGCGGGAAGTATATCGCGTATAATTATCAG

GATATGGTGTTTGCACCGTACGGTCCGAGATGGCGGATGCTTAGGAAG

ATTTGCTCCGTGCATATGTTTTCTGCTAAAGCAATGGACGGATTTCGT

CATGTTCGGCAGGAGGAAGTAGCTATACTCACGCGCACTTTAGTAAGC

GCTGGAAAATCGCCGGTGAAGTTAGGTCAAATACTTAACGTGTGCACC

ACGAACGCATTAGCACGAGTGGTGTTAGGTCGGAGAGTATTCGCCGAC

GGAAGTGCAGGTGGTGATCCGAAGGCGGATGAGTTCAAGGATATGGTG

GTGGAGCTGATGGTGTTGGCCGGAGAATTTCACATCGGTGACTTTATC

CCGGCGCTTGACTGGCTGGACCTGCAAGGCATTAAAAACAAGATGAAG

AAACTTCACGCTCGATTCGATTCGTTCCTTCACGGGATCCTTGAAGAG

CATAAGTCCGGCAAGTTTGGCGCGCCGAGTCATGGTGATTTGTTGAGC

ACATTGATCTCGTTGAAGGATGATGCCGATGGTGAAGGCGGGAAGCTT

TCAGATGTTGAAATCAAAGCTTTGCTTCTGAACTTATTTGTCGCCGGA

ACAGACACATCATCAAGTACAGTGGAATGGGCAATAGCCGAGCTAATT

CGACATCCAAAGCTACTAAAACAAGCCCAAAAAGAAATGGACAATGTA

GTTGGTCGAGACCGGCTTGTAACTGAATTAGACTTAAACGAGTTAAAT

TTTCTACAAGCCATTGTAAAAGAGACCTTTAGGCTTCACCCTTCAACA

CCACTCTCGTTACCAAGAATTGCATCAGAGAGTTGTGAAGTTGACGGA

TATTACATTCCCAAGGGATCCACGCTCCTTGTTAATGTGTGGGCCATT

GCTCGTGACCCGAATGTGTGGGCTGACCCACTTGAATTCCGGCCCATG

CGGTTCTTGCCTGGAGGCGAAAAGCCTAATGTTGATGTTCAAGGAAAC

AACTTTGAAGTTATACCGTTTGGGGCTGGGCGAAGGATTTGTGTGGGT

ATTAGTCTAGGGTTGAGAATGGTCCAGCTACTTGTTGCAACATTGGTT

CAAACCTTTGATTGGGAATTGGCTAATGGGTTAAACCCGGAGAAGCTA

AACATGGATGAAGCCTTTGGGTTAACCCTTCAGAAGGCTGAGCCCTTG

ATGGTGCACCCAATGCCGAGACTAGCTCCACACGTGTATGGAAGTCAT

TAA
```

According to the invention, the polypeptide encoded by SEQ ID NO. 1 has the following amino acid sequence (SEQ ID NO. 2):

```
MTILPLLLYPSLTALLLYVLLNLRPRHPNRLPPGPSPWPIVGNLPHLG

ASPHQSLATLAAKYGPLMYLRLGFVDVVVAASASVAAQFLKVHDLNFA

SRPLSSGGKYIAYNYQDMVFAPYGPRWRMLRKICSVHMFSAKAMDGFR

HVRQEEVAILTRTLVSAGKSPVKLGQILNVCTTNALARVVLGRRVFAD

GSAGGDPKADEFKDMVVELMVLAGEFHIGDFIPALDWLDLQGIKNKMK

KLHARFDSFLHGILEEHKSGKFGAPSHGDLLSTLISLKDDADGEGGKL

SDVEIKALLLNLFVAGTDTSSSTVEWAIAELIRHPKLLKQAQKEMDNV

VGRDRLVTELDLNELNFLQAIVKETFRLHPSTPLSLPRIASESCEVDG

YYIPKGSTLLVNVWAIARDPNVWADPLEFRPMRFLPGGEKPNVDVQGN

NFEVIPFGAGRRICVGISLGLRMVQLLVATLVQTFDWELANGLNPEKL

NMDEAFGLTLQKAEPLMVHPMPRLAPHVYGSH
```

According to a preferred embodiment of the present invention, the motif is FASRPLSTAG$(X_3)_m$(GSAGGD)$_n$ (SEQ ID NO. 4) or FASRPLSSGG$(X_3)_m$(GSAGGD)$_n$ (SEQ ID NO. 5).

Polypeptides having this motif are particularly well suited to be used according to the invention.

A further aspect of the present invention relates to a vector comprising a nucleic acid molecule according to the present invention.

The nucleic acid molecules of the present invention may be introduced into a vector. Using this vector, the nucleic acid molecules may be introduced into cells of plants or microorganisms. The vectors used may be used for cloning or for expressing respective products. Therefore, the vectors are provided with respective elements like promoters, origins of replication, etc. The vectors used according to the invention may contain a plant cell-effective promoter, as for example the CaMV 35S promoter, the nopaline synthase promoter or the sucrose synthase promoter.

If the vectors are used to introduce the nucleic acid molecule according to the invention into the genome of a target cell, respective elements may be provided at the vector, which enable a recombination of the nucleic acid into the genome.

Vectors, which may be used according to the invention, are sufficiently known to the person skilled in the art and may be introduced into a cell in most different ways. Thus, the vector according to the present invention may be introduced into the target cell by electroporation, microprojectile bombardment, transfer using *Agrobacterium* or by RNA or DNA viruses, respectively.

A still further aspect of the present invention relates to a cell, in particular a plant cell, comprising a nucleic acid molecule or a vector according to the present invention. Self-evidently, it is also possible to make the nucleic acid molecule or the vector, respectively, according to the present invention available in other cells, as for example yeasts, *E. coli*, filamentous fungi and the like.

A still further aspect of the present invention relates to the use of the nucleic acid molecules or proteins according to the invention in the generation of chalcone derivatives with a 3,4-hydroxylation pattern, as e.g. 3-hydroxyphloretin derivatives, butein and eriodictyol chalcone.

The nucleic acid molecules of the present invention may be introduced into plant cells and thus into plants in order to produce transgenic plants, which are able to express the polypeptide according to the invention. Therefore, a further aspect of the present invention also relates to a transgenic plant comprising a nucleic acid molecule or a vector according to the present invention. The nucleic acid molecule according to the invention or the vector according to the invention, respectively, may be introduced into plant cells and plants using methods sufficiently known to the person skilled in the art.

Preferably, the plant is selected from the group consisting of ornamental plants, like for example African violets, azaleas, rhododendrons, pelargoniums, fuchsias, cyclamens, poinsettias, *Antirrhinum, Aster* (Asteraceae), *Begonia* (Begoniaceae), *Callistephus* (Asteraceae), *Campanula* (Campanulaceae), *Catharanthus* (Apocynaceae), *Chrysanthemum* (Asteraceae), *Cineraria* (Asteraceae), *Dedanthremum* (Asteraceae), *Dianthus* (Caryophyllaceae), *Dahlia* (Asteraceae), *Euphorbia* (Euphorbiaceae), *Gerbera* (Asteraceae), *Hydrangea* (Hydrangeaceae), *Lilium* (Liliaceae), *Lisianthus* (=*Eustoma* (Gentianaceae)), *Myosotis* (Boraginaceae), *Nierembergia* (Solanaceae), Orchidaceae, *Osteospermum* (Asteraceae), *Petunia* (Solanaceae), *Rosa* (Rosaceae), *Saintpaulia* (Gesneriaceae), *Scaevola* (Goodeniaceae), *Sinningia* (Gesneriaceae), *Streptocarpus* (Gesneriaceae), *Torenia* (Linderniaceae), *Tulipa* (Liliaceae), *Verbena* (Verbenaceae), *Veronica* (Plantaginaceae), *Viola* (Violaceae) and *Malus* sp. Due to the presence of the nucleic acid molecule according to the invention, genetic engineering approaches based on polyketide reductase or aurone synthase are also substantially enhanced. If a purely yellow coloring is to be achieved, preferably white or cream-colored plants are used, wherein chalcone isomerase mutants or plants having a polyketide reductase are preferred. When using pink- or red-blooming plants, orange-colored or salmon-colored flowers are formed.

Additionally, it was demonstrated that plants expressing, in particular overexpressing, the polypeptide according to the invention—encoded by the nucleic acid molecule according to the invention—have an increased resistance against pathogens, in particular against fungi, viruses, viroids, bacteria and nematodes. In particular, such plants show resistances against *Puccinia/Ustilago*, *Phytophora*, *Blumeria*/Peronosporacea, barley yellow dwarf virus, sugarcane mosaic virus, plum pox, *Xanthomonas campestric* pv. *Citri*, *Erwinia amylovora*, *Erwinia carotovora*, *Meloidogyne incognita* and *Heterodera schachtii*.

A further aspect of the present invention relates to a cut flower or seed of a transgenic plant according to the present invention.

BRIEF DESCRIPTION OF THE DRAWINGS

The present invention is further illustrated in more detail on the basis of the following figures and examples, without, however, being limited to these.

FIG. 1 shows a paired alignment of the *Cosmos* CH3H and F3'H amino acid sequences (SEQ ID NO. 2 and SEQ ID NO. 36).

FIG. 2 depicts alignments of regions of various F3'Hs amino acid sequences.

FIG. 5 shows the primers used for the construction of the chimeric genes.

DETAILED DESCRIPTION

Examples

Example 1

Materials and Methods

Plant Material

Figure 3:
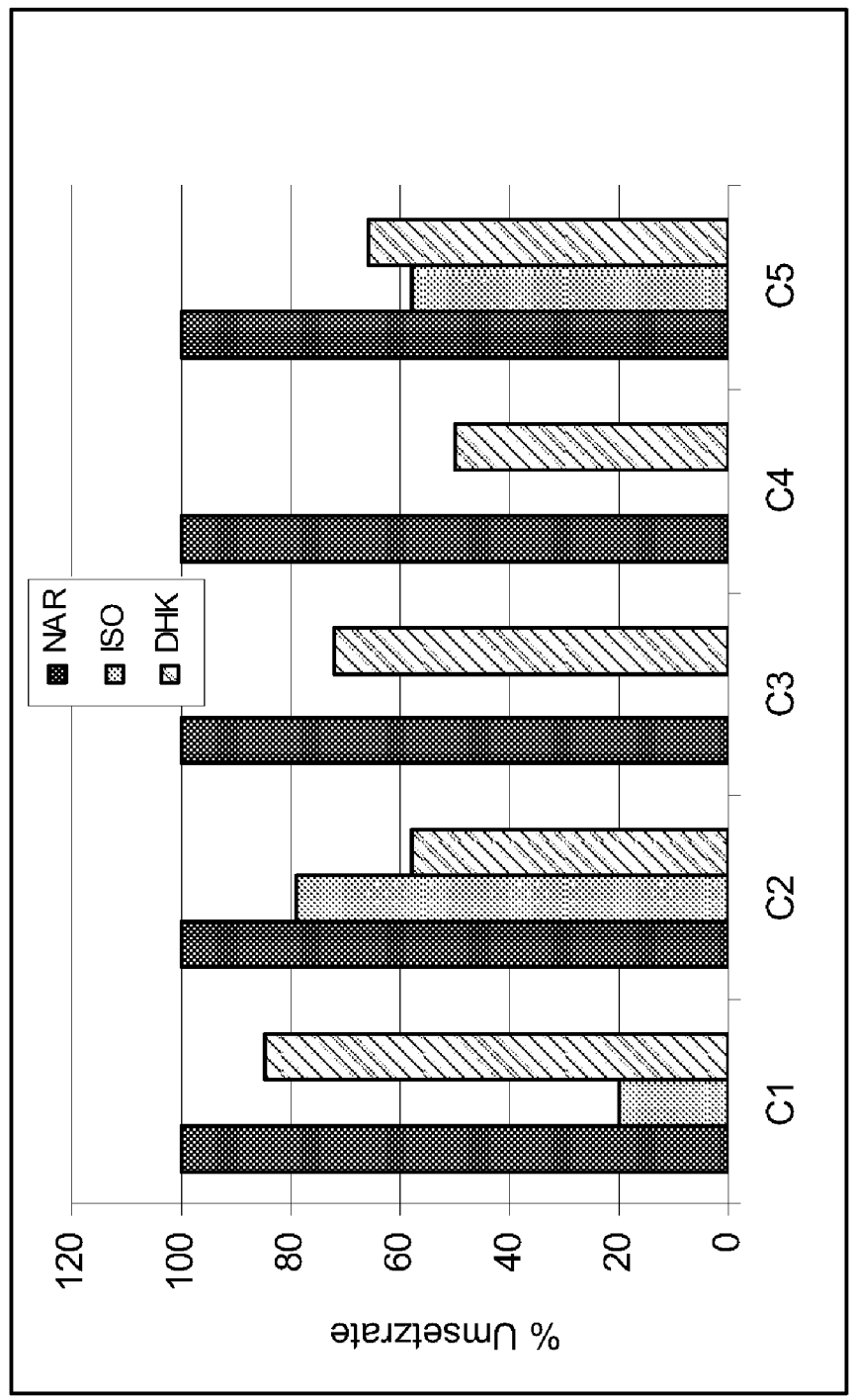
FIG. 3 shows the substrate specificities of *Cosmos* F3'H and M2 in percent relative to naringenin (100%).

The examinations were performed with petals of *Cosmos sulphureus* cv. "Sunny Goldgelb" (Austrosaat, Austria). The plant material was collected in summer 2006 and summer 2007, shock-frozen in liquid nitrogen and stored at −80° C.

Chemicals

[14C]isoliquiritigenin (ISO) was synthesised starting from 4-hydroxy[ring-U-14C]benzaldehyde (33.1 Mbq/mg) (Amersham International, UK) as described in Halbwirth et al. (2006) [Plant Science 170 (2006) 587-595]. The syntheses of [14C]naringenin (NAR), [14C]dihydrokaempferol (DHK), [14C]kaempferol (KAM) and [14C]apigenin (API) were performed according to Halbwirth and Stich (2008) [Phytochemistry 67 (2006) 1080-1987]: for the naringenin synthesis, [2-14C]malonyl-coenzyme A (55 mCi/mmol) (Amersham International, UK) and recombinant chalcone synthase were used, and the subsequent syntheses of DHK, KAM and API were respectively performed with recombinant flavanone 3-hydroxylase from *Malus domestica*, recombinant flavonol synthase from *Rudbeckia hirta* and microsomal enzyme preparations with high flavone syntase II activity from *Dahlia variabilis*.

Cloning of *Cosmos sulphureus* CH3H

For the cDNA synthesis, mRNA from the *Cosmos sulphureus* petals was extracted with the µMACS mRNA isolation kit (Miltenyi Biotec), and reverse transcription was performed with the RevertAid H Minus MuLV reverse transcriptase kit (Fermentas Life Science) and the Oligo(-dT) anchor primer GACCACGCGTATCGATGTCGAC(T)16V (SEQ ID NO. 6). A RT PCR was then performed with the degenerated primers TGGMGDATGCTKMG-GAARATYTG (forward primer) (SEQ ID NO. 7) and GCCCATTCMAYNGTRCTAGATGA (reverse primer) (SEQ ID NO. 8), which were derived from the conserved regions of the following Asteraceae F3'H sequences from NCBI GenBank: *Rudbeckia hirta* (Acc. No.: FJ216431), *Echinops bannaticus* (Acc. No.: FJ753549), *Centaurea cyanus* (Acc. No.: FJ753550), *Gerbera hybrida* (Acc. No.: ABA64468), *Osteospermum hybrida* (Acc. No.: ABB29899), *Cichorium intibus* (Acc. No.: FJ753548) and *Callistephus chinensis* (Acc. No.: AF313488). The entire open reading frame (ORF) was then amplified with the specific primers ATGACTATTCTACCCCTACTACTC (forward primer) (SEQ ID NO. 9) and CCTTAATGACTTCCATACACGTG (reverse primer) (SEQ ID NO. 10), which were derived from the fragments obtained in the 5'- and 3'-RACE.

Sequence Analyses and Construction of Chimeric Genes

Paired and multiple sequence alignments were performed with the software tool ClustalW, in order to identify regions, which could influence the determination of substrate specificity. The following F3'H sequences, mainly from Asteraceae species, were used for multiple sequence alignments: *Cosmos sulphureus* (Acc. No.: FJ216426), *Dahlia variabilis* (Acc. No.: FJ216428), *Tagetes erecta* (Acc. No.: FJ216430), *Rudbeckia hirta* (Acc. No.: FJ216431), *Echinops bannaticus* (Acc. No.: FJ753549), *Centaurea cyanus* (Acc. No.: FJ753550), *Gerbera hybrida* (Acc. No.: ABA64468), *Osteospermum hybrida* (Acc. No.: ABB29899), *Cichorium intibus* (Acc. No.: FJ753548), *Antirrhinum majus* (Acc. No.: DQ272592) and *Arabidopsis thaliana* (Acc. No.: AF271651) (Schlangen et al. 2009). A paired sequence alignment was performed with the listed F3'H from *Cosmos sulphureus* (Acc. No.: FJ216426). Chimeric genes, consisting of cDNA fragments of the mentioned F3'H from *Cosmos sulphureus* as well as the cDNA fragments of the newly isolated sequence, were produced according to Seitz et al. (2007) [FEBS letters 581 (2007) 3429-3434]. For that, the fragments, which were to be fused, were amplified with a Pfu DNA polymerase (Promega, Germany) in separate PCR reactions and ligated for 10 minutes in an overall volume of 20 it with respectively approx. 50 ng cDNA of each fragment and a T4 DNA ligase (Promega, Germany). The diluted ligation was used as a template for the subsequent proofreading PCR, in which the entire chimeric gene was amplified with the Taq/Pwo polymerase system (Invitrogen, UK).

Insertions or Deletions of Amino Acid Residues

Insertions of amino acid residues were introduced with primers having an excess of bases encoding the respective amino acid residues to be inserted. Deletions were introduced using amplification of two fragments of the respective F3'H cDNA lacking the bases encoding the amino acid residues to be deleted. The subsequent fusion of the two amplified fragments was performed as described for the construction of the chimeric genes.

Targeted Mutagenesis

Targeted mutageneses were performed using megaprimer PCR. This PCR was performed in two steps: in the first PCR, a megaprimer was amplified with Pfu DNA polymerase (Promega). For that, the plasmid with the inserted cDNA, which was to be mutated, was used as a template. As primers, on the one hand, an internal primer, which binds at the site, into which the desired mutation is to be inserted, and which has the modified base sequence required for that, as well as an expression primer were used. This amplified mutated fragment, on the other hand, was then used in a second PCR as a primer together with the corresponding expression primer, in order to amplify the entire ORF with the desired mutations with the Expand High Fidelity PCR System (Roche).

Heterologous Expression in Yeast For the heterologous expression, the proofreading amplicons were ligated into the yeast expression vector pYES2.1/V5-His-TOPO® (Invitrogen, UK) and transformed into *E. coli* TOP10F' (Invitrogen, UK). The identification of the sense constructs took place with a PCR, for which a gene-specific forward and a plasmid-specific reverse primer was used. Sense constructs were isolated and the correct sequence confirmed by sequencing. Desired plasmids were then transformed into the yeast strain INVSc 1 (Invitrogen, UK). The heterologous expression was performed according to methods known in science, and the prepared proteins were shock-frozen in liquid nitrogen and stored at −80° C. The determination of the amount of protein in the preparations was performed according to a modified Lowry method.

Enzyme Assays and Identification of the Products

In order to determine the substrate specificity of the heterologously expressed F3'Hs, the following enzyme tests were performed: 20 μg of the recombinant wild-type CH3H or 50 μg of the hybrid proteins, respectively, were incubated with 0.25 nmol [14C]-marked chalcone or flavonoid substrates in the presence of 10 mM NADPH and 0.1 M $KH_2PO_4$—$K_2HPO_4$ (with 0.4% Na-ascorbate, pH: 7.5) buffer at 30° C. After 30 min., the enzymatic reactions were stopped with 10 μl of glacial acetic acid and the phenolic compounds extracted twice with EtOAc. The organic phases were applied onto cellulose plates and chromatographed in CAW (chloroform: glacial acetic acid:water, 10:9:1). Detection and quantification of radioactivity took place using TLC analysis.

Kinetic Data

Kinetic data (apparent Michaelis constant (Km) and maximum speed of reaction (Vmax)) were determined using Lineweaver Burk plots.

Results

Cloning and Sequence Analysis of *Cosmos sulphureus* CH3H cDNA

In this example, the complete coding sequence of a cDNA from *Cosmos sulphureus* could be isolated using degenerated primers from various Asteraceae species (NCBI GenBank Acc. Nos.: FJ216431, FJ753549, FJ753550, ABA64468, ABB29899, FJ753548 and AF313488) and subsequent RACE techniques. The derived amino acid sequence of this clone has all the conserved motifs of membrane-bound cyt P450 proteins (like the N-terminal hydrophobic membrane anchor, the highly conserved haem domain, etc.). The sequence of this cDNA clone was entered into the EMBL/GenBank database under the following accession number: FJ216429. Alignments with F3'H sequences, mainly from Asteraceae species, which are not or only to a low extent able to hydroxylate chalcones, show that the derived amino acid sequence of the isolated cDNA from *Cosmos sulphureus* has high sequence identities with the aligned F3'Hs. The paired alignment with the already characterised F3'H from *Cosmos sulphureus* (Acc. No.: FJ216426) shows that these two sequences are not identical and have a sequence identity of 84% (FIG. 1).

Enzyme Activities of Putative *Cosmos sulphureus* CH3H

In enzymatic studies with the recombinant enzyme, which was obtained in the heterologous expression of the cDNA clone from *Cosmos sulphureus*, high catalytic CH3H activities with the 6'-deoxychalcone isoliquiritigenin could be demonstrated. Kinetic studies showed that the highest Vmax/Km (18.01/s*kg) can be observed with Iso as the substrate (Table 1).

Therefore, this protein from *Cosmos sulphureus* was called CH3H. As a comparison, the recombinant F3'H from *Cosmos sulphureus* (Accession No.: FJ216426) was tested with the same substrates. These tests confirmed the F3'H activity and the lacking CH3H activity of this enzyme. The turnover rates of the two recombinant proteins are listed in FIG. 4.

Identification of Regions, which could Play a Role in the CH3H Reaction

In order to identify regions, which could play a role in the CH3H activity in *C. sulphureus* CH3H, alignment studies were performed. For that, the already mentioned F3'H amino acid sequences were used, the recombinant enzymes of which are not able to hydroxylate chalcones (Schlangen et al. 2009, Plant Science 177 (2009) 97-102). In the analysis of the alignment it could be determined, that one region, which was described as a putative substrate detection region (SRS1) in cyt P450 enzymes by Gotoh (1992), in the CH3H sequence of *C. sulphureus* has striking differences compared to the respective SRS1 regions of the other F3'H amino acid sequences. Furthermore, a region D(192)GSAGGDP(199) can be detected in the *Cosmos sulphureus* CH3H sequence, which only exists in this amino acid sequence (FIG. 2). In the paired alignment with the *C. sulphureus* F3'H it shows, that the CH3H has an insertion of four amino acid residues compared to the F3'H (SAGG region, FIG. 1), and the adjacent residues of the inserted four amino acid residues are also different in CH3H (SAGG+N region, FIG. 1).

Construction of Chimeric Genes

Figure 4:
FIG. 4 shows a schematic representation of the construction of chimeric and mutated genes of CH3H or F3'H, respectively, of *Cosmos sulphureus* and turnover rates of the resulting recombinant enzymes (0-5%: −, 6-30%: +, 31-60%: ++, 61-100%: +++).

In order to be able to identify, whether the striking regions, which were found in the alignments, have influence on the CH3H activity, five chimeric genes were constructed, which contain *C. sulphureus* CH3H and *C. sulphureus* F3'H cDNA fragments (C1-C5, FIGS. 4 and 5): C1: amino acid positions 1-196: F3'H and 201-512: CH3H; C2: amino acid positions 1-210: CH3H and 211-512: F3'H; C3: amino acid positions 1-119: CH3H and 124-512: F3'H; C4: amino acid positions 1-193: CH3H and 198-512: F3'H. The amino acid positions are based on the paired alignment of *C. sulphureus* F3'H and CH3H. All primers used for the generation of the chimeric genes are listed in FIG. 5, and a schematic representation of the chimeric genes is shown in FIG. 4.

Construction of Mutated cDNAs with Insertions and Deletions Targeted Mutagenesis Due to the particular properties of the amino acid proline (proline is a helix and sheet disrupter and is frequently found in loops or turns), P199 from the SAGG+N region in A199 was mutated according to the alanine, which can be found in the *Cosmos sulphureus* F3'H sequence at this position (FIG. 1). The primers used for that and a schematic representation can be found in Table 3 and FIG. 4, respectively.

Enzyme Activities of the Heterologously Expressed Chimeric and Mutated Enzymes

In total, two native enzymes from *C. sulphureus* as well as five chimeric (C1-C5) and three mutated enzymes (M1, M2 and M3, FIG. 4) were heterologously expressed in yeast. Studies with the recombinant enzymes in respect of their substrate acceptance showed that all the expressed enzymes except for M3 have F3'H activity (FIG. 4). The hydroxylation of chalcones, however, could only be observed with the chimeric genes C1, C2 and C5 as well as with M1. With the recombinant enzyme C1, however, only a low CH3H activity could be observed, compared to the F3'H activity and the CH3H activity of the other recombinant enzymes.

In order to determine kinetic data with various substrates, kinetic studies with the recombinant enzymes were performed. These kinetic data are listed in Table 1.

Example 2

The creation of transgenic apple trees takes place by transformation of young apple tree leaves using *Agrobacterium*, as described in the literature (Szankowski et al.; Plant Cell Rep 2003, 22 141-149). The plants are tested in the greenhouse as self-rooted plants or engrafted onto a conventional substrate under outdoor-light-like conditions. The leaves were examined for an increased 3-hydroxyphloretin content using HPLC, for example according to the method of Sato et al., 2001 (Plant Science 160, 229-336). A connection between pathogen defence and 3-hydroxyphloretin is known from the literature (Elstner, E. F., Oβwald, W., Schneider, I., 1996. Phytopathologie. Allgemeine and biochemische Grundlagen. Spektrum Akademischer Verlag, Heidelberg, Berlin, Oxford.). An increased resistance against *Erwinia amylovora* of the transgenic apples, which overexpress the nucleotide according to the invention, can be tested as follows: the shoots are cut back to a height of 10 cm 3-4 weeks before testing. The bacteria are cultured on King's B agar plates for 24 hours and subsequently resuspended in phosphate buffer. The cell concentration is spectrophotometrically set to $10^7$ cfu/ml. As the negative control, phosphate buffer is emptied onto empty King's B agar plates and decanted again. For inoculation, the leaf tips of the two youngest unfolded leaves are cut off with scissors, which were dipped into a culture solution with the pathogen beforehand. For each transgenic line, 10-20 individuals are tested and compared with the control. The degree of infection is calculated from the ratio of the length of the damaged shoot compared to the overall shoot length.

What is claimed is:

1. An isolated nucleic acid molecule, comprising a nucleotide sequence, which encodes a polypeptide with chalcone 3-hydroxylase activity, wherein the nucleotide sequence comprises SEQ ID NO. 1 or has at least a 80% identity with SEQ ID NO. 1, wherein the nucleotide sequence encodes a polypeptide, which comprises the motif FASRPLSSGG $(X_3)_m$(GSAGGD)$_n$ (SEQ ID NO. 5), wherein $X_3$ is any amino acid, m is an integer between 50 and 200, and n is 0 or 1.

2. A vector comprising the nucleic acid molecule of claim 1.

3. A cell comprising the nucleic acid molecule of claim 1, wherein the nucleic acid molecule is heterologous to the cell.

4. The cell of claim 3, further defined as a plant cell.

5. The cell of claim 3, wherein the nucleic acid molecule is comprised in a vector.

6. A transgenic plant comprising the nucleic acid molecule of claim 1, wherein the nucleic acid molecule is heterologous to the plant.

7. The transgenic plant of claim 6, wherein the nucleic acid molecule is comprised in a vector.

8. The transgenic plant of claim 6, further defined as an ornamental plant.

9. The transgenic plant of claim 8, further defined as a petunia, African violet, azalea, rhododendron, pelargonium, fuchsia, cyclamen, poinsettia, *Antirrhinum*, *Aster* (Asteraceae), *Begonia* (Begoniaceae), *Callistephus* (Asteraceae), *Campanula* (Campanulaceae), *Catharanthus* (Apocynaceae), *Chrysanthemum* (Asteraceae), *Cineraria* (Asteraceae), *Dedanthremum* (Asteraceae), *Dianthus* (Caryophyllaceae), *Dahlia* (Asteraceae), *Euphorbia* (Euphorbiaceae), *Gerbera* (Asteraceae), *Hydrangea* (Hydrangeaceae), *Lilium* (Liliaceae), *Lisianthus* (*Eustoma* (Gentianaceae)), *Myosotis*

(Boraginaceae), *Nierembergia* (Solanaceae), *Orchidaceae*, *Osteospermum* (Asteraceae), *Rosa* (Rosaceae), *Scaevola* (Goodeniaceae), *Sinningia* (Gesneriaceae), *Streptocarpus* (Gesneriaceae), *Torenia* (Linderniaceae), *Tulipa* (Liliaceae), *Verbena* (Verbenaceae), *Veronica* (Plantaginaceae), *Viola* (Violaceae), or *Malus* sp.

10. A cut flower or seed of the transgenic plant of claim 6, wherein said cut flower or seed comprises the nucleic acid molecule comprising the sequence which encodes a polypeptide with chalcone 3-hydroxylase activity.

* * * * *